US012589250B2

(12) United States Patent (10) Patent No.: US 12,589,250 B2
McIver et al. (45) Date of Patent: Mar. 31, 2026

(54) ASSEMBLIES AND METHODS FOR WIRELESSLY INTERFACING WITH AN IMPLANTABLE MEDICAL DEVICE

(71) Applicant: INSPIRE MEDICAL SYSTEMS, INC., Golden Valley, MN (US)

(72) Inventors: Jordan McIver, Blaine, MN (US); Douglas Murphy, Plymouth, MN (US); John Rondoni, Plymouth, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 278 days.

(21) Appl. No.: 18/280,156

(22) PCT Filed: Mar. 3, 2022

(86) PCT No.: PCT/US2022/018685
§ 371 (c)(1),
(2) Date: Sep. 1, 2023

(87) PCT Pub. No.: WO2022/187471
PCT Pub. Date: Sep. 9, 2022

(65) Prior Publication Data
US 2024/0139526 A1 May 2, 2024

Related U.S. Application Data

(60) Provisional application No. 63/156,502, filed on Mar. 4, 2021, provisional application No. 63/156,470, filed on Mar. 4, 2021.

(51) Int. Cl.
A61N 1/372 (2006.01)
(52) U.S. Cl.
CPC ............................... A61N 1/37247 (2013.01)

(58) Field of Classification Search
CPC ............ A61N 1/37247; A61N 1/36185; A61N 1/36132; A61N 1/08
USPC .............................................................. 607/2
See application file for complete search history.

(56) References Cited

U.S. PATENT DOCUMENTS

| | | | |
|---|---|---|---|
| 9,452,293 B2 | 9/2016 | Rondoni et al. | |
| 9,707,442 B2 | 7/2017 | Artemiadis et al. | |
| 9,839,786 B2 | 12/2017 | Rondoni et al. | |
| 9,913,982 B2 | 3/2018 | Bolea et al. | |
| D832,865 S | 11/2018 | Dieken et al. | |
| D833,461 S | 11/2018 | Dieken et al. | |
| D840,426 S | 2/2019 | Dieken et al. | |
| D869,490 S | 12/2019 | Rondoni et al. | |
| D871,433 S | 12/2019 | Rondoni et al. | |
| D871,434 S | 12/2019 | Rondoni et al. | |
| 10,632,306 B2 | 4/2020 | Bolea et al. | |

(Continued)

FOREIGN PATENT DOCUMENTS

| | | |
|---|---|---|
| EP | 3061493 B1 | 7/2018 |
| WO | 2016112398 A1 | 7/2016 |
| WO | 2021016558 A1 | 1/2021 |

OTHER PUBLICATIONS

"Inspire Programmer Manual", Programmer Model 2740, Inspire Medical Systems, Inc., 2020 (112 pages).

*Primary Examiner* — Nadia A Mahmood
(74) *Attorney, Agent, or Firm* — Dicke, Billig & Czaja, PLLC

(57) ABSTRACT

An assembly and/or method to facilitate wireless communicates between an implantable medical device and a programmer.

30 Claims, 41 Drawing Sheets

(56)                    References Cited

U.S. PATENT DOCUMENTS

| | | | |
|---|---|---|---|
| 10,737,094 B2 | 8/2020 | Bolea et al. | |
| 10,779,731 B2 | 9/2020 | Chmiel et al. | |
| 2011/0004276 A1 | 1/2011 | Blair et al. | |
| 2015/0297137 A1 | 10/2015 | Welch et al. | |
| 2015/0360038 A1 | 12/2015 | Zottola et al. | |
| 2016/0051825 A1* | 2/2016 | Ter-Petrosyan | A61N 1/37247 607/60 |
| 2019/0175026 A1 | 6/2019 | Verzal et al. | |
| 2019/0365228 A1 | 12/2019 | Rondoni et al. | |
| 2019/0371478 A1 | 12/2019 | Rondoni et al. | |
| 2019/0371479 A1 | 12/2019 | Rondoni et al. | |
| 2020/0138311 A1 | 5/2020 | Min | |
| 2020/0346017 A1 | 11/2020 | Caparso et al. | |
| 2022/0079438 A1 | 3/2022 | Baek et al. | |

* cited by examiner

300

ASSEMBLIES AND METHODS FOR WIRELESSLY INTERFACING WITH AN IMPLANTABLE MEDICAL DEVICE

CROSS-REFERENCE TO RELATED APPLICATIONS

This application is a U.S. National Stage Application under 35 U.S.C. § 371 of International Application No. PCT/US2022/018685, filed Mar. 3, 2022, which claims the benefit of U.S. Provisional Patent Application No. 63/156,502, filed Mar. 4, 2021, and claims the benefit of U.S. Provisional Patent Application No. 63/156,470, filed Mar. 4, 2021, each of which are incorporated herein by reference in their entireties.

BACKGROUND

Some implantable medical devices may be programmable via external devices which communicate with the implantable medical devices via various wireless communication protocols.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to a method and/or assembly to facilitate wirelessly interface between a programmer and an implantable medical device (IMD), such as an implantable pulse generator (IPG), for example to program the IMD. In some such examples, the IPG may already be implanted within a patient and the programming may include programming therapy stimulation settings, etc.

In some examples, the wireless interface may be initiated or controlled by a clinician intending to perform various types of programming, such as for an initial activation of a recently implanted IPG, a followup visit by the patient to the clinician, a sleep study evaluation of therapy effectiveness, and the like. It will be understood that the term clinician may refer to a device therapy technician, sleep study technician, a physician, or other medical worker suitably experienced to conduct (or assist with) the example workflows.

In some examples, the systems and methods of the present disclosure are configured and used to interface with an IMD intended to provide sleep disordered breathing (SDB) therapy, such as obstructive sleep apnea (OSA) therapy. However, in other examples, the IMD is used for other types of therapy, including, but not limited to, other types of neurostimulation or cardiac therapy. In some embodiments, such other implementations include therapies, such as but not limited to, central sleep apnea, complex sleep apnea, cardiac disorders, pain management, seizures, deep brain stimulation, and respiratory disorders.

Figure 1:
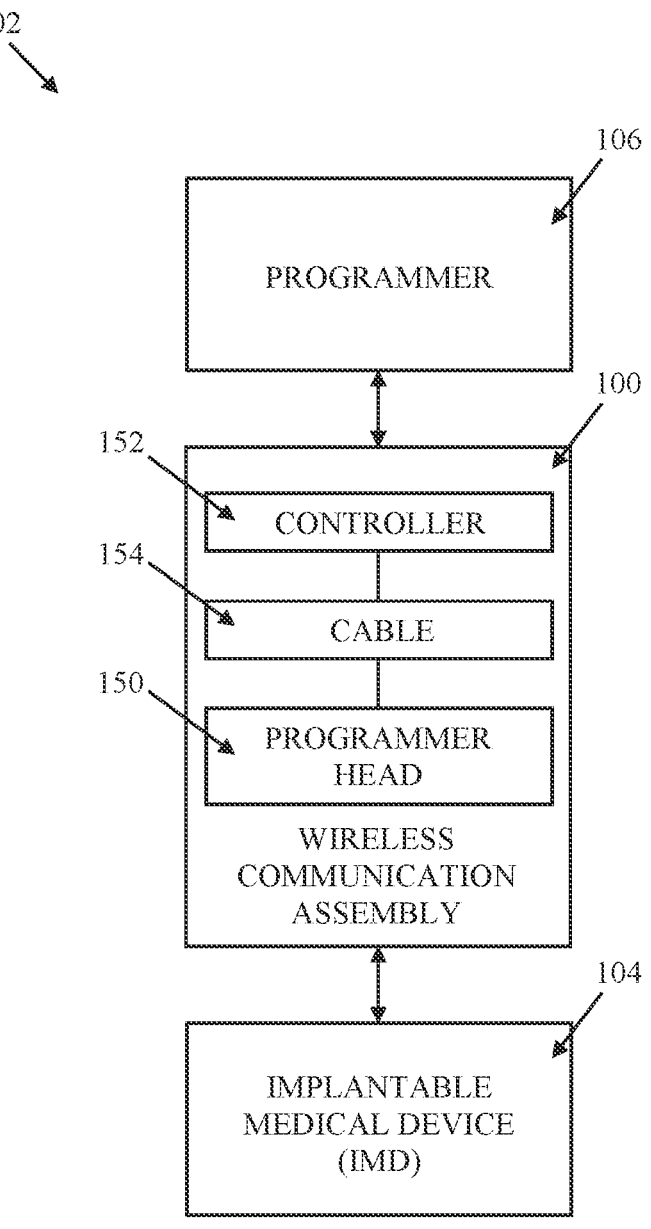
FIG. 1 is a block diagram schematically representing a wireless communications assembly in accordance with principles of the present disclosure as part of an example arrangement including a programmer and an implantable medical device.

One example of a wireless interface assembly 100 (sometimes referred to as a "programmer cable") in accordance with principles of the present disclosure is shown in FIG. 1 as part of an example arrangement (e.g., system) 102 that further includes an implantable medical device (IMD) 104 and a programmer 106. The IMD 104 and the programmer 106 can assume various forms, and the present disclosure is in no way limited to a particular format. In general terms, the IMD 104 may comprise an implantable pulse generator (IPG), which in some examples may comprise an IPG for treating sleep disordered breathing (SDB) and/or other patient conditions (e.g. cardiac, pelvic disorders, etc.), as is known in the art. The programmer 106 may communicate with the IMD 104 (and vice-versa) via the wireless interface assembly 100. The programmer 106 may sometimes be referred to as a clinician programmer (or "clinician tablet") to the extent that the programmer 106 is expected to be employed by a clinician.

The programmer 106 can assume various forms, for example a tablet computer or other mobile computing device (e.g., a notebook or laptop). The programmer 106 can be configured to implement an application (or "app") or a browser that facilitates clinician interaction with the wireless interface assembly 100 and the IMD 104. In general terms, the programmer 106 can be used by a clinician to interrogate the IMD 104 and make adjustments to various parameters of the IMD 104 (referred to as "programming" the IMD), monitor therapy delivered by the IMD 104, monitor patient adherence to prescribed therapy, etc.

The wireless interface assembly 100 is configured to wirelessly communicate with both the IMD 104 and the programmer 106. In some embodiments, then, the wireless interface assembly 100 effectively serves as a wireless bridge between the programmer 106 and the IMD 104. In some examples, the wireless interface assembly 100 and the programmer 106 can be provided to a user (e.g., clinician) together as a "programmer unit" or "programming unit" for interfacing with the IMD 104. In some embodiments, the wireless interface assembly 100 comprises disparate communication devices that together support a communication channel comprising disparate sequential communication links configured to facilitate bidirectional communication between the IMD 104 and the programmer 106. In some embodiments described below, the wireless interface assembly 100 is configured to self-monitor its connectivity with one or both of the IMD 104 and the programmer 106, and to indicate a status of the connectivity. In some embodiments described below, the wireless interface assembly 100 is configured to afford a user the ability to test communicative links, for example with the IMD 104, directly at the wireless interface assembly 100 and outside of the presence of the programmer 106.

Against the above background, the wireless interface assemblies of the present disclosure, such as the wireless interface assembly 100, includes a programmer head 150, a controller 152, and a cable 154. In general terms, the programmer head 150 is configured to wirelessly communicate with the IMD 104 via, for example, a near-field link (e.g., as a telemetry head). The controller 152 is configured to wirelessly communicate with the programmer 106, for example via short-range radio frequency (RF) communication (e.g., Bluetooth®). The cable 154 extends between the programmer head 150 and the controller 152, and provides wired links between components of the programmer head 150 and the controller 152; optionally, the cable 154 can deliver power to the programmer head 150.

The programmer head 150 can incorporate various features or components as known in the art appropriate for establishing the wireless communications with the IMD 104 as summarized above, and the present disclosure is in no way limited to a particular wireless format. By way of non-limiting example, the programmer head 150 can be configured to (e.g., include or carry electronic components capable of) inductively communicate with the IMD 104 via a near-field link. A near-field link appropriate for effecting communications with an IMD typically has a range of about 5 centimeters. A typical near-field link between the programmer head 150 is highly directional, operates safely through human tissue, and may be susceptible to electrical noise. In addition to being extremely short range, inductive telemetry communication is low-power and does not interfere with medial or communication equipment. In other examples, an alternative to near-field inductive communication can be implemented, including, but not limited to: e-field communications (MICS, ISM), and medium range induction technology which utilized advance amplifiers and transmitters to achieve ranges up to 1 meter. It is noted that the use of multiple coils, such as in three-axes implementations, can minimize or eliminate the directionality issues with inductive links. In some optional embodiments described below, minimal electrical, wireless communication-related components are carried by a housing of the programmer head 150; for example, the programmer head 150 can optionally include an antenna (or the like), with a remanded of the electrical components necessary to establish a wireless link with the IMD 104 being carried by the controller 152.

Similarly, the controller 152 can incorporate various features or components as known in the art appropriate for establishing the wireless communications with the programmer 106 as summarized above, and the present disclosure is in no way limited to a particular wireless format. By way of non-limiting example, the controller 152 can be configured to or include wireless transceiver components or technology. The controller 152 can be configured to (e.g., include or carry electrical components capable of) short-range radio frequency (RF) communication. For example, the controller 152 can be configured to implement a short-range RF communication link, such as by implementing a Bluetooth® (short-wavelength UHF radio waves in the ISM band from 2.4 to 2.485 GHz) or ZigBee® communications protocol. In some embodiments, the controller 152 can be configured to wirelessly communicate with existing network infrastructure via an appropriate communication protocol, such as Wi-Fi® (also considered a short-range RF communications link of up to about 45 meters indoors). In such embodiments, a hybrid communication link can be established between the controller 152 and the programmer 106 using a wireless local area network (WLAN) via a wireless network connection.

Regardless of the particular wireless communication format or technology provided with the programmer head 150 and the controller 152 (it being understood that the IMD 104 will incorporate components appropriate for wirelessly communicating with the programmer head 150, and the programmer 102 will incorporate components appropriate for wirelessly communicating with the controller 152 as will be apparent to those of ordinary skill), in some embodiments, one or both of the programmer head 150 and/or the controller 152 will include or incorporate features that facilitate ease of use in evaluating a patient following implantation of the IMD 104.

As a point of reference, in some non-limiting examples, the IMD 104 is intended to provide SDB therapy to a patient. For example, the IMD 104 can include a stimulation component and a sensing component. In some examples, the stimulation component comprises a stimulation engine to generate a stimulation signal to be applied to a tissue (e.g., nerve, muscle, etc.). In the examples in which the IMD 104 comprises an implantable pulse generator (IPG), the tissue to be stimulated may comprise tissue to maintain or restore upper airway patency, such as but not limited to a hypoglossal nerve, an ansa cervicalis-related nerve, and/or phrenic nerve, etc. In some such examples, the stimulation component also may comprise circuitry for generating and delivering the stimulation signal. In some examples, the stimulation component of the IMD 104 also may comprise a stimulation element, such as an electrode through which the stimulation signal may be applied to the target tissue. Of course, in contexts in which the IMD 104 relates to bodily organs, functions, etc. other than sleep disordered breathing, the stimulation component and sensing component would be deployed relative to other tissues. For instance, the IMD 104 may be deployed to treat pelvic disorders, such as stress incontinence or other conditions, with applicable tissues including the bladder, pudendal nerve, urinary and/or anal sphincters and the like. Regardless, with these and other examples, a clinician may program the IMD 104 for initial activation/therapy delivery and/or perform followup programming assessment as part of a sleep study or other patient review or study. The sleep study assessment may occur following initial implant, at recommended intervals sometime after initial activation, followup, etc., or may occur at any time it is desired to evaluate efficacy of the IMD 104 and its programming.

Figure 2:
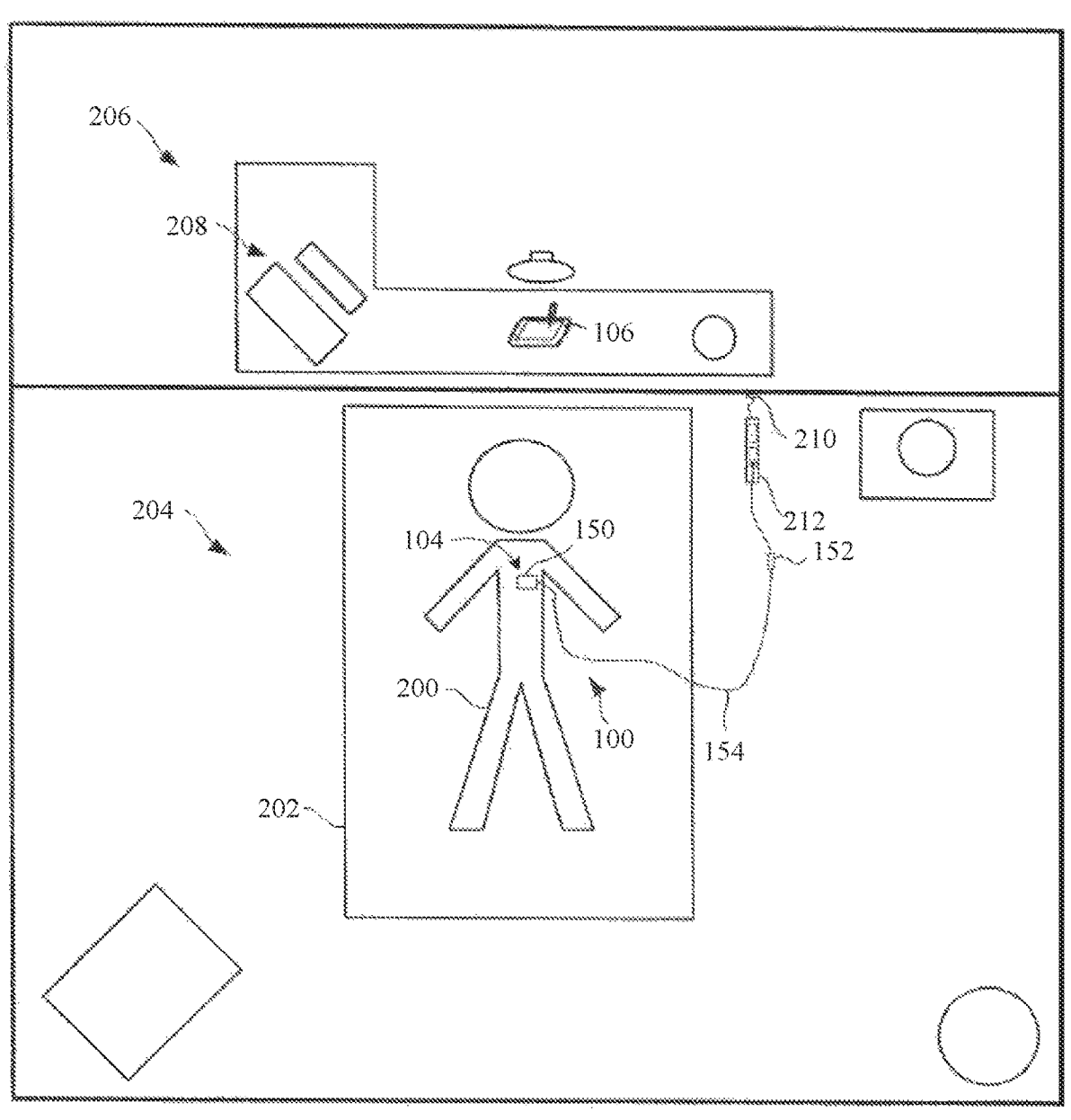
FIG. 2 is an illustration of a clinic or hospital equipped to monitor a patient during a medical evaluation, such as a sleep study, with which the wireless communication assemblies of the present disclosure are useful.

For example, FIG. 2 is an illustration of clinic or hospital rooms equipped to monitor a patient 200 during a medical evaluation, such as a sleep study. In this example, the IMD 104 (referenced generally) has been implanted in the patient 200 for the purpose of treating SDB as is known in the art. As a point of reference, the IMD 104 can include an implantable pulse generator (IPG) and one or more leads extending therefrom. The patient 200 is shown lying down on a bed 202 in a patient room 204 for purposes of conducting the sleep study. FIG. 2 also shows a clinician room 206 which is typically a separate room adjacent to or near the patient room 204. The clinician room 206 is typically close to the patient room 204 to facilitate efficient evaluation of, and communication with, the patient 200 during the sleep study. The clinician room 206 is typically separated from the patient room 204 by a wall or other privacy structure; although a one-way mirror or the like is normally installed so that a clinician in the clinician room 206 can view the patient 200, the wall provides a measure of privacy and security for the patient 200 during the sleep study. During the sleep study, the programmer 106 is normally situated in the clinician room 206, along with other possible tools 208. The wireless interface assembly 100, in turn, is with the patient 200 in the patient room 204, facilitating communication between the programmer 106 and the IMD 104. With this arrangement, the programmer 106 can be used by a clinician to interact with the IMD 104 without disturbing the patient's sleep, which can be important for conducting productive sleep studies. As implicated by FIG. 2, the wireless interface assembly 100 generally facilitates this communication when the programmer head 150 is located in very close proximity to the IMD 104, sufficient to establish a wireless connection. The controller 152 is connected to the programmer head 150 by the cable 154. The wireless interface assembly 100 can be connected to a conventional power supply 210 by a power cable 212; alternatively, one or both of the programmer head 150 and the controller 152 can be battery powered. Regardless, a wireless link is established between the controller 152 and the programmer 106.

Preparation of the above-described sleep study scenario requires performance of a multitude of tasks by the clinician, including establishing/confirming a satisfactory wireless connection between the programmer head 150 and the IMD 104. Conventionally, the programmer 106 must be operated by the clinician in order to initially establish telemetry connection between the programmer head and the IMD 104. Where the programmer 106 is located in the clinician room 206 (or any other room separate from the patient room 204), the clinician must go back-and-forth to the patient room 204 to complete the initial connection, constantly re-visiting the programmer to ascertain a status of the telemetry connection; this delay can be inefficient and potentially uncomfortable for the patient 200. Similar concerns arise when establishing/confirming a satisfactory wireless connection (or pairing) between the controller 152 and the programmer 106 with conventional designs. Throughout the sleep study, it can be important for the clinician to continuously confirm the status of these wireless connections. Preferably, however, the clinician will not enter the patient room 204 during more critical times of the sleep study, especially when the patient room 204 is dark and the patient 200 is sleeping or attempting to sleep. The sleep study environment is typically, though undesirably, hostile electronically, and clinicians often are tasked with reducing any impediments to a patient's sleep (e.g., removing cell phones, using heated blankets, minimizing discomfort of sensor wires on the patient 200, etc.). The wireless communication assemblies of the present disclosure can further promote successful sleep studies, incorporating one or more features that facilitate one or more aspects of sleep study (or other patient examination or testing session) preparation and performance as described below.

Figure 3:
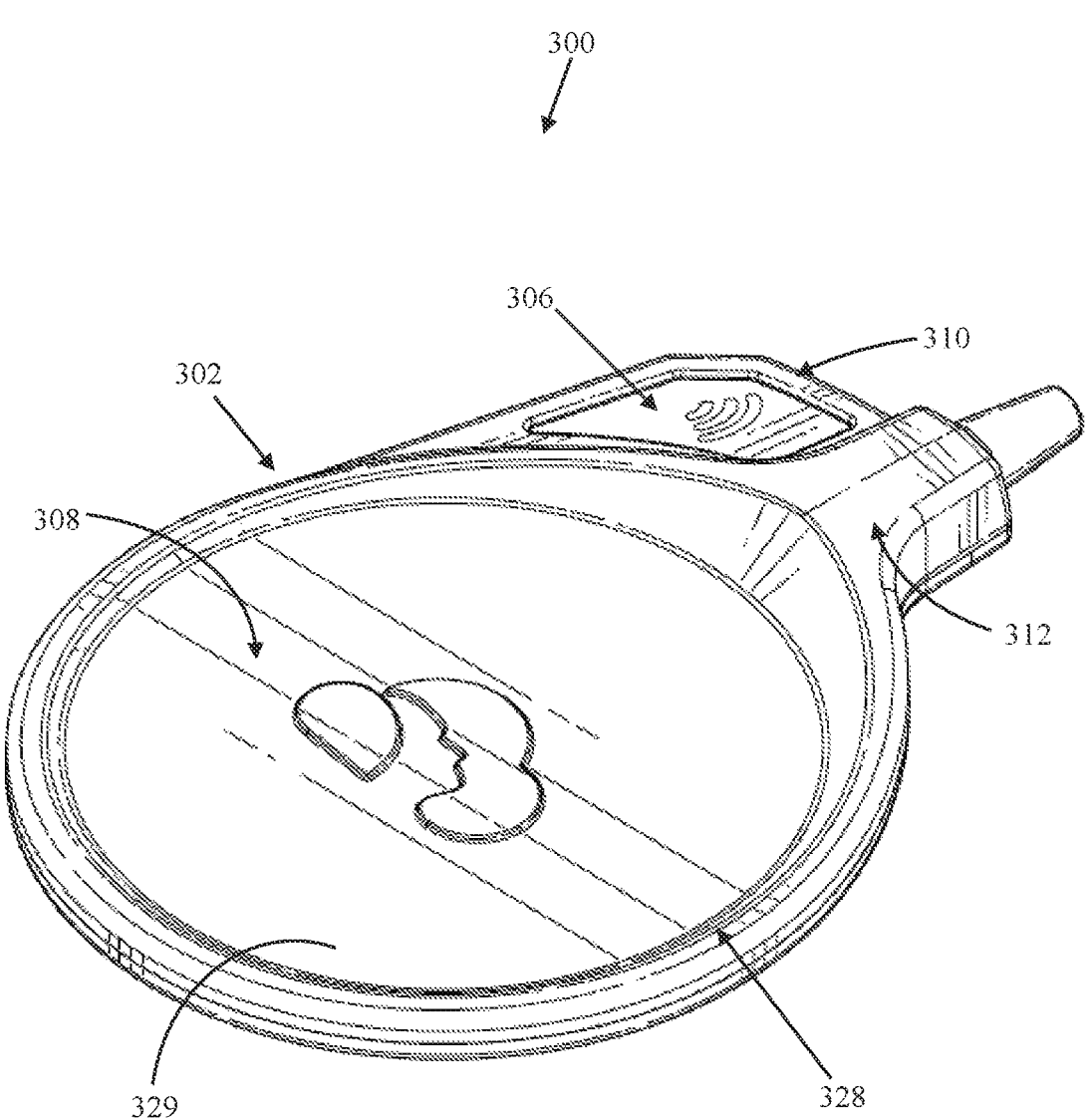
FIG. 3 is a perspective view of a programmer head useful with the wireless communications assembly of FIG. 1.
Figure 4:
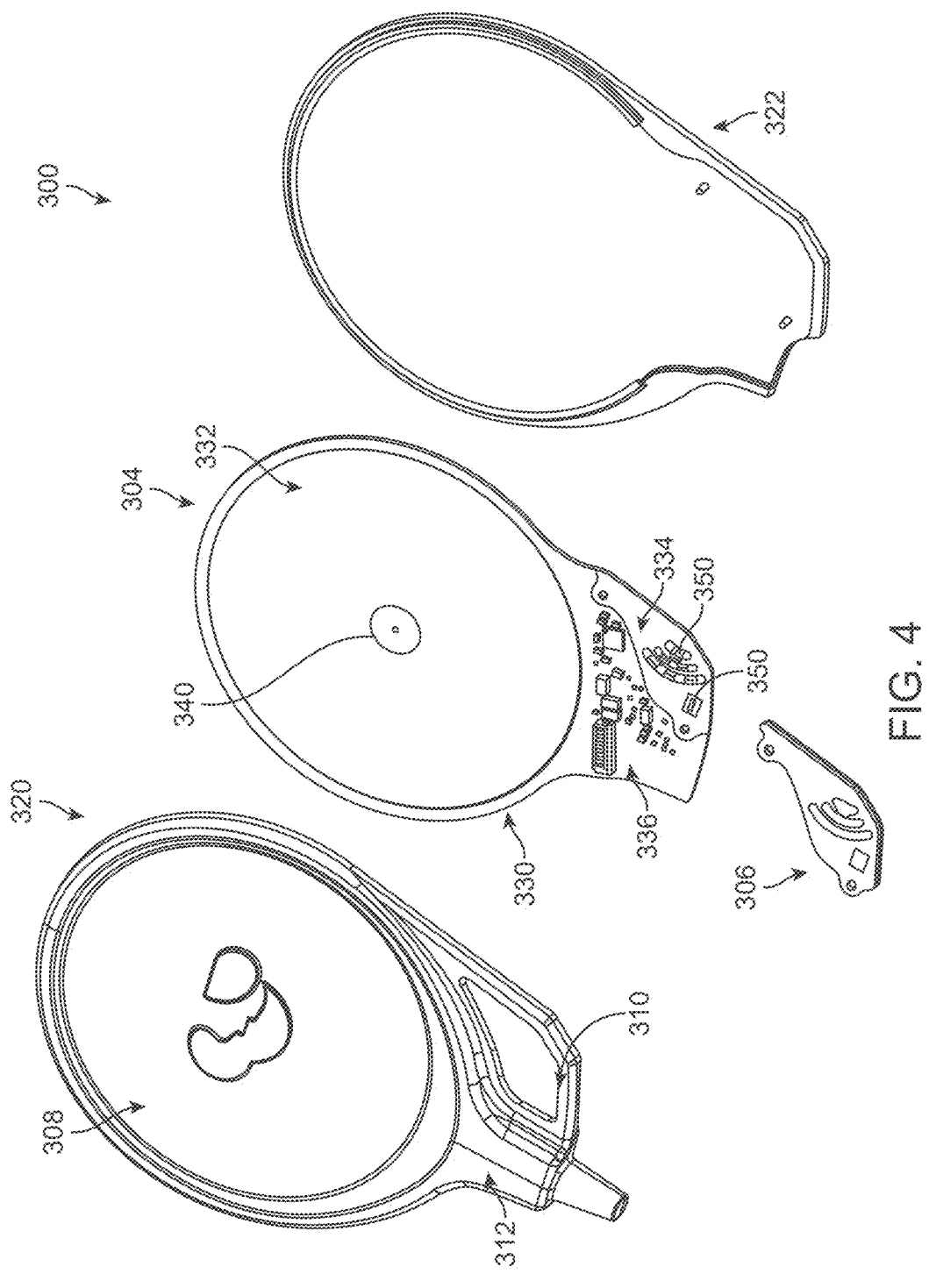
FIG. 4 is an exploded, perspective view of the programmer head of FIG. 3.

For example, one example of a programmer head 300 of the present disclosure (and useful, for example, as the programmer head 150 of FIG. 1) is shown in FIGS. 3 and 4. The programmer head 300 includes a housing 302, a circuit board assembly 304, and a display body 306. In general terms, the housing 302 contains the circuit board assembly 304, and provides or defines a placement region 308, a display region 310, and a neck region 312. The circuit board assembly 304 includes or carries at least one wireless communication-related component located to correspond with the placement region 308, and one or more illumination components located to correspond with the display region 310. Where provided, the indicator body 306 is arranged at the display region 310, and provides features that affect light from the illumination components to generate a desired visual appearance at an exterior of the programmer head 300 as described below.

Figure 5:
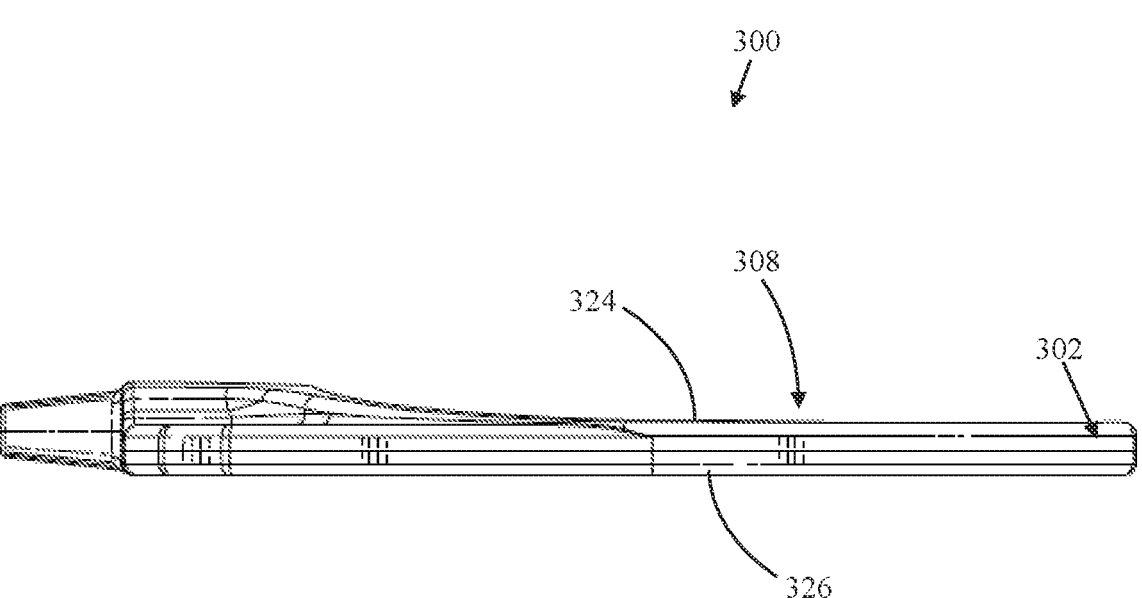
FIG. 5 is a side view of the programmer head of FIG. 3.

The housing 302 can be formed in various fashions, and in some embodiments can be a homogenous body that is formed (e.g., over-molded) about the circuit board assembly 304 and the display body 306 (as well as any other optional internal components provided with the programmer head 300). Thus, while FIG. 4 implicates the housing 302 has having a top section 320 separate from a tray section 322, in some embodiments the top section 320 and the tray section 322 are an integral or homogenous body. Alternatively, the top section 320 and the tray section 322 can be separately formed and subsequently assembled to one another. In some non-limiting embodiments, the housing 302 (e.g., the top section 320 and the tray section 322) is formed of a plastic material (e.g., conducive to over-molding manufacture as mentioned above) formulated to be rubbery, flexible, or conformable. Further, and in some embodiments, exterior surface(s) of the housing 302 can be formed to exhibit a tacky or "sticky" attribute. As a point of reference, and with additional reference to FIG. 5, the housing 302 defines an upper face 324 opposite a lower face 326. An intended orientation of the programmer head 300 during use is such that the lower face 326 is located against a patient, and in particular along the placement region 308. In some embodiments, the housing 302 is formed (e.g., a material of the housing 302 or material coating applied to an exterior of the housing 302) such that the lower face 326 along the placement region 308 is at least somewhat tacky or sticky. The optional conformable and tacky attributes of the housing 302 can facilitate the programmer head 300 comfortably remaining in place on a patient for an extended period of time. With this in mind, in some embodiments the housing 302 is formed of, or is, overmolded with thermoplastic elastomer having a durometer on the order, for example, of 52 Shore A. In other embodiments, an entirety of the external surfaces of the housing 302 exhibit the same tacky or sticky feel. In yet other embodiments, the housing 302 need not have a discernable tackiness or stickiness.

In some embodiments, the housing 302 can incorporate features that visually indicate or suggest to a user that during use of the programmer head 300, the lower face 326 is intended to be placed on the patient (and thus the upper face 324 is intended to be away from or opposite the patient). For example, the lower face 326 can be flat or smooth across an entirety of a length and width of the housing 302 (readily understood to represent a surface well-suited for lying or placement on a patient's body), whereas the upper face 324 is not. For example, and returning to FIGS. 3 and 4, a raised ridge 328 can be formed about a perimeter edge of the upper face 324, creating a central depression 329 (referenced generally). The visual appearance of the perimeter ridge 328/central depression 330 at the upper face 324 as compared to the otherwise flat lower face 326 readily conveys to a user/clinician that the lower face 326 should be placed on the patient's body, and not the upper face 324. Other features can be incorporated into the housing intended to implicate a correct orientation during use. In other embodiments, the raised perimeter ridge 328 can be omitted.

To further promote patient comfort and other benefits, in some embodiments the programmer head 300 is configured to exhibit a relatively thin or low profile at least along the placement region 308. This optional low profile attribute is generated, in some embodiments, by features of the circuit board assembly 304 and the housing 302. For example, the circuit board assembly 304 can be, or can be akin to, a printed circuit board assembly (PCBA) or a flex circuit, and generally includes a base 330 (e.g., single or multi-layer board or film) supporting various electronic or electrical components and forming or supporting circuitry traces connecting to various ones of the electrical components. A perimeter shape of the base 330 corresponds with that of the housing 302, and thus can be viewed as defining a placement zone 332 that corresponds with the placement region 308, a display zone 334 that corresponds with the display region 310, and a neck zone 336 that corresponds with the neck region 312. With these general definitions in mind, in some embodiments, a wireless communication-related component in the form of an antenna 340 (referenced generally) is formed at or carried by the base 330 at the placement zone 332 (e.g., centered about or relative to a center point of the generally circular perimeter shape of the placement zone 332 in some embodiments). The antenna 340 can have any form useful for telemetry-type interface with an implantable medical device. Apart from the antenna 340, the placement zone 332 can be free or substantially free, of any other electrical components. With this optional construction, then, the circuit board assembly 304 can be highly thin along at least the placement zone 332, essentially defined by a thickness of the base 330 alone. The housing 302, in turn, mimics this thin, low profile size or shape, allowing the programmer head 300 to be thin or streamlined, especially along the placement region 308. The flat, low profile construction can be more comfortable for a patient during use as compared to conventional designs. In some embodiments, a nominal thickness of the programmer head 300 along at least the placement region 308 can be on the order of 0.2-0.8 inch, optionally on the order of 0.4 inch, although other dimensions are acceptable.

Various LEDs 350 (or other illumination or lighting devices) can be carried by the base 330 at the display zone 334. The LEDs 350 are arranged in a pattern corresponding with windows formed by the display body 306 that in turn convey information to a viewer when illuminated as described in greater detail below. For example, and with reference to the enlarged view of FIG. 6, the display body 306 can form or define first, second and third strength gauge windows 360, 362, 364, and an EMI window 366. In some embodiments, the LEDs 350 of the circuit board assembly 304 can include first and second LEDs 370, 372 arranged to reside within and illuminate the first strength gauge window 360; for reasons made clear below, the first and second LEDs 370, 372 of the first strength gauge window 360 can be formatted to emit a different color (e.g., the first LED 370 emits blue light, whereas the second LED 372 emits orange light). LEDs 374 arranged to reside within and illuminate the second strength gauge window 362 can be formatted to emit a color similar to the first LED 370 (e.g., blue light); similarly, LEDs 376 arranged to reside within and illuminate the third strength gauge window 364 can be formatted to emit a color similar to the first LED 370 (e.g., blue light). Finally, an LED 378 arranged to reside within and illuminate the EMI window 366 can be formatted to emit a color distinct from the first LED 370 (and the LEDS 374, 376), for example orange light. Thought not directly evident from the view of FIG. 6, the display body 306 can further include a top layer or film that creates a distinct visual appearance when illuminated, as described in greater detail below. Other LED (or other light emitting device) arrangements are also acceptable. Similarly, the display body 306 can have other forms.

Returning to FIG. 4, while the circuit board assembly 304 can carry or include various electrical components appropriate for delivering power to selected ones of the LEDs 350, in some embodiments the logic for determining which LEDs 350 should be energized and/or controlling the delivery of power to the selected LEDs 350 is not maintained or provided with the circuit board assembly 304 (or any other portion of the programmer head 300). For example, in some embodiments, the control logic is provided by a processor or chip carried by the controller 152 (FIG. 1) as described below. Regardless, the programmer head 300 is configured to provide designated displays at the display region 310 under pre-determined operational conditions.

Figure 6:
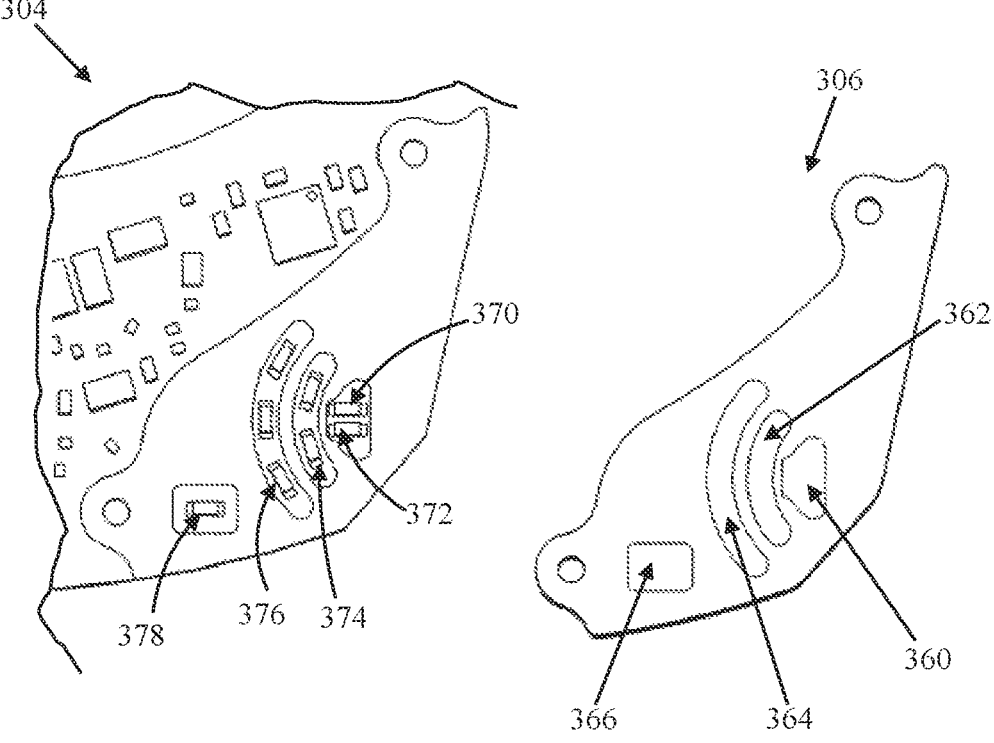
FIG. 6 is an enlarged, exploded top view of portions of the programmer head of FIG. 3.

For example, the programmer head 300 can provide a telemetry head strength gauge icon display, generating granular user feedback regarding placement of the programmer head 300 relative to an implanted IMD 104 (FIG. 2). With reference to FIG. 6, where it is determined that a strong telemetry communications link has been established, selected ones of the LEDs 350 can be energized (e.g., the LEDs 370, 374, 376) to illuminate the first-third strength gauge windows 360-364, resulting in an icon display 380 of FIG. 7A. The "strong connection" icon display 380 can be characterized as three illuminated, curved, blue bars of increasing size in some examples. Where it is determined that a moderate strength telemetry communications link has been established, a "moderate" telemetry strength icon display 382 can be generated as in FIG. 7B. For example, the LEDs 370, 374 can be energized to illuminate the first and second strength gauge window 360, 362, generating the icon display 382 as two illuminated, curved, blue bars that is visually distinct from the "strong connection" icon display 380 of FIG. 7A (e.g., the large third strength gauge window 364 is not illuminated). Where it is determined that a low telemetry communications link has been established, a further reduced or "low" telemetry strength icon display 384 can be generated as in FIG. 7C. For example, the LED 370 can be energized to illuminate the first strength gauge window 360, generating the icon display 384 of a single illuminated, curved, blue bar that is visually distinct from the "strong connection" icon display 380 of FIG. 7A and the "medium strength" icon display 382 of FIG. 7B (e.g., only the smallest, first strength gauge window 360 is illuminated with blue light in FIG. 7B). Finally, where it is determined that no telemetry communications link or signal has been established (or has failed), the second LED 372 can be energized to illuminate the first strength gauge window 360, generating the "no communications" or "no signal" icon display 386 of FIG. 7D. As evidenced by a comparison of FIG. 7D with FIGS. 7A-7C, the "no communications" icon display 386 is characterized at least by a markedly different color (e.g., orange in FIG. 7D versus blue in FIGS. 7A-7C).

Figure 8:
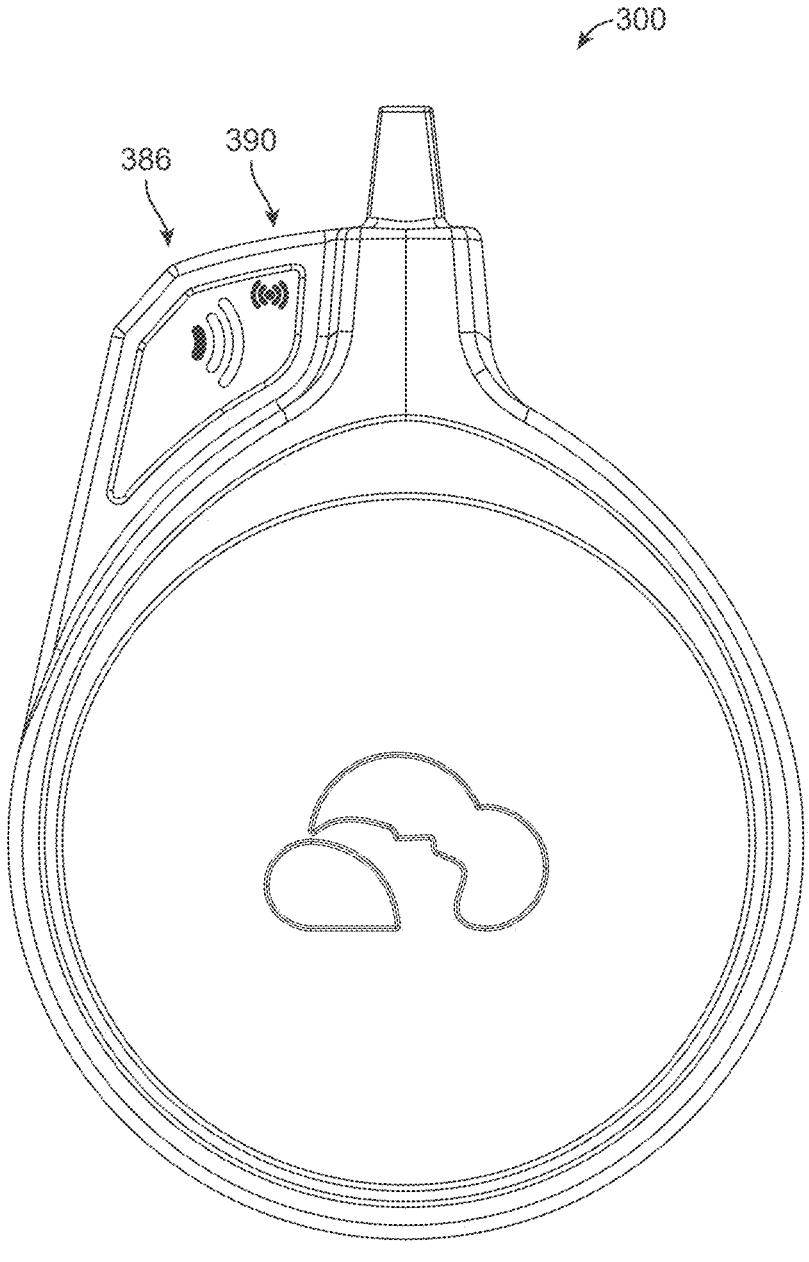
FIG. 8 illustrates an example EMI display available with the programmer head of FIG. 3.

In some embodiments, the programmer head 300 can further provide an EMI indicator. As a point of reference, in some non-limiting examples, logic provided with the wireless communications assembly 100 (FIG. 1) can evaluate or determine if electrical noise is disturbing communications between the programmer head 300 and the implanted IMD 104 (FIG. 2). This controller or logic can, in some embodiments, be carried apart from the programmer head 300, with the controller delivering signals to the circuit board assembly 304 to prompt operation of the selected LED(s) 350. Regardless, where it is determined that electrical noise is disturbing communication, the LED 378 (FIG. 6) can be energized to illuminate the EMI window 366, generating the EMI icon or indicator display 390 of FIG. 8. The EMI icon can appear as or the like, in a distinct color such as orange. FIG. 8 further reflects that under some circumstances where electrical noise is being detected, no signal between the programmer head 300 and the IMD 104 is occurring, such that the "no signal" icon 386 is also displayed.

Figure 7A:
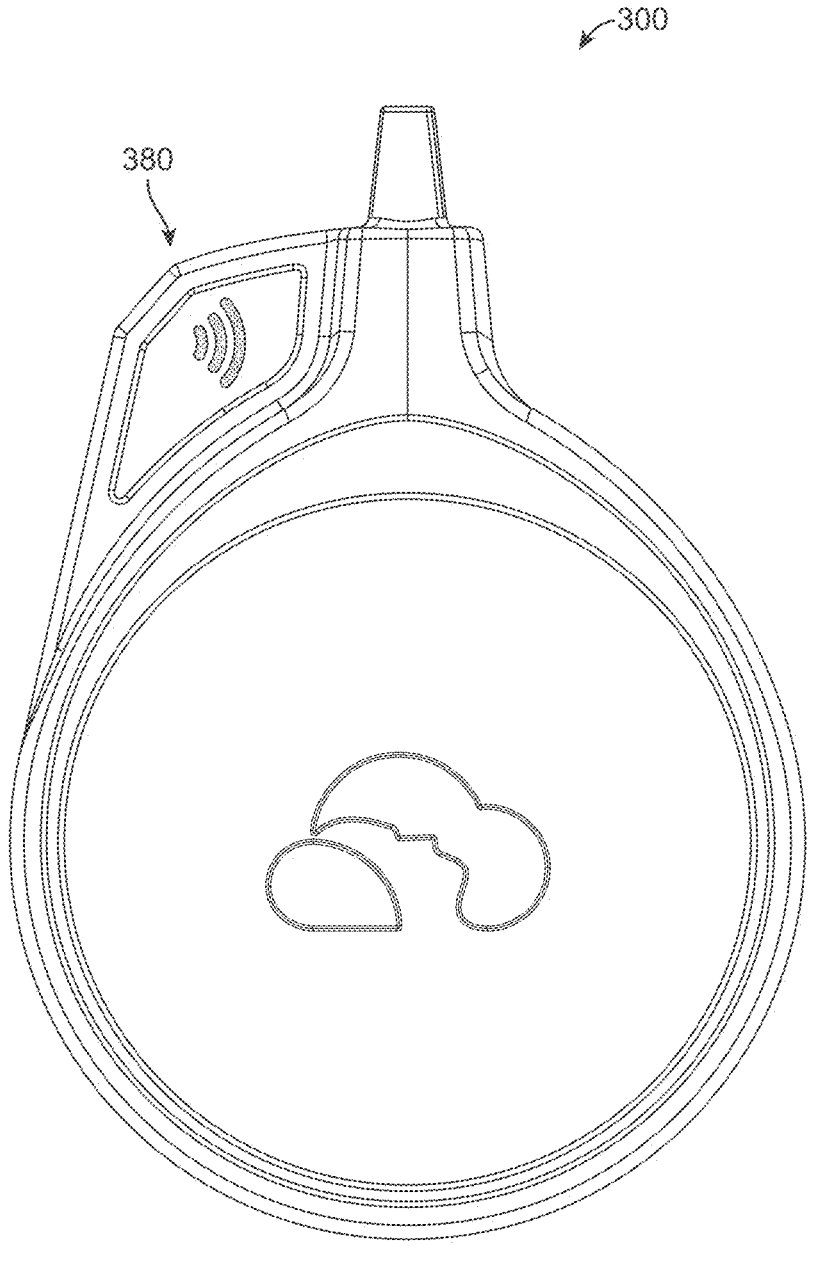
FIGS. 7A-7D illustrate example telemetry strength displays available with the programmer head of FIG. 3.
Figure 7B:
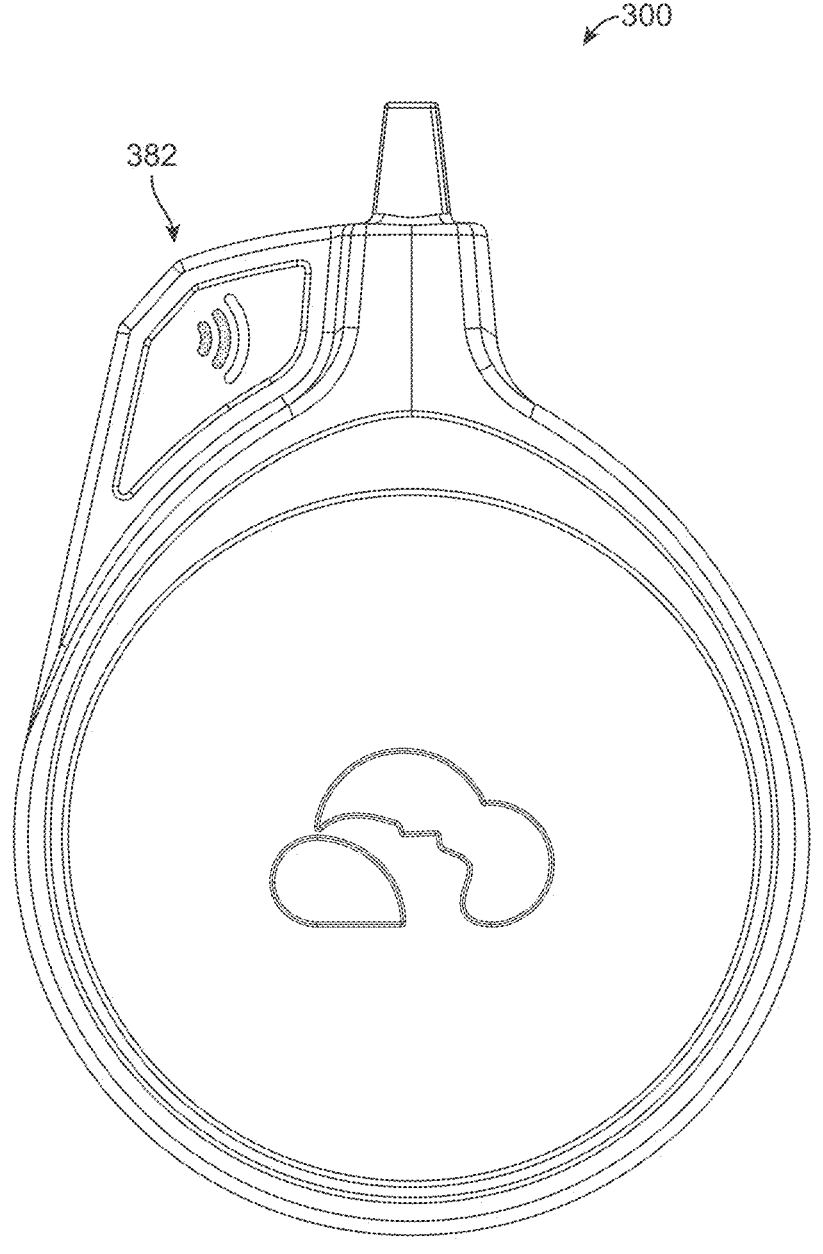
Figure 7C:
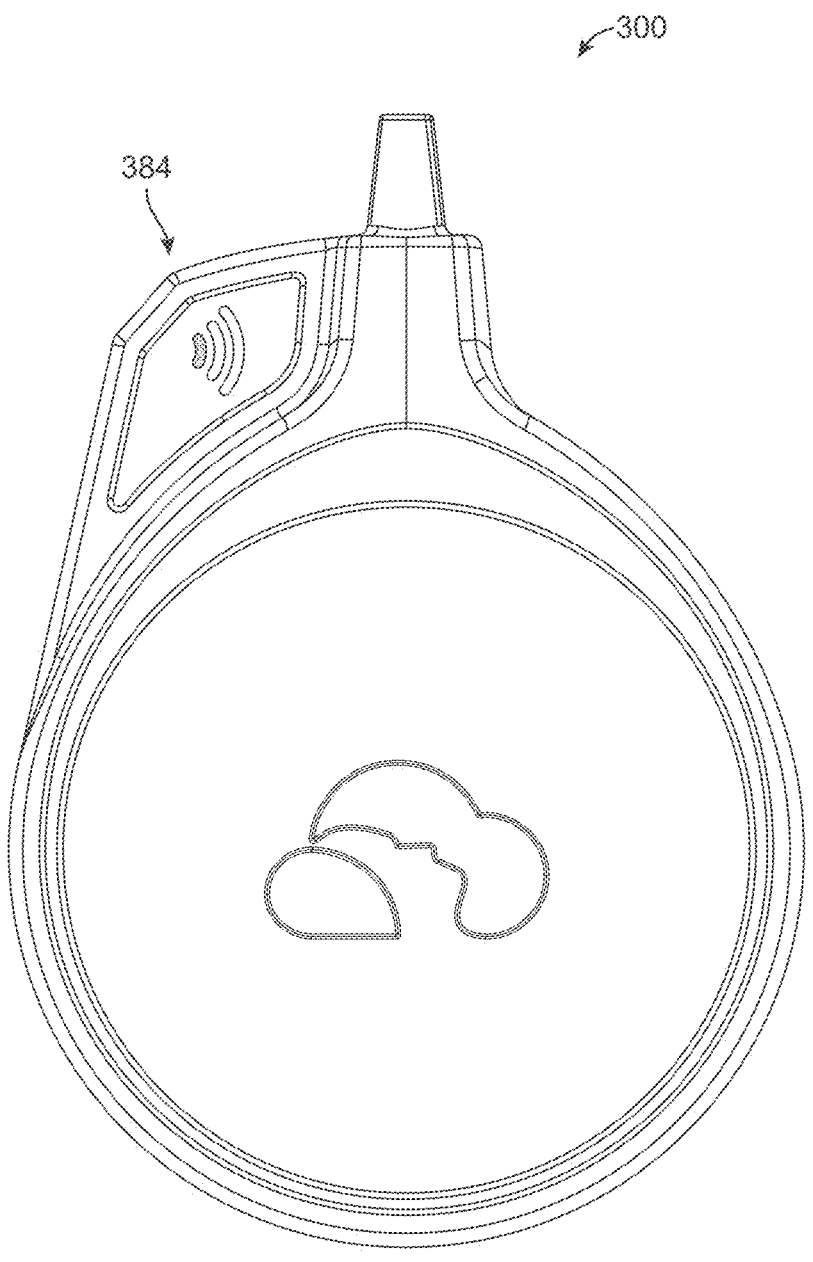
Figure 7D:
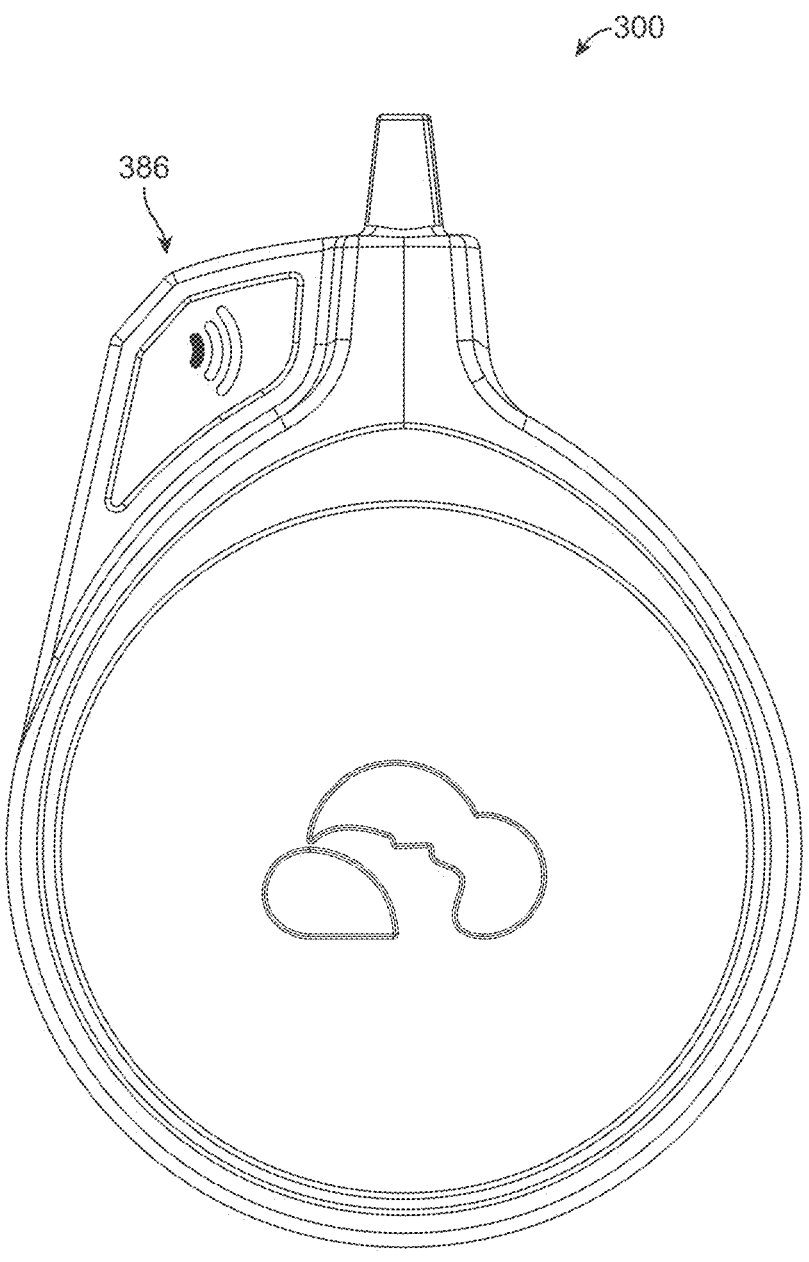

The icons or displays of FIGS. 7A-8 are in no way limiting, and other icons can be utilized to convey information at the programmer head 300 relating to wireless communications strength and/or electrical noise. In other embodiments, operational parameter other than, or in addition to, one or both of wireless communications and electrical noise. In yet other embodiments, the programmer head 300 can be caused or prompted to operate in a "night mode" as described below in which all of the LEDs 350 (FIG. 4) are deactivated.

Figure 9A:
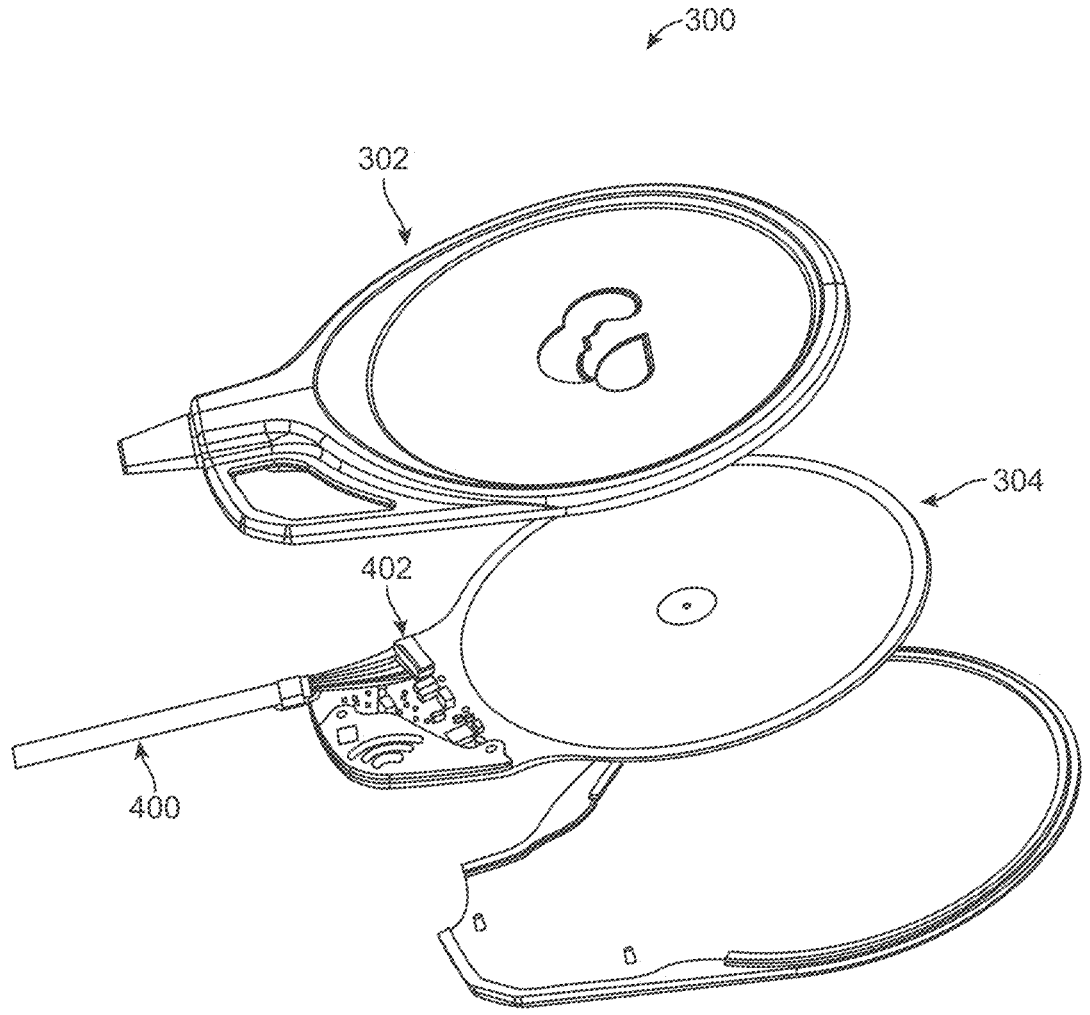
FIG. 9A is an exploded view of the programmer head of FIG. 3 and an integrated cable in accordance with principles of the present disclosure.
Figure 9B:
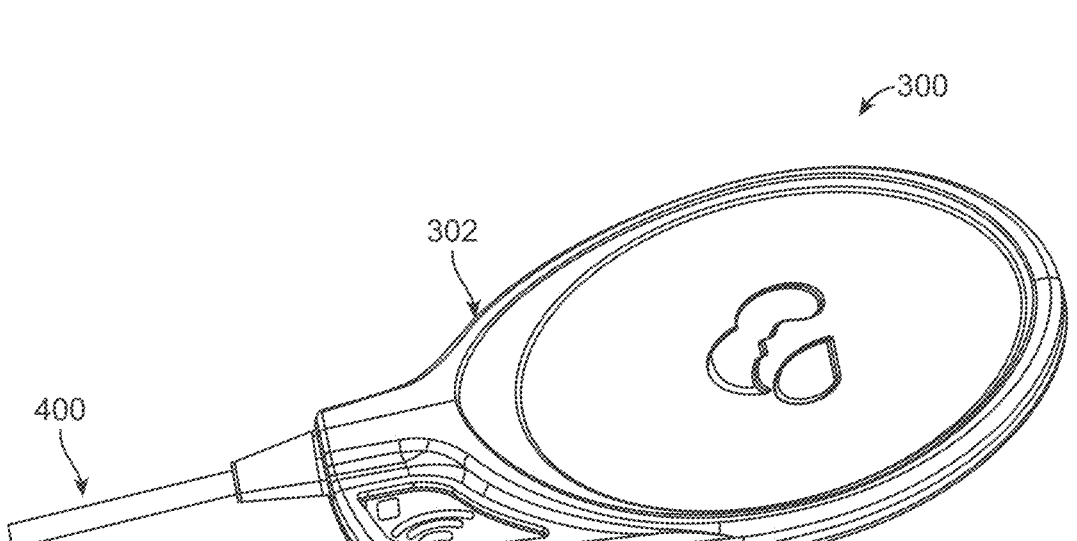
FIG. 9B is a perspective view of the programmer head and cable of FIG. 9A upon final assembly.

Returning to FIGS. 3 and 4, while the views implicate the programmer head 300 as being a component separable from the cable 154 (FIG. 1), in some embodiments, a cable can be permanently attached to, and extend from, the programmer head 300. For example, FIG. 9A illustrates one example of a cable 400 with wires electrically connected to an electrical port 402 component of the circuit board assembly 304. Upon final assembly, the housing 302 can be formed about the cable 400 in a manner impeding or prevent manual disconnection of the cable 400 from the programmer head 300 by a user, for example as shown in FIG. 9B. The cable 400 can assume various forms as described in greater detail below.

Figure 10:
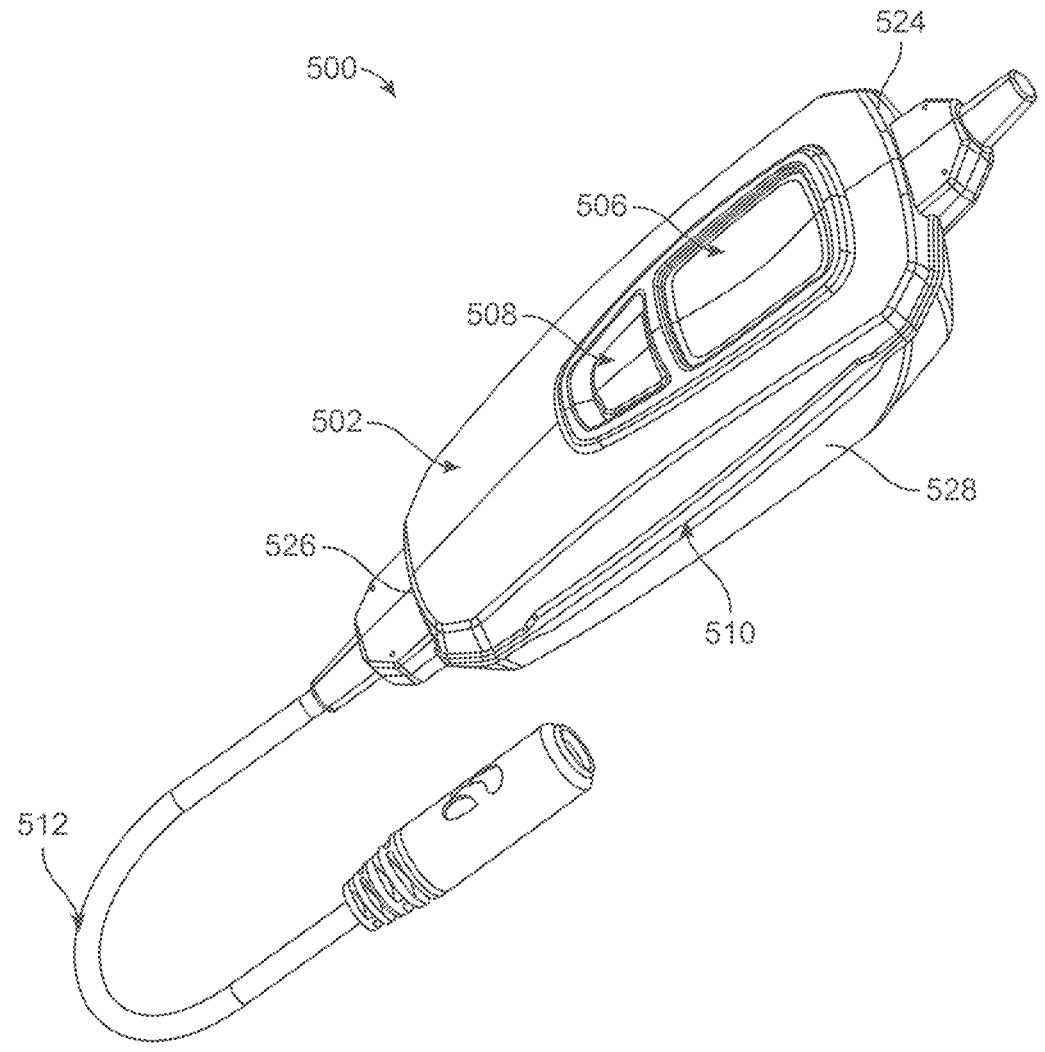
FIG. 10 is a perspective view of a controller useful with the wireless communications assembly of FIG. 1.
Figure 11:
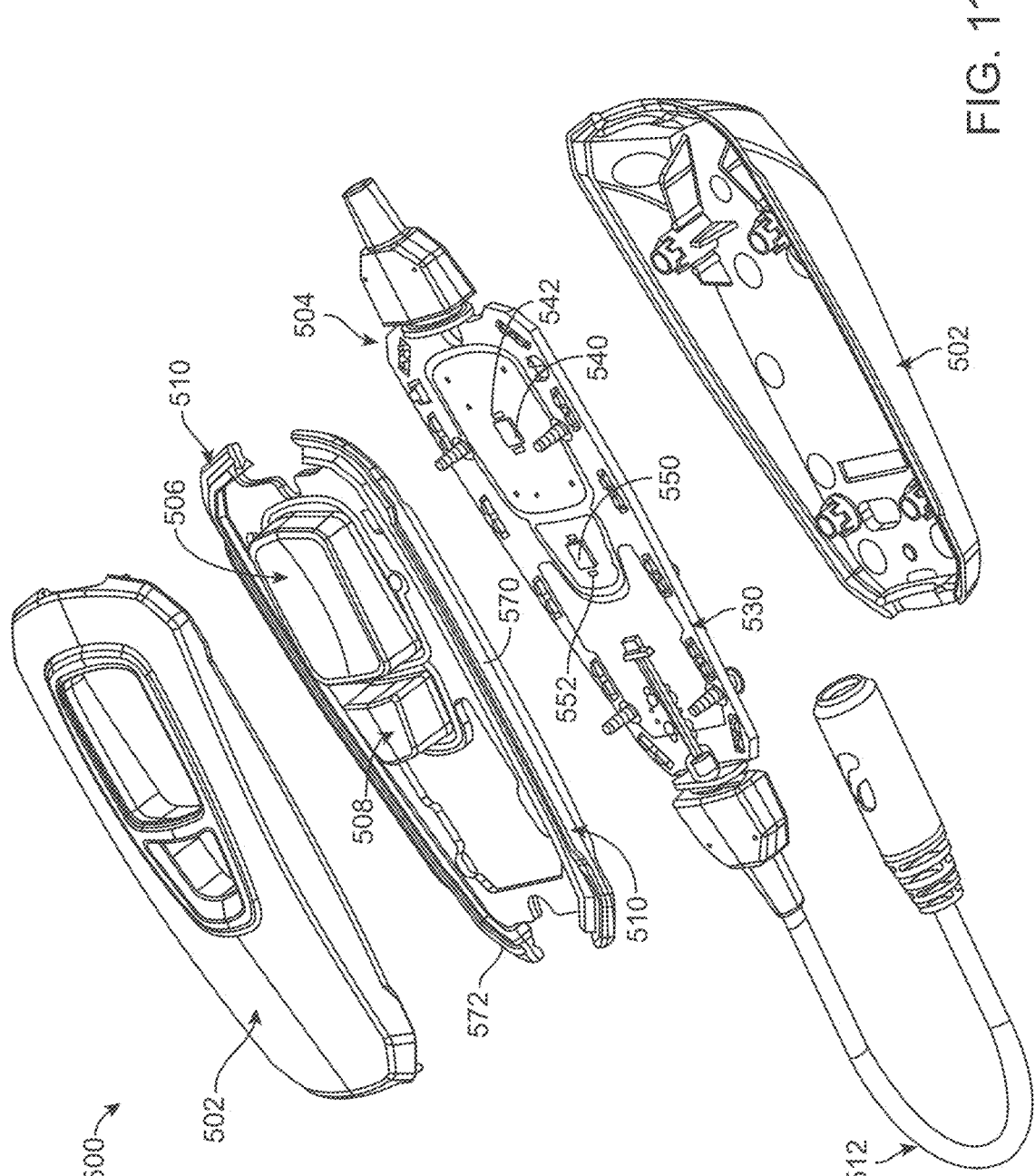
FIG. 11 is an exploded, perspective view of the controller of FIG. 10.

The programmer head 300 can provide benefits when combined with a variety of different controllers. One example of a controller 500 of the present disclosure (and useful, for example, as the controller 152 of FIG. 1) is shown in FIGS. 10 and 11. The controller 500 includes a case 502, a circuitry board assembly 504, a communication (e.g., telemetry) test button 506, an end therapy button 508, one or more status side lights 510, and a power cable 512. Details on the various components are provided below. In general terms, the circuitry board assembly 504 includes a processor and corresponding memory (e.g., embedded firmware) prompting operations of various features associated with the buttons and side lights 506, 508, 510. For example, in some non-limiting embodiments, the communication test button 506 can be operated by a clinician to prompt testing of telemetry connection between the programmer head 150

(FIG. 1) and the IMD 104 (FIG. 1). The end therapy button 508 can be operated by a clinician to prompt the IMD 104 to immediately discontinue delivery of therapy. The status side light(s) 510 can be operated to provide a clinician with a visual indication of various operational states, such as powering of the controller 500, pairing with the programmer 102 (FIG. 1), error states, etc. One or more visual indication features (e.g., lights) can similarly be provided with the one or both of the test button 506 and the end therapy button 508. Further, the controller 500 can be configured to provide a night mode of operation in which various light emitting elements of the controller 500 formatted to emit visible light are dimmed or powered off, and/or light emitting elements of the controller 500 formatted to emit infrared light (or other wavelength not visible to the human eye) are activated. Finally, the power cable 512 is electrically connected to the circuit board assembly 504, and is formatted for electrical connection to a power source or supply.

The case 502 can assume various forms appropriate for maintaining the components 504-512, and is generally sized and shaped for ergonomic handling. In some embodiments, a shape of the case 502 can be viewed as defining a top 520, a bottom (hidden in FIG. 10), a front 524, a back 526, and opposing sides 528 (one of which is visible in FIG. 10).

The circuit board assembly 504 can be, or can be akin to, a printed circuit board assembly (PCBA) or a flex circuit, and generally includes a base 530 (e.g., single or multi-layer board or film) supporting various electronic or electrical components and forming or supporting circuitry traces connecting to various ones of the electronic components. In some embodiments, the electronic components provided with the circuit board assembly 504 can include a processor (e.g., a microprocessor, embedded controller, etc.) coupled to one or more memories. The processor is configured to execute program code stored as software in the memory to implement various controller functions described herein.

In some embodiments, the electrical components provided with the circuit board assembly 504 can include wireless transceiver components to establish a Bluetooth® communication link and to establish a Wi-Fi® communication link. Thus, in some non-limiting examples, the controller 500 can be configured to wirelessly interface with a programmer (e.g., the programmer 106 of FIG. 1) via Bluetooth® or via Wi-Fi®. In other embodiments, only a single wireless communications format can be enabled with the controller 500, such as Bluetooth®, Wi-Fi, or other short range RF communication link format.

In some embodiments, the electrical components provided with the circuit board assembly 504 can include electrical links (e.g., circuitry traces) for transferring signals to and from the programmer head 150 (FIG. 1), 300 (FIG. 3). For example, and with embodiments in which the programmer head is akin to the programmer head 300 (FIG. 3) described above, the circuit board assembly 504 can be configured or programmed to receive signals from the programmer head's antenna (e.g., via the cable 154 (FIG. 1)) that can in turn be transmitted to the programmer 106 (FIG. 1) and/or directly acted upon by the controller 500. Further, the circuit board assembly 504 can be configured or programmed to transmit (e.g., via the cable 154) control signals received from the programmer 106 to the programmer head's antenna (e.g., control signals relating to operation of the IMD 104 (FIG. 1) otherwise in wireless communication with the programmer head 300) and/or to independently generate and deliver control signals to programmer head's antenna.

The communication test button 506 is maintained by the case 502 to be accessible by a user at the top 520 thereof, in a manner permitting a user (e.g., clinician) to press down on the communications test button 506 when desired (e.g., the communication test button 506 can be spring-loaded relative to the case 502). The circuit board assembly 504 can include one or more electronic components that are associated with the communication test button 506. For example, a sensor 540 (e.g., pressure sensor pad) can be provided that senses a pressing or other actuation-type force being applied to the communication test button 506. In response to sensed actuation of the communication test button 506, the controller 500 is configured (e.g., via embedded software) to perform a telemetry test operation. In some non-limiting examples in which the controller 500 is connected to the programmer head 300 (FIG. 3) and thus receives signals therefrom (including signals from the programmer head's antenna), the telemetry test operation can include the controller 500 reviewing or polling a telemetry-related signal being received at the programmer head's antenna responsive to attempted wireless communication with the IMD 104 (FIG. 1). Based upon a strength of the telemetry-related signal, the controller 500 can prompt the programmer head 300 to generate the corresponding signal strength icon display as described above (e.g., as in FIGS. 7A-7C). The telemetry test operation can be programmed to run continuously for a predetermined length of time (e.g., 30 seconds), affording the clinician the ability to reposition the programmer head 300 relative to the patient in order to attain a "strong" communication link. In some embodiments, the controller 500 can be programmed to allow a user/clinician to cancel a prompted telemetry test operation (e.g., prior to the conclusion of the predetermined length of time), for example in response to user actuation/pressing of the communications test button 506). Notably, this telemetry test operation can be performed by a clinician solely by interfacing with the controller 500; that is to say, while telemetry testing may also be initiated at the programmer 106 (FIG. 1), in some embodiments the controller 500 facilitates telemetry testing without the need for the programmer 106.

In some embodiments, the circuit board assembly 504 can include one or more LEDs 542 (referenced generally) or other light emitting device format at a location of the communication test button 506. The communication test button 506 can, in turn, incorporate features that generate an icon display when illuminated by the LED(s) 542 as described in greater detail below.

The end therapy button 508 is maintained by the case 502 to be accessible by a user at the top 520 thereof, in a manner permitting a user (e.g., clinician) to press down on the end therapy button 508 when desired (e.g., the end therapy button 508 can be spring-loaded relative to the case 502). The circuit board assembly 504 can include one or more electronic components that are associated with the end therapy button 508. For example, a sensor 550 (e.g., pressure sensor pad) can be provided that senses a pressing or other actuation-type force being applied to the end therapy button 508. In response to sensed actuation of the end therapy button 508, the controller 500 is configured (e.g., via embedded software) to perform an end therapy operation. In some non-limiting examples, the end therapy operation can include the controller 500 signaling or instructing the IMD 104 (FIG. 1), via the programmer head 150 (FIG. 1), to discontinue the delivery of any therapy (e.g., stimulation therapy).

In some embodiments, the circuit board assembly 504 can include one or more LEDs 552 (referenced generally) or other light emitting device format at a location of the end therapy button 508. The end therapy button 508 can, in turn, incorporate features that generate an icon display when illuminated by the LED(s) 552 as described in greater detail below.

Figure 12:
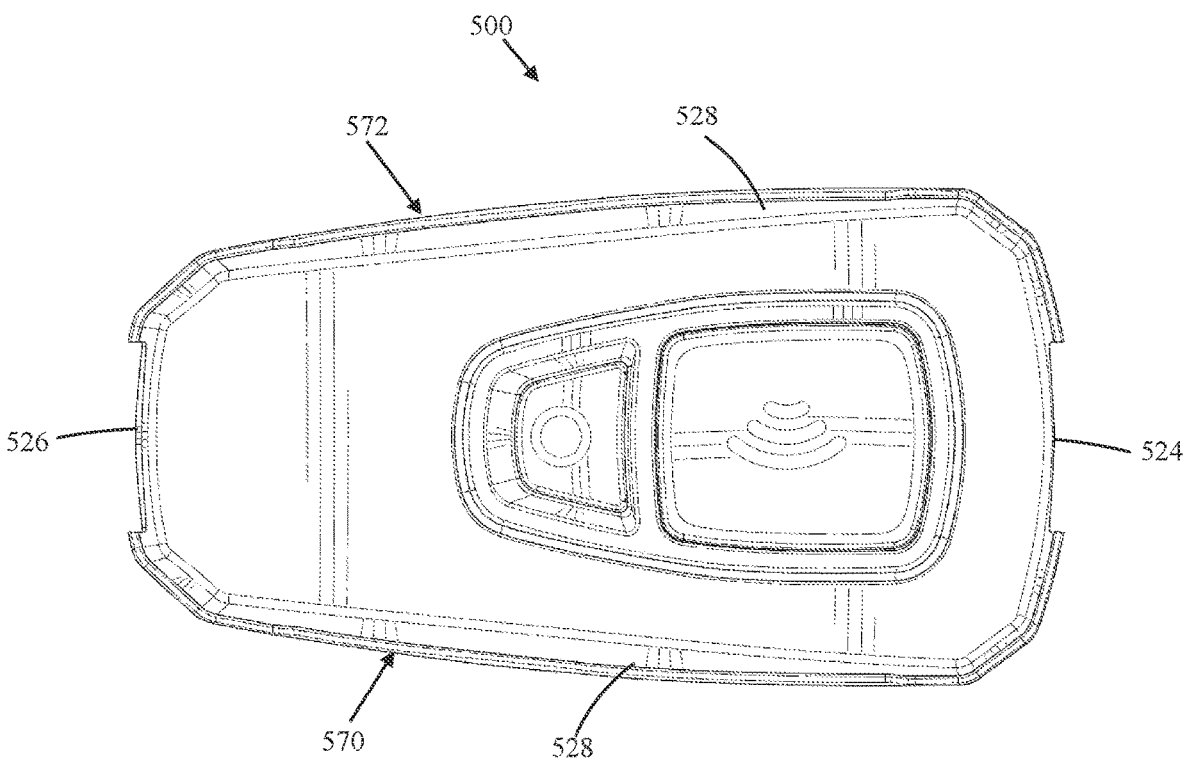
FIG. 12 is a top plan view of the controller of FIG. 10.

The status side light(s) 510 can assume various forms, and in some embodiments include first and second light assemblies 570, 572 (best seen in FIG. 11). The first and second light assemblies 570, 572 can be assembled to the opposing sides 528, respectively, of the case 502, and each includes a transparent or semi-transparent housing maintaining various light emitting devices (not shown). One non-limiting example of an arrangement of the light assemblies 570, 572 relative to the case 502 is provided in FIG. 12. As shown, the light assemblies 570, 572 can each extend along the corresponding side 528 to and along at least a portion of the front 524 and the back 526 in some embodiments. Other formats are also acceptable. Regardless, and returning to FIGS. 10 and 11, the light emitting devices associated with each of the light assemblies 570, 572 can be controlled by the circuit board assembly 504, and can include, for example, one or more LEDs (or the like) formatted to emit a first visible color of light, one or more LEDs (or the like) formatted to emit a second visible color of light differing from the first color, and one or more LEDs (or the like) formatted to emit infrared light (or other wavelength not in the visible spectrum) for reasons made clear below. Other light emitting device constructions can be employed with alternative embodiments.

Figure 13:
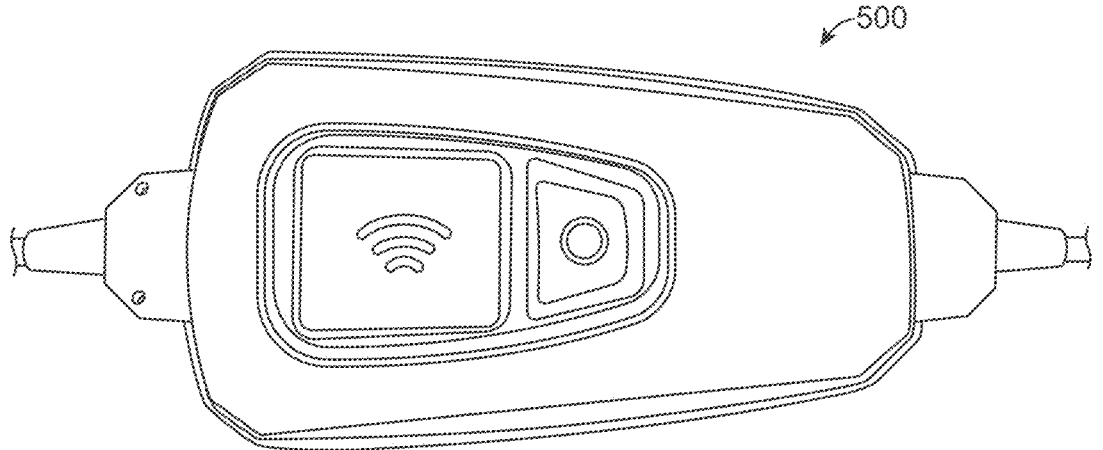
FIG. 13 illustrates a powered off state of the controller of FIG. 10.
Figure 14A:
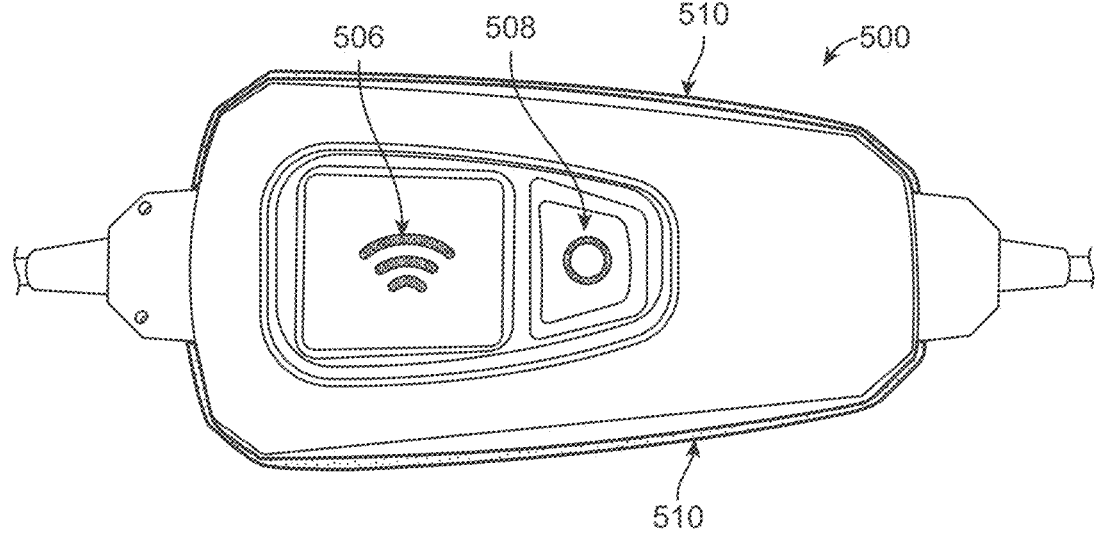
FIGS. 14A and 14B illustrate example normal mode indicators available with controller of FIG. 10, for example a powered on, connected state.
Figure 14B:
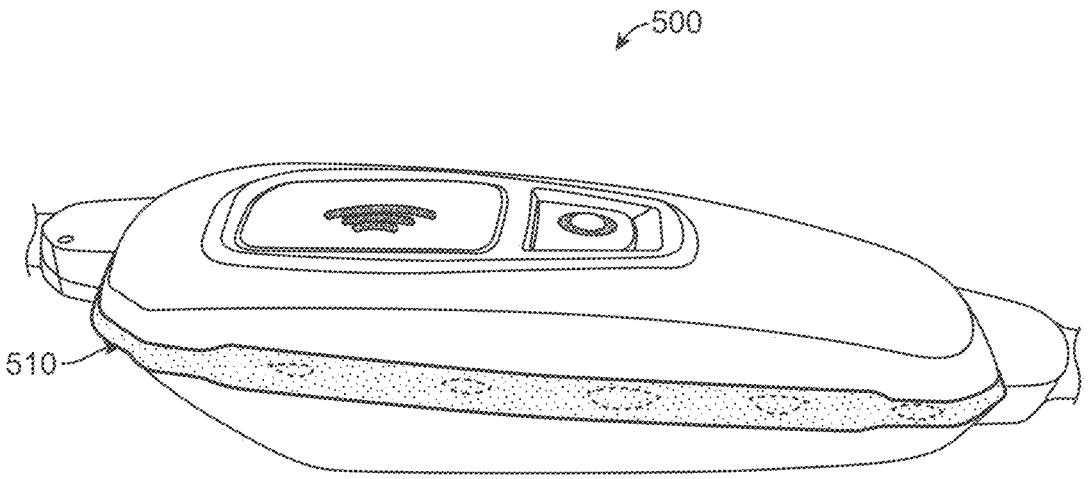

As implicated by the above discussions, the controller 500 can be configured to communicate various operational states or statuses to a clinician with lighted indicators relating to one or more of the controller 500, the programmer head connected thereto (e.g., the programmer head 300 of FIG. 3) and/or the programmer 102 (FIG. 1). By way of non-limiting example, FIG. 13 depicts the controller 500 in a "powered off" state in which not none of the lighted indicators are energized. FIG. 14A depicts a "powered on, connected" state in which the controller 500 and the programmer head 300 have been powered on and the controller 500 is wirelessly linked to the programmer 106. As shown, the powered on, connected state can include the status side lights 510 emitting a visible blue light, the communications test button 506 emitting a blue colored icon (e.g., three curved bars of decreasing size), and the end therapy button 508 emitting a white (or other color) ring-like icon. Other icons are also acceptable. FIG. 14B further highlights that in the powered on, connected state, the status side lights 510 provide a markedly visible indication to the clinician that the controller 500 is functioning as expected.

Figure 15A:
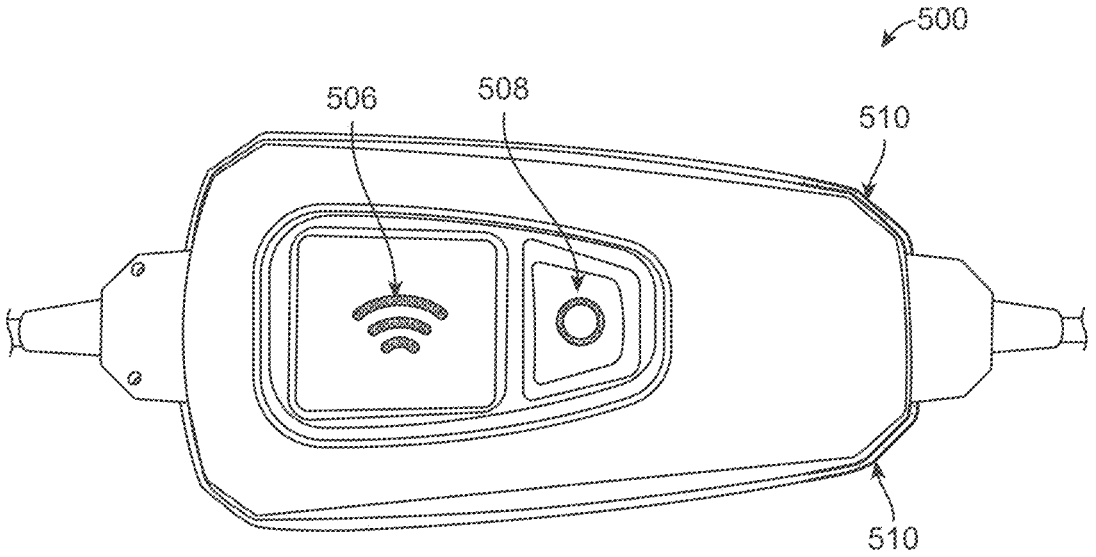
FIGS. 15A and 15B illustrate a powered on, disconnected state available with the controller of FIG. 10.
Figure 15B:
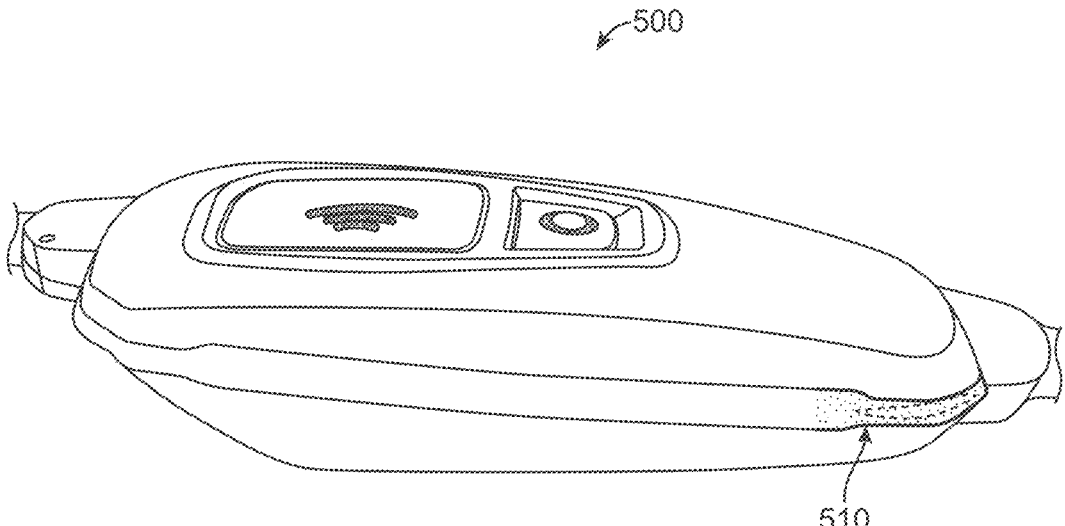

When, for example, the controller 500 is powered on and determines that a wireless link with the programmer 106 (FIG. 1) has not been established, the controller 500 can be configured to operate in a "powered on, disconnected" state, one example of which is shown in FIGS. 15A and 15B. As shown, the powered on, disconnected state can include only a portion of the status side lights 510 emitting a visible (e.g., blue) light (e.g., wherein the status side lights 510 each include a number of LEDs, in the powered on, disconnected state, one a single one of the LEDs is energized). A comparison of FIGS. 15A and 15B with FIGS. 14A and 14B illustrates that a user is readily apprised of a difference between the powered on, connected state (FIGS. 14A and 14B) and the powered on, disconnected state (FIGS. 15A and 15B).

Figure 16:
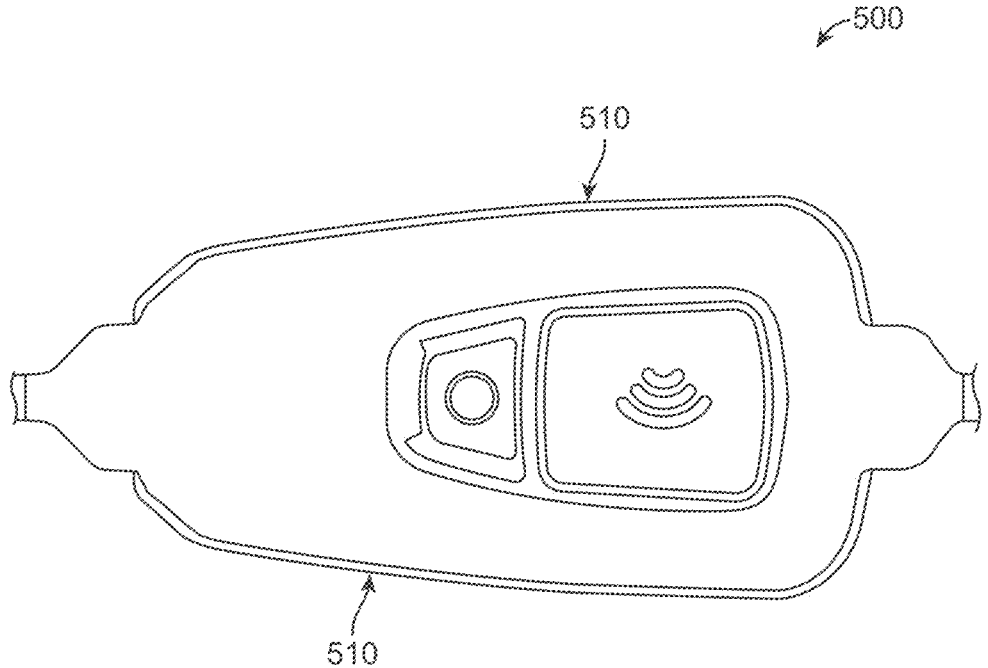
FIG. 16 illustrates an example error mode indicators available with the controller of FIG. 10.

When, for example, the controller 500 detects an error (optionally when prompted the programmer 106 (FIG. 1) in response to a determined error), the controller 500 can be configured to cause the side status lights 510 to emit a different, visible color, for example as represented by FIG. 16. The "error" mode can include the status side lights emitting a visible orange light (or other color differing from a color of the normal powered on state shown and described with respect to FIGS. 14A and 14B). For example, the controller 500 can be programmed to operate in the error mode if a critical error (e.g., an error that prevents the controller 500 or other component of the wireless interface assembly from operating reliably and can be based on implementation decisions) is detected, such as failure of a power-on self-test performed by the controller 500, corrupt application image or data, etc.

The controller 500 can further be configured to operate in a "night" mode. As a point of reference, full lighting from the controller 500 during, for example, a sleep study (in which the patient is residing in an otherwise darkened room), may undesirably disrupt or negatively affect a patient's sleep. With this in mind, in some embodiments, the night mode of operation of the controller 500 can include dimming of all light emitting devices. In other embodiments, the night mode of operation can include disabling power to all light emitting devices of the controller 500 that otherwise emit light in the visible wavelength, and energizing light emitting devices of the controller 500 that emit light in the non-visible wavelength. For example, and as mentioned above, the side status lights 510 can each include one or more infrared LEDs. In the night mode of operation, the infrared LEDs are energized, allowing the system state to be monitored remotely using an infrared camera. The night mode can be initiated, for example, at the programmer 106 (FIG. 1) in some embodiments. In some embodiments, the night mode of operation can further include one or more of the visible light LEDs carried by the controller 500 briefly turning on (e.g., dimmed or at lower brightness or intensity as compared to the powered on states described above) in response to sensed actuation of the communication test button 506 and/or the end therapy button 508. Under these circumstances (where one of the buttons 506, 508 has been pressed while in the night mode), it is understood that the clinician is present and interfacing with the controller 500; the brief lighting of the controller 500 serves as a visual response to the clinician confirming that the controller 500 is active.

The controller 500 can optionally be configured or programmed to provide one or more additional operational features. For example, in some embodiments, the controller 500 can be programmed to initiate a pairing operation in which the controller 500 attempts to wireless link or pair with another device (e.g., the programmer 106 (FIG. 1)) in response to a clinician prompt. In some non-limiting examples, the pairing operation can be initiated by the user holding down the communication test button 506 for several seconds while connecting the controller 500 to power.

The controller 500 can be useful with a number of different programmer head configurations, for example, but not limited to, the programmer head 300 (FIG. 3).

Figure 17:
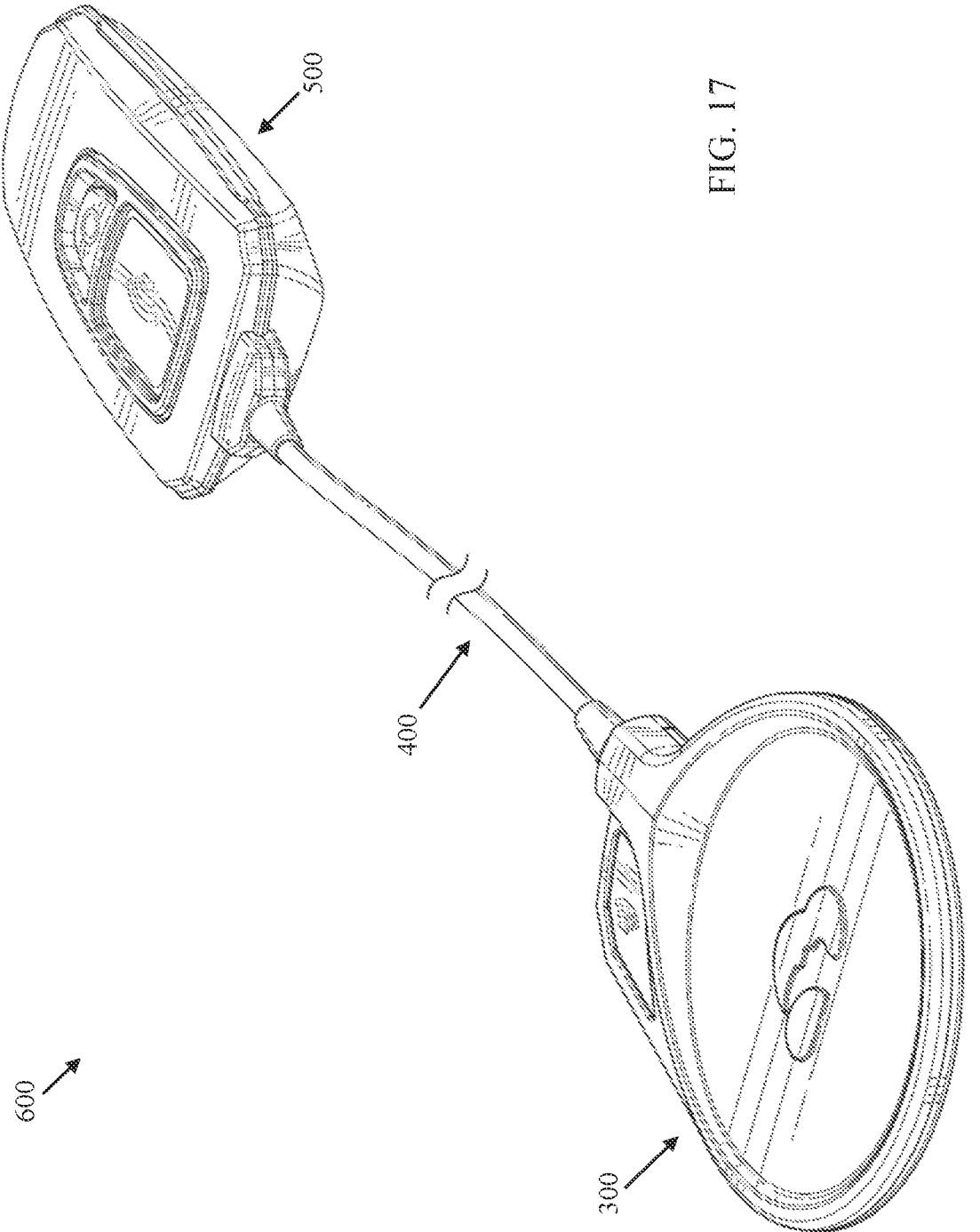
FIG. 17 is a perspective view of a wireless communications assembly in accordance with principles of the present disclosure, including the programmer head of FIG. 3, the controller of FIG. 10, and a cable.

Returning to FIG. 1, the cable 154 can assume various forms appropriate for establishing and maintaining an electrical connection between the programmer head 150 and the controller 152. In some embodiments, the cable 154 can be permanently assembled to the programmer head 150 and the controller 152. FIG. 17 illustrates one non-limiting example of the programmer head 300 and the controller 500 as described above, interconnected by the cable 400 to provide a wireless interface assembly 600 in accordance with principles of the present disclosure. The cable 400 is configured to deliver electrical signals between the programmer head 300 and the controller 500, as well as to, in some embodiments, deliver power from the controller 500 to the programmer head 300. The cable 400 is generally flexible and in some embodiments can have a length of at least five feet, and in some embodiments a length on the order of six feet. Other lengths are also acceptable. With optional embodiments in which the cable 400 has a length of at least five feet, the controller 500 can be positioned well away from the programmer head 300. This can be beneficial, for example, when the wireless interface assembly 600 is employed in connection with a sleep study; by locating the controller 500 away from the programmer head 300 (e.g., the programmer head 300 is lying on the patient whereas the controller 500 is placed on the floor), the controller 500 will be well away from the patient (meaning the patient will accidentally come into contact with the controller 500).

The wireless communication assemblies (or programmer cables) of the present disclosure provide a marked improvement over previous designs. For example, in some embodiments the wireless communication assembly includes a programmer head interconnected to a controller by a cable, with the programmer head configured to facilitate wireless communication (e.g., telemetry) with an implanted IMD and the controller configured to wirelessly communicate with a clinical programmer. The programmer head can include a flat, low profile housing that is more comfortable when placed onto a patient. An optional strength display provided with the programmer head can include wireless communications strength gauge LED indicators for indicating optimal placement relative to an IPG or IMD. An optional EMI display provided with the programmer head can indicate when electrical noise is disturbing telemetry communications with an IMD. An optional test connection button provided with the controller can provide users with a conventional method to optimize the position of the controller head and confirm that telemetry communications with the IMD is successful. An optional therapy off button provided with the controller can allow a user to immediately turn off the delivery of stimulation therapy by the IMD. Optional indicator lights provided with the controller give feedback to a user, for example communicating success/failure of button presses and wireless connection status. In this regard, different colors and/or light intensity can be implemented by the indicator lights to inform a user if the wireless communication assembly is (1) not connected, (2) connected to the programmer, and/or (3) an error has occurred. In some embodiments, infrared LEDs are included to communicate connection status in a darkened environment (such as a sleep lab setting). The controller can be configured to provide a "pairing mode" by holding down a button while power cycling the assembly. Dedicated lighting feedback can be employed to inform a user when the paired state is entered. In some embodiments, the cable can have an increased length as compared to previous designs, for example on the order of 6 feet.

In some examples, the IMD 104 and/or programmer 106 in at least some of the examples described in association with at least FIGS. 1-17 may comprise at least some of substantially the same features as, and/or example implementations of, the IMD 1104 (and/or IMD 1134) and programmer 1102 as described in association with at least FIGS. 18-32B.

In some examples, the IMD 1104 (and/or IMD 1134) and/or programmer 1102 in at least some of the examples described in association with at least FIGS. 18-32B may comprise at least some of substantially the same features as, and/or example implementations of, the IMD 104 and programmer 106 as described in association with at least FIGS. 1-17.

At least some examples of the present disclosure are directed to a method and/or apparatus to program an implantable medical device (IMD), such as an implantable pulse generator (IPG). In some such examples, the IMD may already be implanted within a patient and the programming may include programming therapy stimulation settings, such as stimulation strength, pulse profile, and the like. In some examples, the programming may comprise adjusting timing settings such as start delay, pause duration, therapy duration (e.g. 8 hours), and the like. Other programmable stimulation parameters are further described later.

At least some example methods may comprise various types of stimulation programming and/or evaluation, such as for an initial activation of a recently implanted IPG, a follow-up visit by the patient to the clinician, a sleep study evaluation of therapy effectiveness, and the like. It will be understood that, in at least some examples, a method of stimulation programming may include evaluation aspects as part of performing stimulation programming. In some examples, the example stimulation programming methods may sometimes be referred to as a clinician programming method, a workflow, or a protocol. It will be understood that the term clinician may refer to a device therapy technician, sleep study technician, a physician, or other medical worker (e.g. health care personnel) suitably experienced to conduct (or assist with) the example methods.

In some examples, at least some aspects of, or related to, the example stimulation programming methods may be displayed and operable via a user interface (e.g. graphical user interface), such as on a mobile computing tablet (or other convenient mobile computing device) which is capable of communicating with the implantable medical device directly or indirectly via an intermediary communication device or element.

Via at least some of these example methods, a clinician may be guided to efficiently and effectively program (and/or evaluate) an IMD according to desired and/or recommended stimulation therapy parameters without extensive training particular to the IMD and/or particular to the programmer. Moreover, in some such examples, while the example methods help guide the clinician through the programming, the example methods still provide the clinician with appropriate autonomy in making medical decisions and/or using their discretion as appropriate regarding adjustment of parameters of the programmer, IMD, etc.

These examples, and additional examples, are described in association with at least FIGS. 18-32B.

Figures 18, 19, 20:
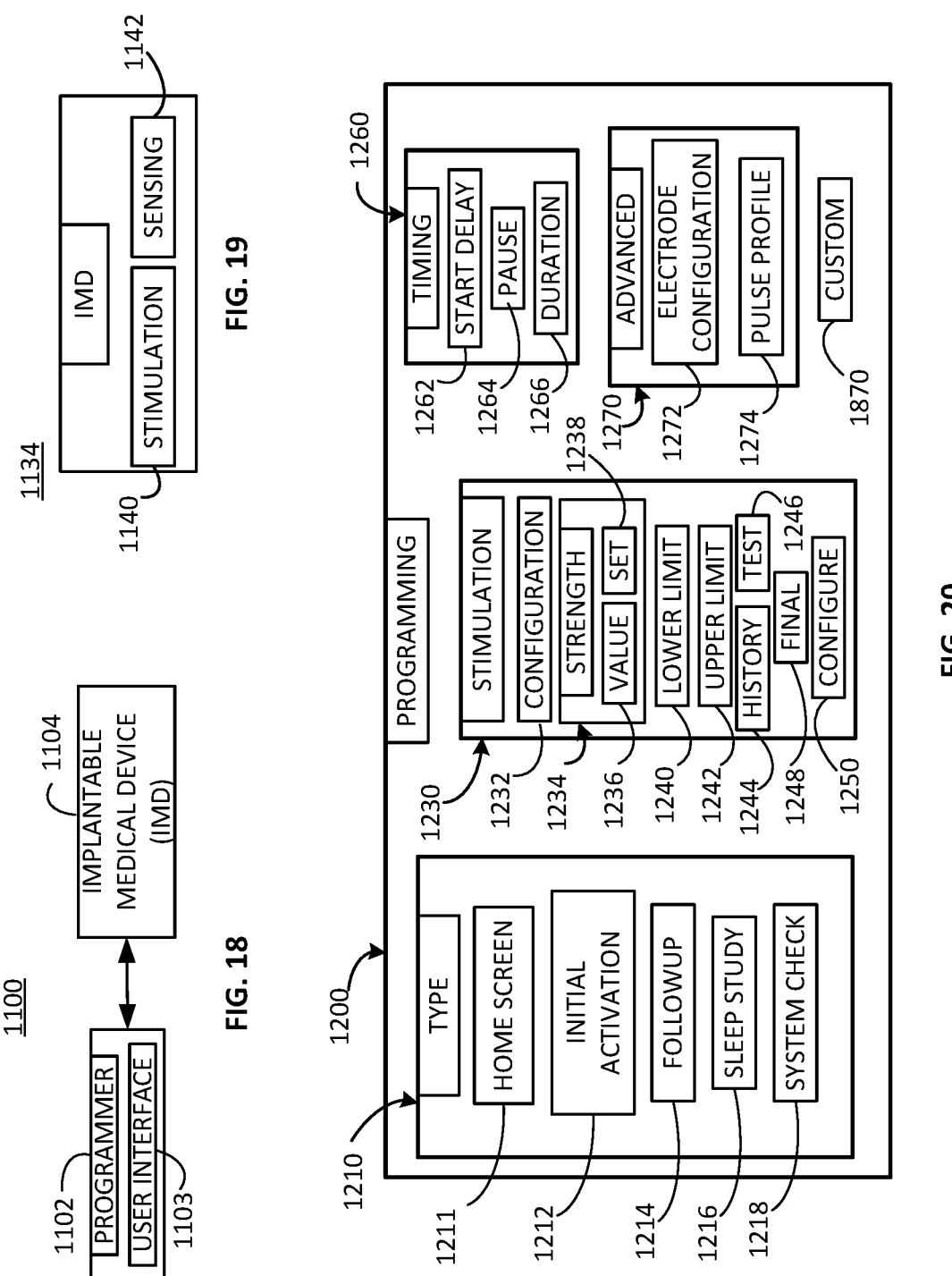
FIG. 18 is a block diagram schematically representing an example arrangement including a programmer and an implantable medical device.
FIG. 19 is a block diagram schematically representing an example implantable medical device.
FIG. 20 is a block diagram schematically representing an example stimulation programming engine.

As shown in FIG. 18, one example arrangement (e.g. system) 1100 comprises an implantable medical device (IMD) 1104 and a programmer 1102. In some examples, the IMD 1104 may comprise an implantable pulse generator (IPG), which in some examples may comprise an IPG for treating sleep disordered breathing (SDB) and/or other patient conditions (e.g. cardiac, pelvic disorders, etc.). The programmer 1102 may communicate with the IMD 1104 via a wireless communication protocol either directly or indirectly via an intermediary communication element (e.g. antenna, other). However, depending on the type and/or placement of the IMD 1104, the programmer 1102 may communicate with the IMD 1104 via a wired connection. The programmer 1102 may sometimes be referred to as a clinician programmer to the extent that the programmer 1102 is expected to be employed via a clinician.

In some examples, the programmer 1102 comprises a user interface 1103, such as but not limited to, a graphical user interface (GUI) to facilitate display and input relative to the example methods by which a clinician operates the programmer 1102 and/or performs the example methods. It will be further understood that the programmer 1102 may perform tasks or operations (relating to patient care, maintenance) etc. other than programming stimulation-related aspects of the IMD 1104. Moreover, in some examples, the programmer 1102 may comprise a device dedicated solely for the purpose of communicating with, programming, etc. the IMD 1104.

However, in some examples, the programmer 1102 may comprise a non-dedicated device which may be used for purposes (e.g. general communication, general computing, etc.) other than communicating with or, programming the IMD 1104. In some such examples, the programmer 1102 may comprise a consumer device, such as a consumer tablet, smart phone, etc. which is also operable via secure modes/communications/paths to communicate with, program, etc. the IMD 1104.

The user interface 1103 may comprise one example implementation of, and/or comprise at least some of the features and attributes of, the user interface 2440 described later in association with at least FIGS. 32A-32B. Accordingly, it will be further understood that the programmer 1102 (including user interface 1103) and/or IMD 1104 may comprise a control portion, or comprise an example implementation of one part of a control portion, like control portion 2400 as later described in association with at least FIGS. 32A-32B. Moreover, various example implementations of user interface 1103, 2440 are described and illustrated throughout the below-described examples of the present disclosure in association with at least FIGS. 21-31.

FIG. 19 is a block diagram schematically representing an example IMD 1134, which may comprise one example implementation of IMD 1104. In some examples, IMD 1134 comprises a stimulation component 1140 and sensing component 1142. In some examples, the stimulation component 1140 comprises a stimulation engine to generate a stimulation signal to be applied to a tissue (e.g., nerve, muscle, etc.). In the examples in which the IMD 1134 comprises an implantable pulse generator (IPG), the tissue to be stimulated may comprise tissue to maintain or restore upper airway patency, such as but not limited to a hypoglossal nerve, an ansa cervicalis-related nerve and/or other nerves, etc. In some such examples, the stimulation component 1140 also may comprise circuitry for generating and delivering the stimulation signal. In some examples, the stimulation component 1140 of the IMD 1134 also may comprise a stimulation element, such as an electrode configuration(s) through which the stimulation signal may be applied to the target tissue.

In some examples, the sensing component 1142 comprises a sensing engine to receive a sensing signal obtained relative to a tissue (e.g., muscle, organ, etc.). In the examples in which the IMD 1134 comprises an IPG for treating sleep disordered breathing (SDB), the tissue to be sensed may be related to respiration, oxygenation, cardiac functions, upper airway patency, and the like. In some such examples, the sensing component 1142 also may comprise circuitry for receiving and processing the sensing signal. In some examples, the sensing component 1142 of the IMD 1134 also may comprise a sensing element, such as an electrode or other element through which the sensing signal is obtained. Of course, in contexts in which the IMD 1104, 1134 relates to bodily organs, functions, etc. other than sleep disordered breathing, the stimulation component 1140 and sensing component 1142 would be deployed relative to other tissues. For instance, the IMD 1104, 1134 may be deployed to treat pelvic disorders, such as stress incontinence or other conditions, with applicable tissues including the bladder, pudendal nerve, urinary and/or anal sphincters and the like.

In some examples, the stimulation component 1140 and/or sensing component 1142 may be on-board the IMD 1134, which in some examples may comprise a microstimulator. In some examples, at least a portion of the stimulation component 1140 and/or sensing component 1142 may be separate from, and independent of, a housing of the IMD 1104, 1134 with one or both components 1140, 1142 being in wired or wireless communication with the IMD 1104, 1134.

As shown in FIG. 20, in some examples a stimulation programming engine 1200 may control, direct, etc. programming an IMD 1104, 1134 to deliver stimulation to a tissue, such as but not limited to tissue which may maintain or restore upper airway patency to treat sleep disordered breathing (SDB). However, it will be understood that in some examples, at least some parameters of engine 1200 may be applicable for stimulation programming (and/or evaluation) with regard to other tissues, such as pelvic tissue, the stimulation of which may alleviate or ameliorate pelvic disorders, including but not limited to incontinence (e.g. stress incontinence, other). It will be understood that once determined via the assistance of a programmer, such stimulation programming (and related settings) is used to configure the IMD 1104, 1134 such that the stimulation programming settings become stored within, and are implemented via the IMD 1104, 1134 to deliver and manage therapy to the patient.

With further reference to FIG. 20, in some examples the stimulation programming engine 1200 comprises a programming type engine 1210, a stimulation settings engine 1230, a timing settings engine 1260, and advanced settings engine 1270. In some examples, all or some of the features of the stimulation programming engine 1200 may be implemented via, and/or as part of, control portion 2400 as later described in FIG. 32A. Moreover, it will be understood that features and aspects of the programming engine 1200 are not strictly limited to the engines 1210, 1230, 1260, and/or 1270.

In some examples, the programming type engine 1210 may control, direct, support, display, etc. methods to provide for, and guide, stimulation programming and/or related tasks, operations, etc. As further shown in FIG. 20, in some examples, the programming type engine 1210 comprises engines for providing and performing a method of stimulation programming and/or evaluation relative to a home screen 1211, an initial activation 1212, a follow-up visit 1214, and/or a sleep study 1216. In some examples, the programming type engine 1210 also may comprise an engine for providing a method for performing a system check 1218.

Figure 21:
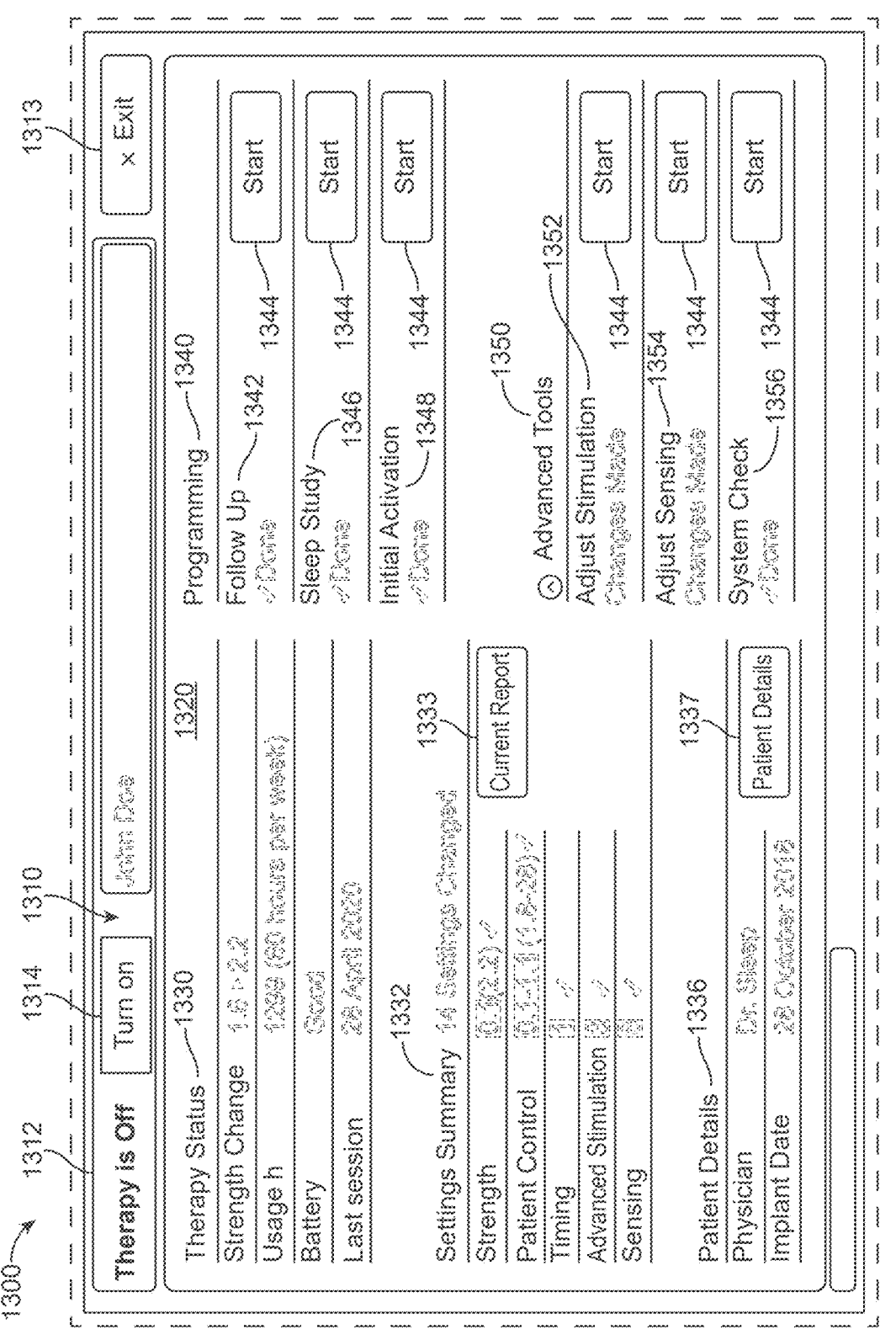
FIG. 21 is a diagram schematically representing an example home screen user interface.

In general terms, the home screen engine 1211 is to provide a tool and/or method by which a clinician, via a user interface 1103, may start, end, or otherwise manage the various programming methods in association with engines 1212, 1214, 1216, 1218, as well as perform other general tasks and operations related to providing care (e.g. therapy, etc.) for the patient. As further described later, FIG. 21 provides one example home screen user interface 1300.

In some examples, via the user interface 1103, the initial activation engine 1212 in FIG. 20 is to provide a tool and/or method by which a clinician may initially program the IMD 1104, 1134 to provide therapeutic stimulation for the patient.

In some such examples, this initial programming may occur at a recommended period of time after surgical implantation of the IMD 1104, 1134. One example implementation of the initial activation programming engine 1212 may be implemented according to at least some of features of the method of initial activation programming in association with at least FIG. 22.

In some examples, via the user interface 1103, the follow-up engine 1214 is to provide a tool and/or method by which a clinician may assess and/or adjust a current programing configuration of the IMD 1104, 1134 to provide therapeutic stimulation for the patient. In some such examples, this follow-up assessment may occur at a recommended period of time after the initial activation (per engine 1212) of the IMD 1104, 1134. One example implementation of the follow-up engine 1214 may be implemented according to at least some of features of the example methods in FIGS. 25A-28C. In particular, FIGS. 25A-25B address an example basic follow-up method and related user interface while FIGS. 26-28C address example advanced follow-up method(s) and related user interfaces.

In some examples, via the user interface 1103, the sleep study engine 1216 is to provide a tool and/or method by which a clinician may assess and/or adjust a current programing configuration of the IMD 1104, 1134 during a sleep study. In some such examples, this sleep study assessment may occur at a recommended intervals sometime after an initial device activation, follow-up, etc. or may occur at any time it is desired to evaluate the efficacy of the IMD 1104, 1134 and its programming. One example implementation of the sleep study engine 1216 may be implemented according to at least some of features of the example methods in FIGS. 29-30A and related user interfaces in association with at least FIGS. 30B-30C.

In some examples, via the user interface 1103 (FIG. 18), the system check engine 1218 in FIG. 20 is to provide a tool and/or method by which a clinician may assess and/or adjust various operations, parameters, system functions, etc. of the IMD 1104, 1134 to ensure or maintain desired operations of the IMD 1104, 1134. In some such examples, this system check may occur at a recommended intervals or may occur at any time it is desired to evaluate the operations of the IMD 1104, 1134 and its programming.

As further shown in FIG. 20, the stimulation settings engine 1230 (of the programming engine 1200) provides for tools, parameters, etc. to support the display on user interface 1103 in FIG. 18 of (and/or the performance of) the various programming methods supported by the engine 1210, timing settings engine 1260, and/or advanced settings engine 1270 of FIG. 20. These various tools, parameters, functions, parameters, etc. will be described generally with respect to FIG. 20-21 and at least some of these same tools, etc. will be further described in the context of at least some of the associated methods of stimulation programming described in association with at least FIGS. 22-31.

With further reference to FIG. 20, in some examples the stimulation settings engine 1230 comprises a configuration parameter 1232 corresponding to currently configured settings (e.g. stimulation strength, other) of the IMD 1104, 1134. In some examples, the current configuration settings of the IMD 1104, 1134 may comprise default settings programmed by the supplier (or manufacturer, distributor, etc.) of the IMD 1104, 1134 or programmed by the clinician prior to implant of the IMD 1104, 1134. Moreover, after each instance in which an IMD 1104, 1134 has its settings adjusted, such as via one of the stimulation programming methods (e.g. as driven by engines 1212, 1214, 1216, etc.)

displayable on user interface 1103, then via the later-described configure function 1250, the adjusted settings will become the new configuration settings (i.e. current configuration) of the IMD 1104, 1134. As further described later, in some examples, performing one of the example stimulation programming (and/or evaluation) methods does not necessarily result in changing already configured stimulation settings of an IMD.

Via the stimulation strength parameter 1234 of the stimulation settings engine 1230 and the user interface 1103 (FIG. 18), a clinician may select a value 1236 of the stimulation strength (e.g. amplitude, other) and one may implement setting this value in the IMD 1104, 1134 via the set function 1238. The stimulation settings engine 1230 also may comprise lower limit and upper limit parameters 1240, 1242 which set limits on stimulation strength values between which a patient may make their own adjustments to therapy stimulation strength, such as via a patient remote.

Via a history parameter 1244 (of the stimulation settings engine 1230) on user interface 1103, the programmer 1102 may record a history of the stimulation settings (and other settings such as timing) configured into IMD 1104, 1134. At least some of the later described example user interfaces provide a stimulation history function 1562.

With further reference to FIG. 20, via a test function 1246 (of stimulation programming engine 1230) on user interface 1103, a clinician may initiate and implement delivery (via the IMD 1104, 1134) of a test stimulation signal to the patient. Via a final parameter 1248 (of stimulation programming engine 1230), the programmer 1102 may store and maintain a final stimulation strength setting (e.g. amplitude, other) resulting from one of the respective example stimulation programming methods (e.g. per engines 1212, 1214, 1216, etc.). Via the configure parameter 1250, a clinician may cause (in some circumstances) the final stimulation setting 1248 to become the new configuration settings (i.e. 1232) in the IMD 1104, 1134 for on-going use by the patient during a therapy period. At least some of the later described example user interfaces display a final stimulation settings and/or timing settings, which are described below.

As further shown in FIG. 20, in some examples the timing settings engine 1260 (of the stimulation programming engine 1200) provides for display of, and/or operation of, parameters to control a start delay 1262 before stimulation starts during a sleep/therapy period, a pause 1264 in stimulation therapy, and/or a therapy duration 1266 (e.g. overnight during a sleep period). These parameters may be selected, adjusted, etc. in association with at least some of the example methods, or as one of the default settings of the IMD 1104, 1134. These parameters are further described later in association with at least FIGS. 25B, 28C, 30C.

As further shown in FIG. 20, in some examples the advanced settings engine 1270 (of the stimulation programming engine 1200) provides for display, and/or operation of, parameters to control electrode configuration via function 1272 (e.g. pattern, selection, location, etc. of electrode contacts), and/or control a pulse profile (e.g. pulse width/ rate, pulse shape, burst shape, etc.) function 1274 of the stimulation pulses. These parameters may be selected, adjusted, etc. in association with at least some of the example stimulation programming methods, etc. or as one of the default settings of the IMD 1104, 1134. However, in some examples, these advanced settings may be primarily accessed via the advanced follow-up method of stimulation programming 1530, 1600, 1700 in association with at least FIGS. 26-28C.

As shown in FIG. 20, in some examples the stimulation programming engine 1200 may comprise a custom stimulation programming engine 1870, which provides for performing stimulation programming according to parameters instead of, and/or in addition to, at least some of the parameters, functions, etc. described in association with FIG. 20. One example implementation of the custom stimulation programming engine 1870 is further described later in association with at least FIG. 27F.

Additional details regarding the various engines, parameters, functions, etc. associated with, and/or comprising part of, the stimulation programming engine 1200 are further described in association with at least the example stimulation programming methods illustrated in FIGS. 24A-30C.

Moreover, it will be understood that via user interface 1103 (FIG. 18) on programmer 1102, the various stimulation programming methods described in association with at least FIGS. 24A-30C may comprise a general guide by which a clinician may perform stimulation programming, evaluate stimulation programming, etc. to influence therapy delivered via an IMD 1104, 1134 (e.g. IPG) and/or related components, systems, etc. For example, a clinician may choose to perform all or just some of the example stimulation programming methods, and the stimulation programming engine 1200 is arranged and implemented via user interface 1103 to permit the clinician to perform such programming methods (or portions thereof) in a desired order. In other words, in some examples the engine 1200 does not require that the multiple stimulation programming methods be performed in a pre-determined order during any given programming session. However, it will be understood that the stimulation programming engine 1200 (via engine 1210) in FIG. 20 may provide, via user interface 1103 (FIG. 18), for a recommended sequence of performing the various example stimulation programming methods and may guide the clinician's use between or among the different respective stimulation programming methods based on which stimulation programming methods have not yet been performed and/or already have been completed.

Figure 32A:
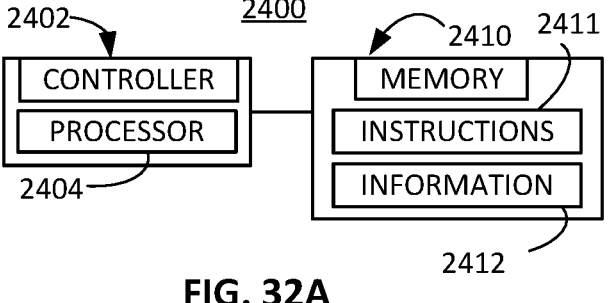
FIG. 32A is a block diagram of an example control portion.

As previously mentioned, the various stimulation programming methods may be implemented as part of, or in association with, a control portion such as control portion 2400 in FIG. 32A and user interface 1103 (FIG. 18), 2440 (FIG. 32B), respectively. For instance, a mobile computer such as a tablet may comprise at least a portion of the control portion 2400 and user interface 1103 in order to implement the example stimulation programming methods in a manner by which a clinician may be guided through a stimulation programming method while executing commands as part of the stimulation programming method, while also having the freedom and discretion to exercise at least some autonomy in implementing their medical judgment. In this regard, it will be further understood that the various aspects of the example stimulation programming methods shown in FIGS. 22-30C do not necessarily represent the entirety of activities which a clinician may perform via the example stimulation programming method(s), with some such activities being prompted via the user interface 1103 while some such activities may be initiated by the clinician (according to their general training, experience, etc.) in a manner complementary with the example stimulation programming methods.

FIG. 21 is diagram schematically representing an example home screen user interface 1300. As previously noted, this home screen user interface 1300 may be generated and operable via the home screen engine 1211 in FIG. 20. As shown in FIG. 21, the home screen user interface 1300 may comprise a banner 1310 which may comprise patient information, therapy off status indicator 1312, therapy "on" activation function 1314, as well as an exit function 1313. As further shown in FIG. 21, in some examples the home screen user interface 1300 comprises a main page 1320, which may include a therapy status portion 1330, a settings summary portion 1332, a patient details portion 1336, a programming portion 1340, and/or an advanced tools portion 1350.

As shown in FIG. 21, in some examples, the therapy status portion 1330 may display information such as (but not limited to) stimulation strength change, usage (in hours), batter status/health, date of last therapy session, and the like. Meanwhile, in some examples, the settings summary portion 1332 may display information such as (but not limited to) a value of the stimulation strength setting (e.g. Volts), a range of stimulation strength values selectable by the patient (i.e. patient control), timing settings status, advanced stimulation status, and/or sensing settings status. Via a current report function 1333, in some examples this information may be refreshed or accessed while in some examples, function 1333 may provide more information than shown in FIG. 21.

As shown in FIG. 21, the patient details portion 1336 may display information such as (but not limited to) physician identification, implant date, and the like. Via a patient details function 1337, in some examples this information may be refreshed or accessed, while in some examples the patient details function 1337 may provide additional information beyond that which is shown in FIG. 21.

As further shown in FIG. 21, the programming portion 1340 may display a status regarding, and/or permit activation of, a follow-up stimulation programming method 1342, a sleep study stimulation programming method 1346, and an initial activation stimulation programming method 1348. Each respective stimulation programming method may be activated via activating (e.g. finger touch or stylus) a start button 1344 associated with each stimulation programming method. While explained below in greater detail, in some examples at least some aspects of such programming methods comprise evaluation of stimulation programming settings.

As further shown in FIG. 21, the advanced tools portion 1350 may display a status regarding, and/or permit activation of, an adjust stimulation programming method 1352, an adjust sensing method 1354, and a system check method 1356. Each respective method (e.g. 1352, 1354, 1356) may be activated via activating (e.g. finger touch or stylus) a start button 1344 associated with each method.

It will be understood that the programming portion 1340 and/or additional tools portion 1350 are not limited to the particular methods and tools shown in FIG. 21, and that in some examples, additional or other methods and/or tools may be part of user interface 1300 in FIG. 21.

It will be understood that the information displayed, accessed, input, etc. on the home screen user interface 1300 may be presented in a wide variety of formats, with the example shown in FIG. 21 being just one example format.

Via the example home screen user interface 1300, a clinician is guided to observe therapy status, stimulation settings, timing settings, and is guided to potentially select a desired stimulation programming method (e.g. 1342, 1346, 1348) and/or advanced tool such as methods (e.g. 1352, 1354, 1356).

Figure 22:
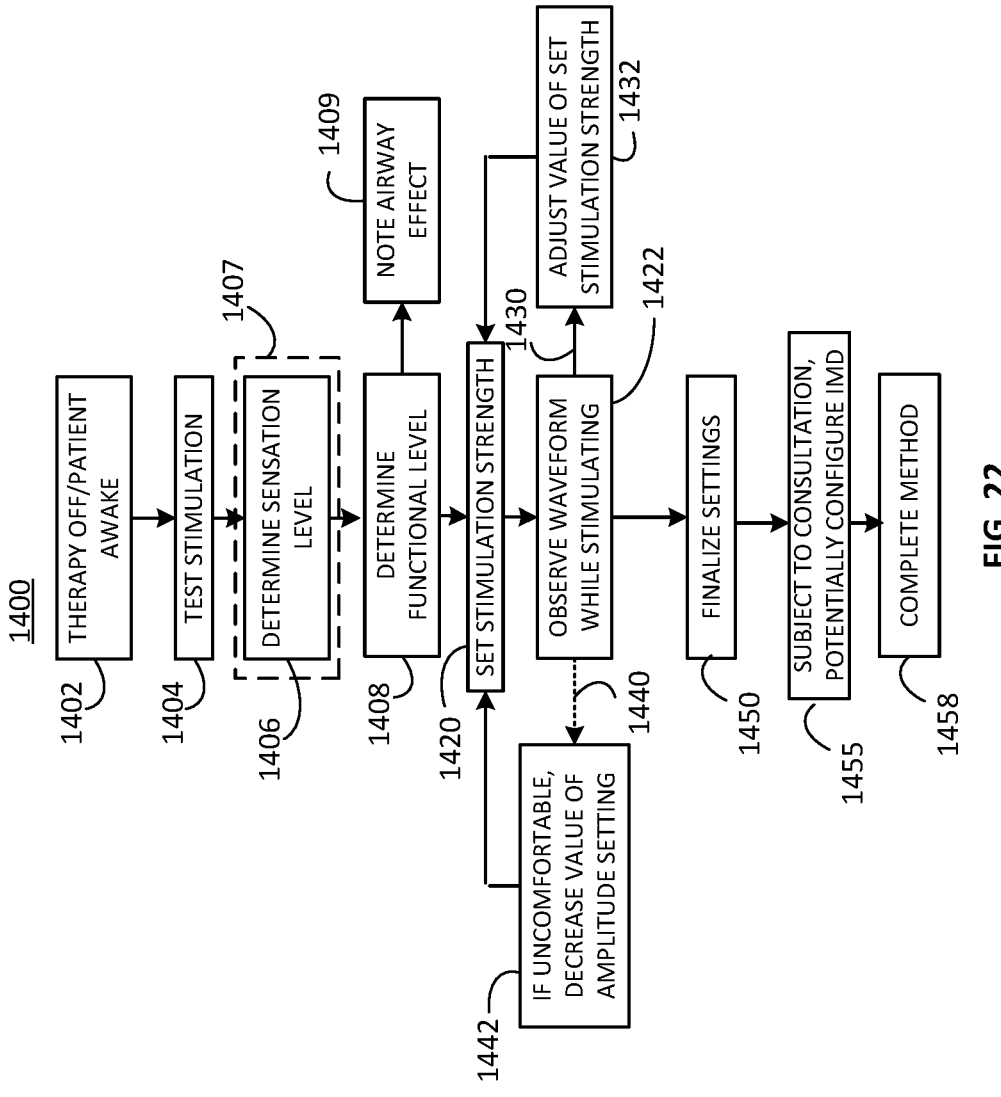
FIG. 22 is a flow diagram schematically representing an example method of stimulation programming including an initial activation of an implantable medical device.

FIG. 22 is a block diagram schematically representing an example method 1400 comprising guiding a clinician to perform stimulation programming during an initial activation of a recently surgically implanted IMD 1104, 1134 (e.g. IPG). In some examples, method 1400 may be implemented via at least some of substantially the same features and attributes as previously described in association at least FIGS. 18-20.

In some examples, a clinician may start the stimulation programming method 1400 of FIG. 22 via the START button 1344 associated with the initial activation method 1348 listed in the stimulation programming portion 1340 of the home screen user interface 1300 of FIG. 21. In some such examples, the initial activation, stimulation programming method 1400 may be implemented, at least in part, via the user interfaces 1460, 1495 in FIGS. 23, 24, as further described below in context with FIG. 22.

As shown at 1402 in FIG. 22, in some examples the method 1400 is to be performed by the clinician while a patient is awake, such as during an initial visit to the clinician after a prescribed period of time following a surgical procedure in which the IMD 1104, 1134 was implanted in the patient (along with implantation of any associated stimulation elements, sensing elements, and/or other system components).

As further shown at 1402 in FIG. 22, via a user interface (e.g. 1460 in FIG. 23; 1103 in FIG. 18), the example method 400 may comprise guiding the clinician to turn off, and/or verifying turning off (e.g. at 1312 in FIG. 23), a therapy mode of the IMD 1104, 1134 (e.g. IPG) such that therapy cannot be delivered to the patient during the clinician performing the rest of the stimulation programming method 1400.

In some examples, as shown at 1404 in FIG. 22, via a user interface (e.g. 1460 in FIG. 23, 1103 in FIG. 18) the method 1400 may comprise guiding the clinician to initiate a test stimulation function (at 1560 in FIG. 23) by which the IMD 1104, 1134 delivers a brief test stimulation signal to the patient, such as a stimulation burst. During and/or after the test stimulation, an appropriate response (e.g. airway opening, such as but not limited to tongue protrusion) should occur, as observable by the clinician. In some such examples, a value 1236 of the stimulation strength setting is selected via stimulation strength parameter 1234 and implemented via set function 1238 of the stimulation settings engine 1230 shown FIG. 20. In some examples, the value 1236 of the stimulation strength parameter 1234 and set function 1238 may be implemented via the example user interface 1460 as a stimulation strength function 1468, which includes up and down arrows 1469A (or similar mechanisms) to select the value of the stimulation strength, which is then displayable in a window 1469B. After such selection, activation of the test stimulation function 1560 causes delivery of the stimulation signal to the patient via a stimulation element.

Figure 23:
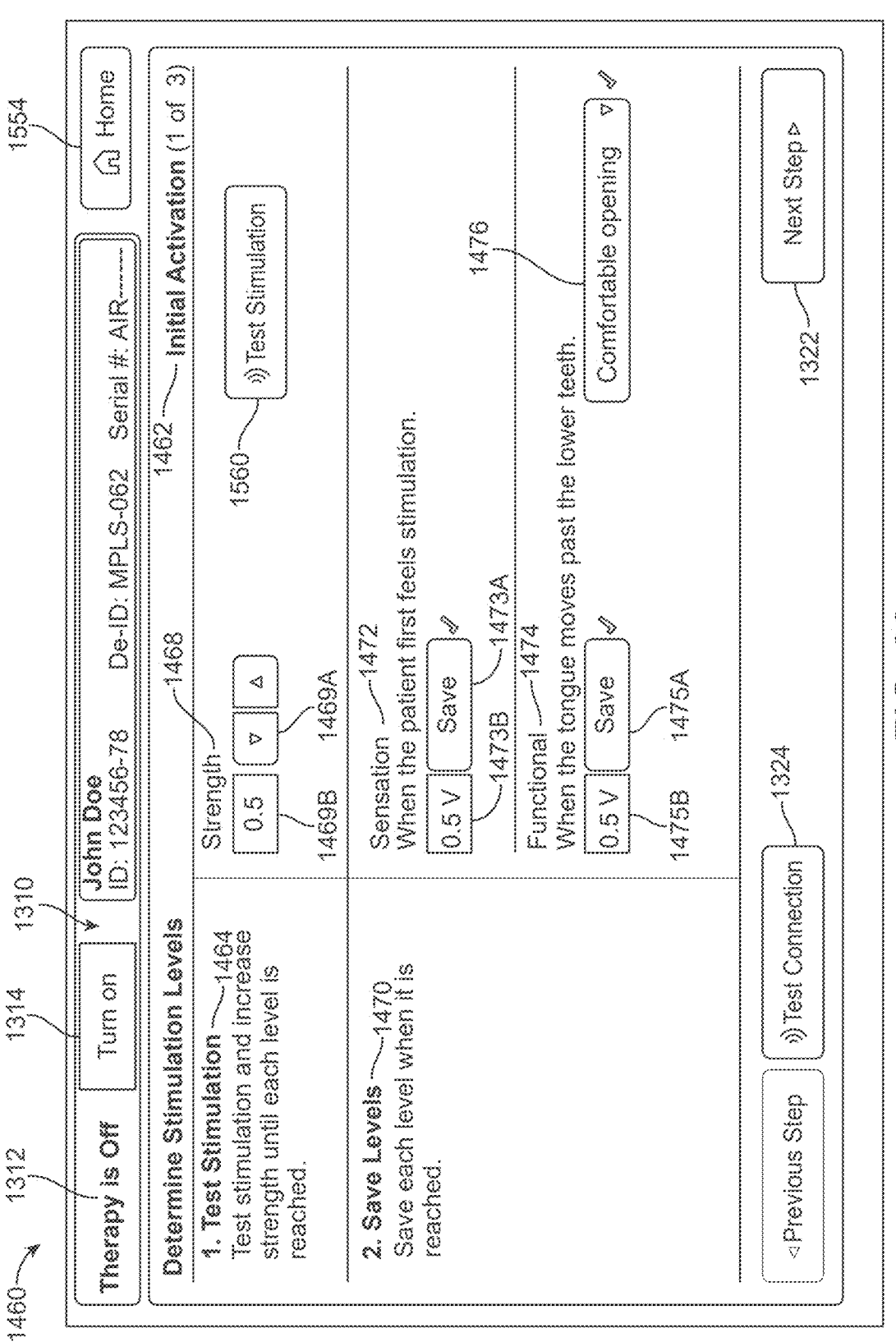
FIGS. 23-24 are each a diagram schematically representing an example initial activation user interface.

Assuming that application of the test stimulation signal is successful in producing an observable response, the example method 1400 in FIG. 22 may comprise guiding, via the user interface 1460 (FIG. 23), a clinician in determining a level of stimulation at which the patient can consciously feel a sensation (i.e. sensation level) caused by the stimulation signal, as shown at 1406 in FIG. 22. In some such examples, this determination is made by further applications of the test stimulation function 1560 (after the initial test stimulation) in which the clinician causes each successive stimulation test (e.g. via button 1560) to occur at higher stimulation strengths (e.g. amplitudes) until the patient experiences a sensation of such stimulation. The stimulation strength at which the patient experiences a sensation may be recorded, such as via the clinician activating a SAVE function (e.g. 1472 in FIG. 23), as part of aspect 1406 of the example method 1400. As shown in FIG. 23, in some examples of the method 1400 (FIG. 22), the user interface 1460 also may display the stimulation strength value 1473B (e.g. 0.5 Volts) at each successive application of stimulation and at the final stimulation strength value (at which the sensation level is achieved), which the clinician may then save (via SAVE function 1473A in FIG. 23) as the sensation level.

It will be understood that in some examples, the determination of a sensation level at 1460 in method 1400 is an optional action (as represented via dashed lines 1407), which need not be performed as part of method 1400 in FIG. 22. Moreover, it will be further understood that the application of a test stimulation at a particular "set" stimulation strength (per function 1238 in FIG. 20) does not automatically result in a change in the configured stimulation strength settings of the IMD 1104, 1134. Accordingly, in at least some examples, any such "set" stimulation strength is merely temporary, and such setting of the stimulation strength with respect to determining a sensation level (at 1406) will be discarded upon the clinician navigating away from the user interface 1460 in FIG. 23).

After following the method 1400 to determine the sensation level (at 1406 in FIG. 22), the example method 1400 may comprise guiding a clinician, via the user interface 1460, in determining a level of stimulation at which a functional motion (e.g. airway opening such as but not limited to tongue protrusion) occurs and may be observed by the clinician, as shown at 1408 in FIG. 22. In some such examples, this determination is made by further applications of the test stimulation function (after optional identification of the sensation level at 1406) in which each successive stimulation test may be performed at higher stimulation strengths until the functional motion (e.g. airway opening) occurs and which is observed by the clinician.

Again, according to the method 1400 in FIG. 22, the value 1236 of the stimulation strength may be selected via parameter 1234 and implemented via the set function 1238 of the stimulation settings engine 1230, as described above with regard to the stimulation strength setting function 1468 (FIG. 23). Moreover, in some examples, via the user interface 1460, the method 1400 comprises guiding the clinician to save (e.g. such as via a SAVE function 1475A in FIG. 23) the stimulation strength at which the functional motion (e.g. airway opening) occurs, as part of aspect 1408 of the example method 1400. As part of the example method 1400 (FIG. 22), the user interface 1460 in FIG. 23 also may display the final stimulation strength value 1475B (at which the functional level is achieved), which the clinician may then save (via SAVE function 1475A in FIG. 23) as the functional level.

As further shown at 1409 in FIG. 22, in some examples the method 1400 comprises a descriptor function 1476 by which the clinician may note, via the user interface 1460 in FIG. 23, a descriptor of the type of airway opening which occurred at the saved functional level 1474, which then remains displayed on the user interface 1460, such as at 1475B. In some such examples, at least some example descriptors may comprises opening, comfortable opening, protrusion, comfortable protrusion, and the like.

As shown at 1420 in FIG. 22, once the sensation level (per 1472 in FIG. 23) and/or the functional level (per 1474 in FIG. 23) have been established, the example method 1400 may comprise guiding the clinician (e.g. via the user interface 1103 in FIG. 18) into a next step in which the clinician sets an stimulation strength value at which the effects of the stimulation will be evaluated via observing a respiration waveform. In doing so and via the user interface 1103, the method 1400 guides a clinician to electively select the value of the stimulation strength setting at which the functional level (e.g. 1474 in FIG. 23) occurred while the method 1400 (FIG. 22) may display a recommendation to do so, which the clinician may follow via their discretion.

It will be noted that in some examples, one or more of the example user interfaces (e.g. 1460 in FIG. 23, 1495 in FIG. 24, other) may comprise a NEXT STEP function 1322 to enable moving onto a next step of one of the example methods and/or comprise a PREVIOUS STEP function 1320 to enable moving onto a previous step of one of the example methods. Meanwhile, one or more of the example user interfaces (e.g. 1460 in FIG. 23, 1495 in FIG. 24, other) may comprise a TEST CONNECTION function 1324 to test a communication connection used in the programming for stimulation therapy.

With the stimulation strength selected and via the user interface 1103 (FIG. 18), at 1422 in FIG. 22 the example method 1400 comprises guiding the clinician to start a further test stimulation during which the clinician may observe, via the user interface 1103, a displayed, sensed respiratory waveform of the patient (and the timing of the applied stimulation relative to the displayed sensed respiratory waveform).

Via path 1430 and as shown at 1432 in FIG. 22, and via the user interface 1103, in some examples the method 1400 may comprise guiding the clinician to adjust the value of the stimulation strength setting (e.g. as an increase or decrease) at which the stimulation strength is set (1420) and further observe the respiratory waveform and effect of the applied stimulation (1422). In this way, the clinician may adjust the stimulation setting to evaluate different stimulation strengths of a therapeutic stimulation signal.

Once the clinician determines a suitable stimulation strength setting for therapy, then as shown at 1450 in FIG. 22, the example method 1400 may comprise guiding the clinician (via the user interface 1103) to a next step of reviewing and finalizing the overall stimulation and timing settings of the stimulation therapy to which the IMD 1104, 1134 potentially would be configured for use by the patient. In some such examples, the user interface 1103 (FIG. 18) may take the form shown as the example user interface 1495 in FIG. 24 via which the clinician may review the finalized, initial therapy settings.

Figure 24:
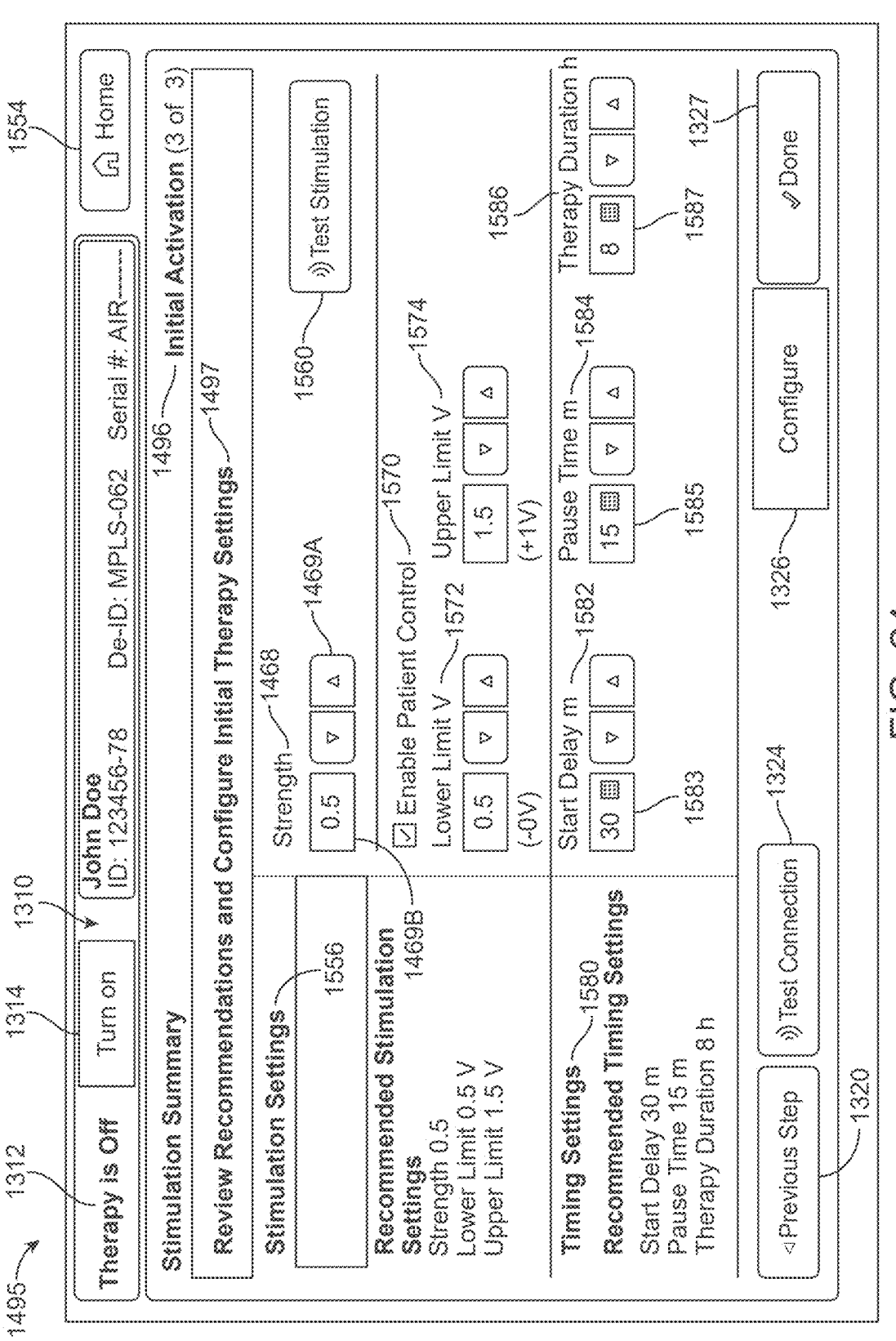

As shown in FIG. 24, the "initial activation" user interface 1495 may comprise a banner 1310 (like in FIG. 21), an indicator 1496 of the Initial Activation method, and/or a "Review Recommendation and Configure Initial Therapy Settings" indicator 1497. This "initial activation" user interface 1495 also displays stimulation settings 1556, which may comprise a listing of Recommended Stimulation Settings, such as stimulation strength (e.g. an amplitude 0.5 V, other), lower stimulation strength limit (e.g. 0.5 V), and upper stimulation strength limit (e.g. 1.5 V). The stimulation settings 1556 also may comprise a current stimulation strength setting function 1468, lower limit function 1572 (e.g. 240 in FIG. 20), and/or upper limit function 1574 (e.g. 242 in FIG. 20). In some examples, each of the respective functions 1468, 1572, 1574 includes increase (e.g. up arrow) and decrease (e.g. down arrow) buttons 1469A, and window 1469B to display the selected numeric value of the respective parameter. The stimulation settings portion 468 also may comprise an "enable patient control" function 1570 by which the clinician can authorize the patient to have some control over the stimulation strength settings, with the user-selectable stimulation strength values falling between the lower limit (1572) and upper limit (1574) set by the clinician. In some examples, each of the respective functions

1572, 1574 includes an increase button (up arrow), decrease button (down arrow), and window to display the selected numeric value of the respective function (e.g. parameter).

As further shown in FIG. 24, the "initial activation" user interface 1495 also may comprise displaying timing settings 1580 such as "Recommended Timing Settings" including settings for a start delay (e.g. 30 minutes), pause time (e.g. 15 minutes), and therapy duration (e.g. 8 hours). The timing settings 1580 also may comprise a start delay function 1582, pause time function 1584, and/or therapy duration function 1586. In some examples, each of the respective functions 1582, 1584, 1586 includes an increase button (up arrow), decrease button (down arrow), and window (e.g. 1583, 1585, 1587) to display the selected numeric value of the respective function (e.g. parameter).

With further reference to FIG. 22, as shown at 1450 and via the user interface 1495 in FIG. 24 (1103 in FIG. 18), the clinician reviews and finalizes the stimulation settings 1556 and timing settings 1580 (FIG. 24).

Upon such final review, via the user interface 1495, at 1455 in FIG. 22 the example method 1400 guides the clinician to authorize the programmer 1102 to configure the IMD 1104, 1134 (via CONFIGURE function 1326 in user interface 1495 FIG. 23) according to the final stimulation strength and timing settings.

However, it will be understood in some examples, as shown at 1442 in FIG. 22 and via the respective user interfaces, the example method 1400 may comprise guiding the clinician, that in the course of adjusting the stimulation strength settings prior to finalizing a selected stimulation strength, to decrease the value of the selected stimulation strength setting if the patient experiences discomfort upon selection of a particular stimulation strength. The dashed nature of the directional arrow 1440 in FIG. 22 indicates that, in at least some examples, the clinician may take such action only when it is believed to be necessary. Stated differently, in absence of the patient exhibiting discomfort, the clinician may complete the method 1400 using ordinary adjustment of the value of the stimulation strength at 1432 (e.g. via at least stimulation strength function 1468 in user interfaces 1460, 1495, in FIGS. 23, 24 or other user interfaces) without proceeding along the "discomfort adjustment" pathway 1440.

With further reference to the action at 1442, after the decrease in the selected value of the stimulation strength, via the user interfaces (e.g. 1460, 1495, other) the clinician again implements the set stimulation strength function (1420 in FIG. 22) and then may observe the sensed respiratory waveform and associated stimulation settings (1422 in FIG. 22). If the patient still exhibits discomfort, the clinician may repeat the action of decreasing the value of the stimulation strength (1442 in FIG. 22), followed by setting the stimulation strength (1420 in FIG. 22), and further observing the respiratory waveform (1422 in FIG. 22).

In some examples, the method (e.g. via a user interface) may guide or prompt (e.g. invite) the clinician to cause recording of a sample of the displayed, sensed respiratory waveform.

In some examples, at 1450 in FIG. 22, the method 1400 may comprise finalizing the settings (stimulation and timing) used to configure the IMD 1104, 1134 as including a lower limit (1240 in FIG. 20) and an upper limit (1242 in FIG. 20) of the stimulation strength values between which a patient may be permitted to make minor adjustments to their therapy. These limits 1240, 1242 (FIG. 20) may be displayed to the clinician via the user interface 495 in FIG. 24, along with display of a start delay 1582 (e.g. 1262 in FIG. 20), pause duration (e.g. minutes) 1584 (e.g. 1264 in FIG. 20), and/or a therapy duration (e.g. 8 hours) 1586 (e.g. 1266 in FIG. 20). It will be understood that, in some examples, a potential change in configured settings of the IMD 1104, 1134 may be subject to consultation with a physician or other caregiver.

As further shown at 1458 in FIG. 22, in some examples the method 1400 may be concluded, via the user interface 1495, by exiting the method with the user interface 1495 displaying a completed or done status 1327 regarding the initial activation engine (1212 in FIG. 20).

In some examples, completion of the method 1400 results in a more general method causing the user interface to displaying a home screen (such as via engine 1211 in FIG. 20), which may provide a summary status of the various clinician programming methods and IMD settings. For instance, home screen user interface 1300 in FIG. 21 provides one example at least some of the information displayed on a home screen following completion of the initial activation method 1400 in FIG. 22. Accordingly, as shown in FIG. 21, in some such examples, the home screen user interface 1300 also may display information regarding a therapy status, stimulation settings summary, as well as patient details. In some examples, the programming portion 1340 of the home screen user interface 1300 (FIG. 21) may display the summary status (e.g. done, to be performed, etc.) of the stimulation programming methods (e.g. 1342, 1326, 1348, etc.) and also may provide mechanisms (e.g. START button 1344) for a clinician to activate each of the respective methods (e.g. 1342, 1346 etc.) supported by the respective engines (e.g. 1212, 1214, 1216, etc. in FIG. 20).

Figure 25A:
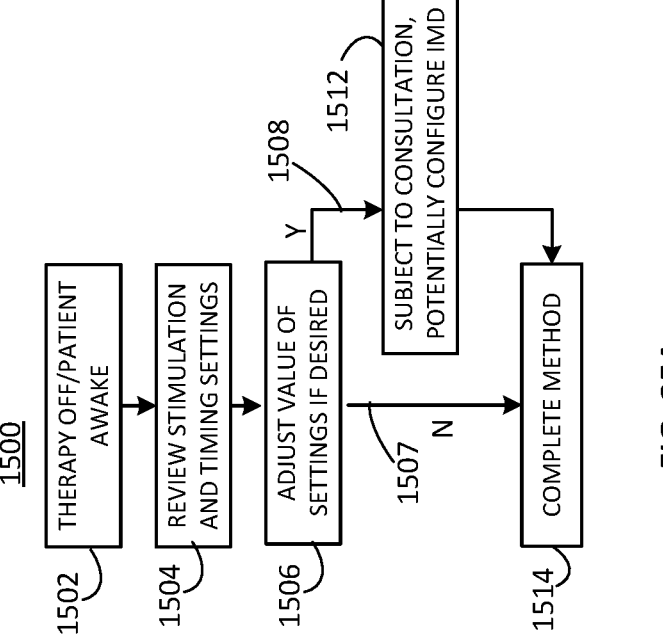

FIG. 25A is a flow diagram schematically representing an example method 1500 comprising guiding a clinician in evaluating stimulation programming for an IMD 1104, 1134, such as might occur during the patient making a follow-up visit to a clinician after the patient has been employing the therapy for some weeks, months, or other selectable time period. In some examples, a general method implemented via a home screen may provide for selection of a follow-up method 1342. For instance, in some examples, a clinician may start the follow-up method 1500, 1530 of FIGS. 25A, 26 via the START button 1344 associated with the follow-up method 1342 listed in the programming portion 1340 of the home screen user interface 1300 in FIG. 21.

In some examples, prior to employing the basic follow-up, method 1500 (FIG. 25A) may comprise displaying at a user interface (e.g. 1103 in FIG. 18) a selection for the clinician to choose between a basic follow-up and an advanced follow-up. Of course, the clinician can choose to perform both of the basic and advanced follow-ups if they so desire. In some examples, the choice between the basic or advanced follow-up may be displayed on the general home screen (e.g. 1300 in FIG. 21) or on an introductory screen as part of the follow-up method 1500.

Figure 25B:
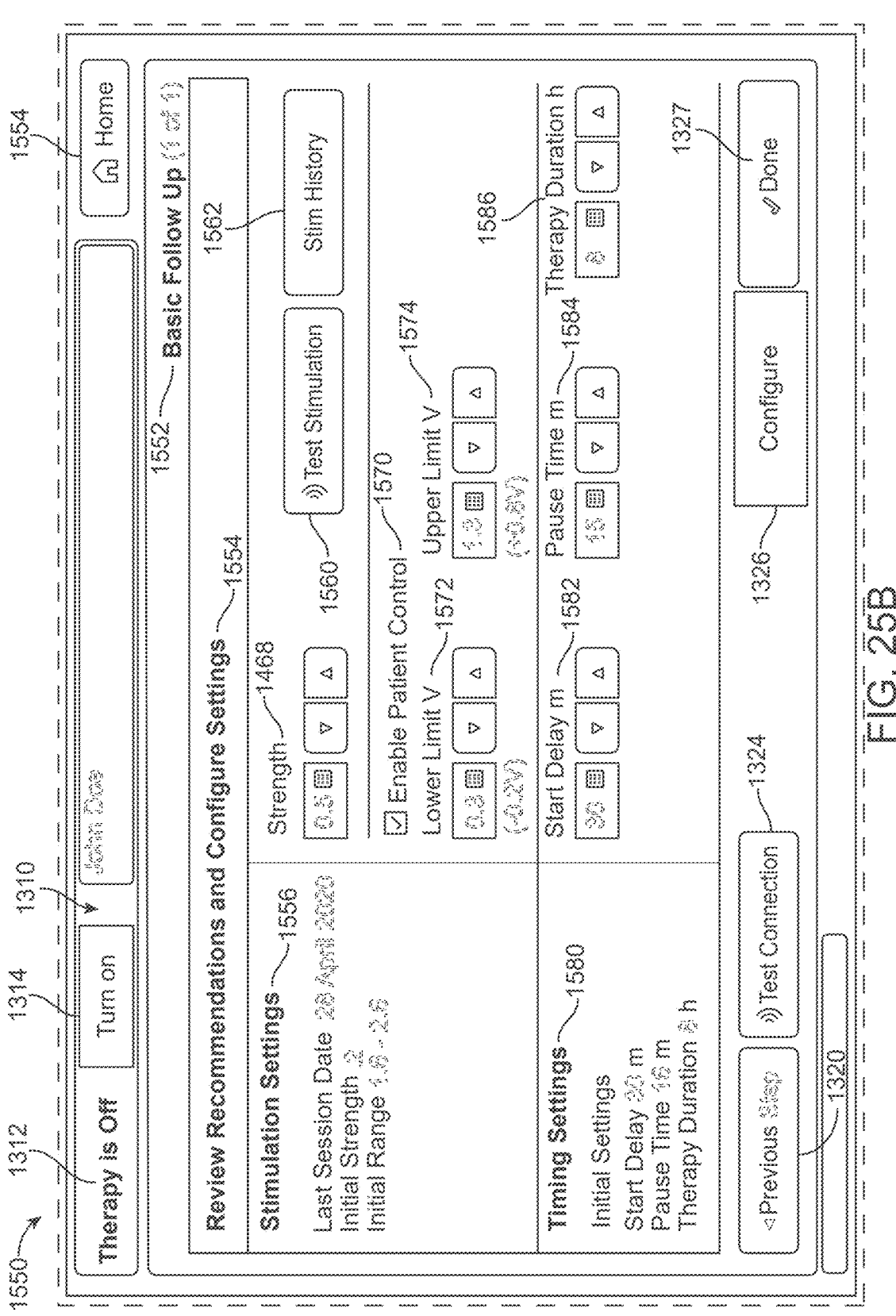
FIG. 25B is a diagram schematically representing an example basic follow-up user interface.

As shown at 1502 in FIG. 25A, via a user interface (e.g. 1103 in FIG. 18) the example method 1500 comprises guiding the clinician to turn therapy off (or confirm that the therapy is already off) in the IMD 1104, 1134 and to begin the method with the patient in an awake state, such as previously shown at 1312 in FIG. 21. In some examples, this action and other actions of the method 1500 in FIG. 25A may be supported by an example "basic follow-up" user interface 1550, such as shown in FIG. 25B. In some such examples, the "basic follow-up" user interface 1550 may comprise at least some of substantially the same features and attributes as the "initial activation" user interface 1495 in FIG. 24, except for a few differences noted below in context with a description of the method 1500 of FIG. 25A. For instance, the "basic follow-up" user interface 1550 may comprise a banner 1310 (like in FIGS. 21, 24), an indicator 1552 of the Basic Follow-up method, and/or a heading "Review Recommendation and Configure Settings" 1554. This "basic follow-up" user interface 1550 also displays stimulation settings 1556, which may comprise a listing of the last session date, initial stimulation strength, and/or initial range of stimulation strength. The stimulation settings 1556 also may comprise a current stimulation strength setting function 1468 and the lower and upper limit functions 1572, 1574, as in FIG. 24.

As further shown in FIG. 25B, the "basic follow-up" user interface 1550 also may comprise displaying timing settings 1580 such as initial settings of a start delay 1582 (e.g. 30 minutes), pause time 1584 (e.g. 15 minutes), and therapy duration 1586 (e.g. 8 hours).

With further reference to FIG. 25A, as shown at 1504 and via the user interface 1550 in FIG. 25B, per method 1500 the clinician may review the stimulation settings 1556 and timing settings 1580, while considering feedback from the patient as well as any tracking information from the IMD 1104, 1134 regarding performance of the IMD 1104, 1134, effectiveness of the therapy, and the like. Among other information, the user interface 1550 in FIG. 25B may display any stimulation strength changes that the patient has selected (within a permitted range such as lower limit 1572 (1240 in FIG. 2) and upper limit 1574 (1242 in FIG. 20) during the ordinary course of employing the therapy on a nightly basis, usage hours, and the like. In some examples, such patient changes, certain usage data, etc. since the patient's last visit may be highlighted in the user interface 1550 via flags or other indicators to catch the clinician's attention in reviewing the stimulation and timing settings. At least some of this historical information may be accessed and/or displayed via a Stimulation history function ("Stim History") 1562 in user interface 1550 in FIG. 25B.

As shown at 1506 in FIG. 25A, in some examples the example method 1500 comprises facilitating the clinician in making any desired adjustments to the stimulation and timing settings, such as via the stimulation strength value setting function 1468 and the test stimulation function 1560 shown in the user interface 1550 in FIG. 25B. If no changes are to be made, then via pathway 1507 the method 1500 may terminate as shown at 1514 in FIG. 25A. However, if the clinician desires to make changes to the stimulation and timing settings in the IMD 1104, 1134, then via pathway 1508 in FIG. 25A, the method 1500 comprises guiding the clinician (subject to consultation with a physician or other caregiver) via the user interface 1550 in FIG. 25B to potentially cause configuration of the IMD 1104, 1134 according to the new stimulation and timing settings, as shown at 1512 in FIG. 25A. As shown in FIG. 25B, in some examples the user interface 1550 comprises a CONFIGURE function 1326 to implement making such configuration changes in the IMD 1104, 1134 per the method 1500 in FIG. 25A. The method 1500 may be terminated at 1514, which may be implemented in some examples via the DONE function 1327 in the user interface 1550 in FIG. 25B.

Figure 27A:
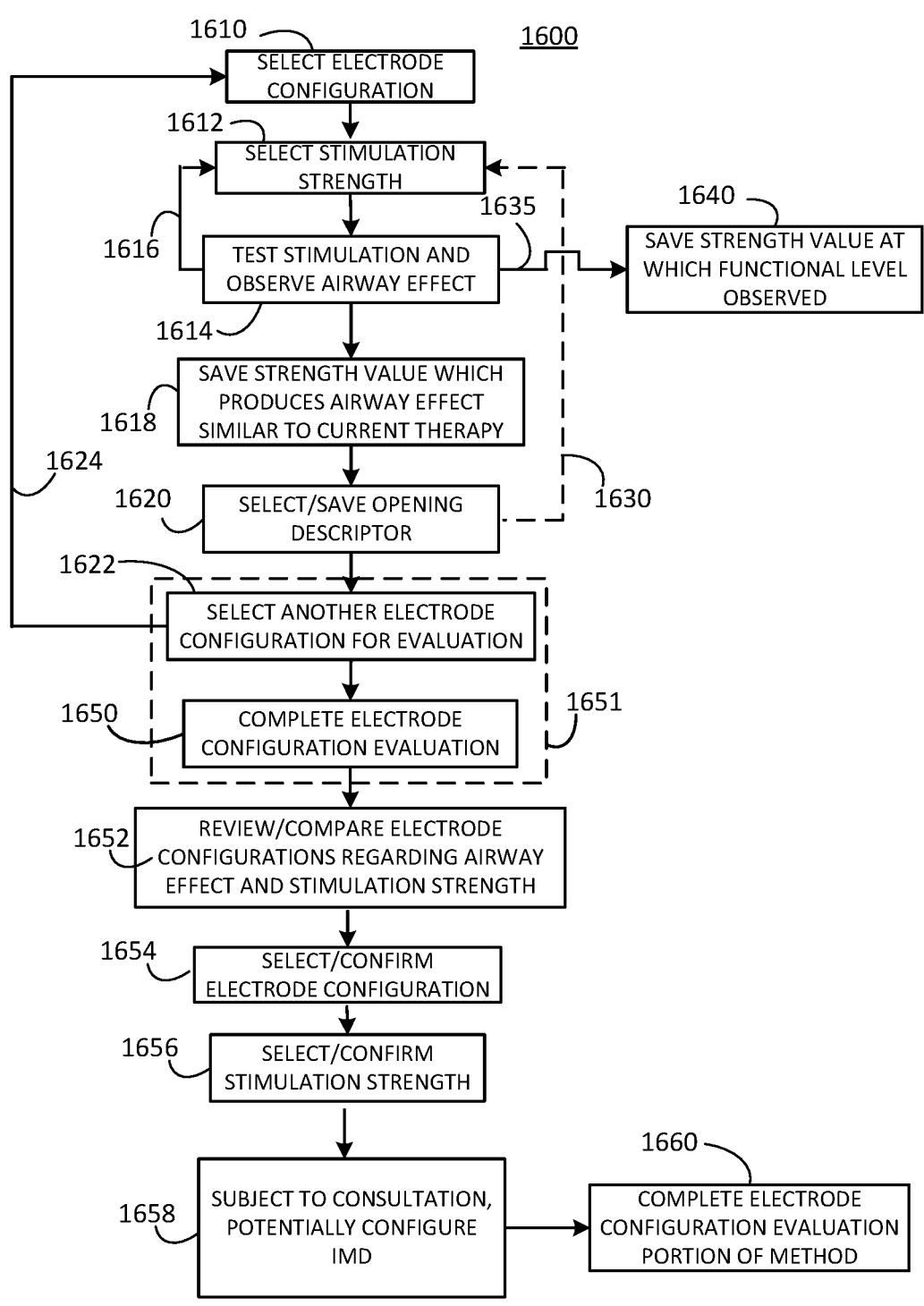
FIG. 27A is a flow diagram schematically representing an example method of stimulation programming for an electrode configuration.
Figure 27B:
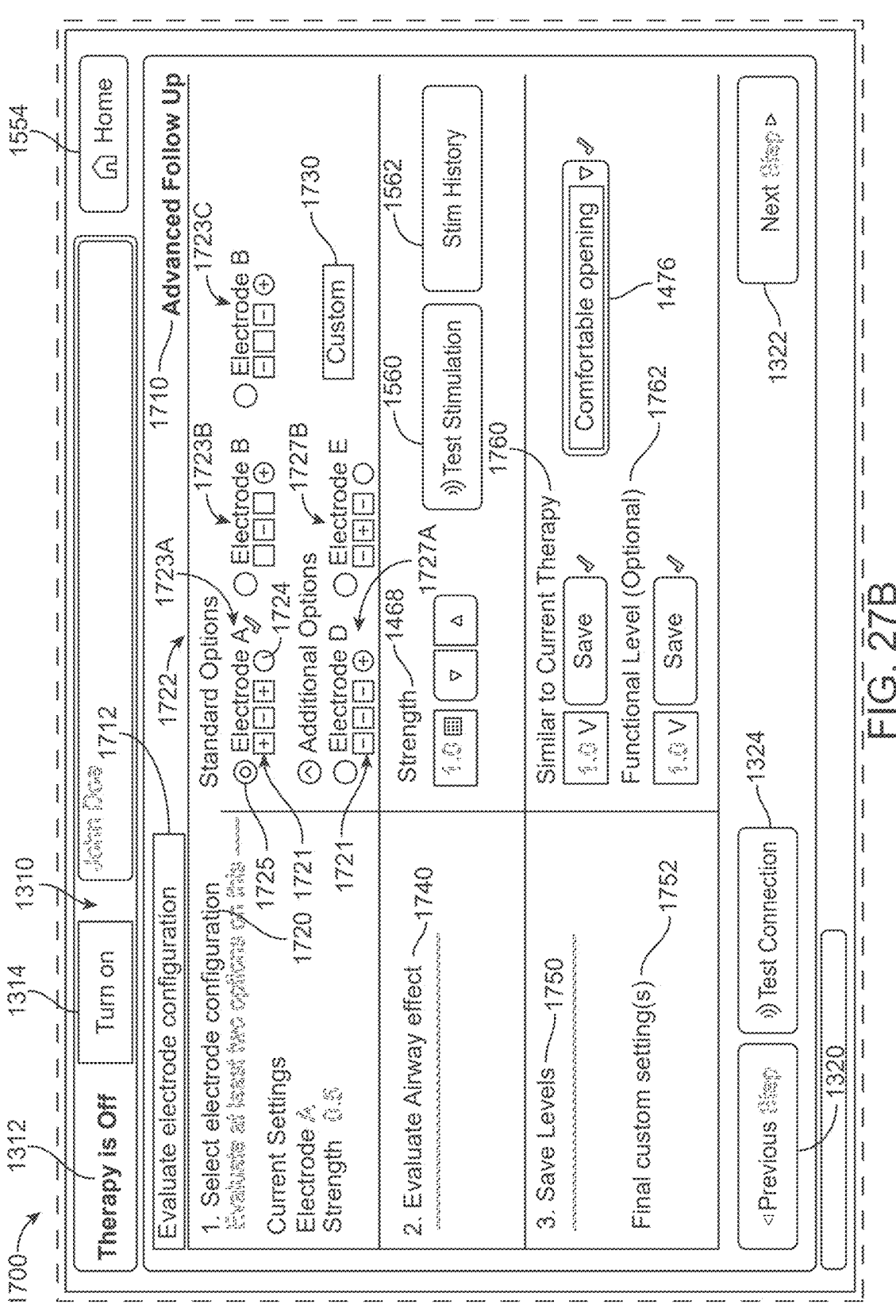
FIG. 27B is a diagram schematically representing an example advanced follow-up user interface for an electrode configuration.
Figures 27C, 27D, 27E:
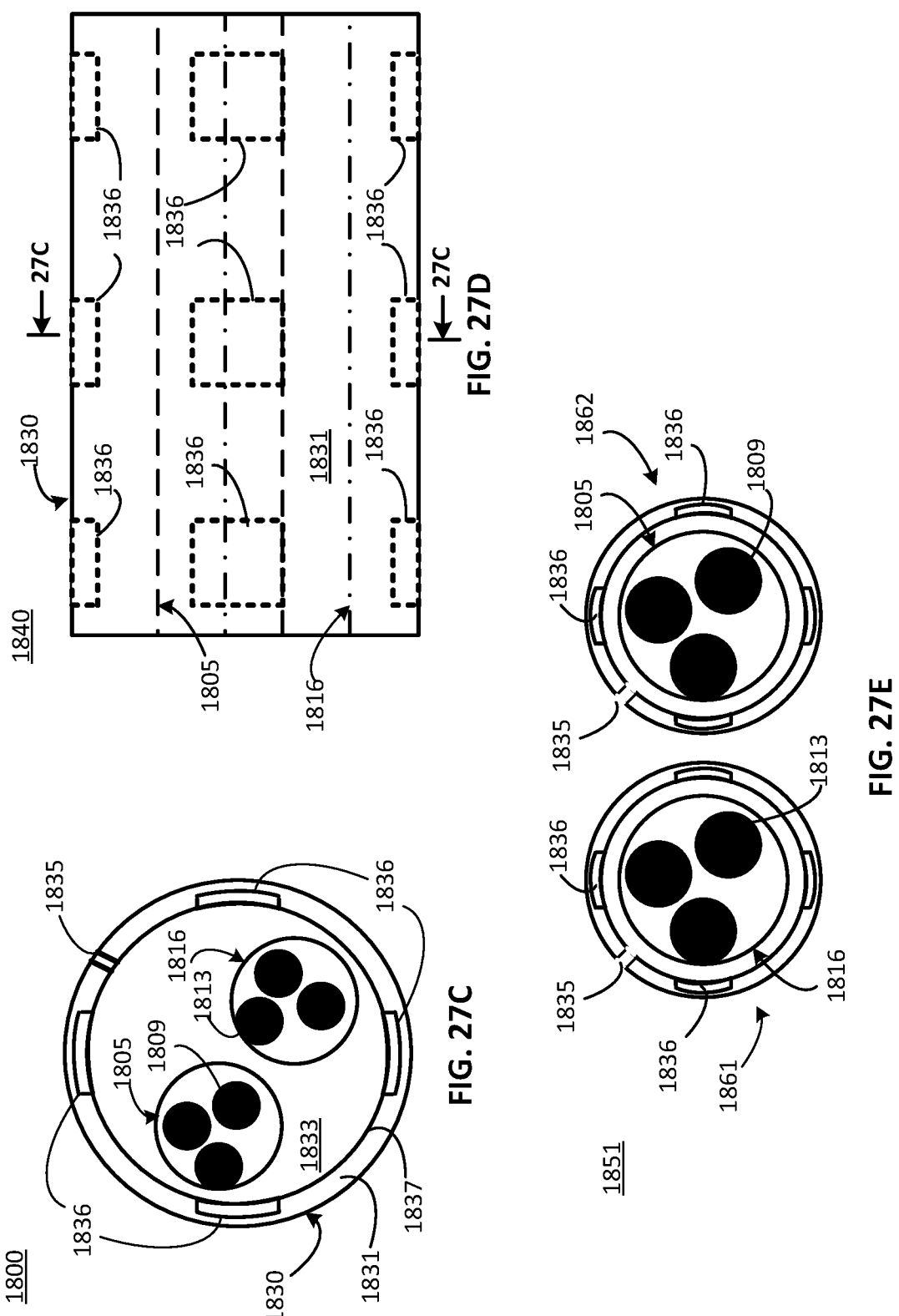
FIG. 27C is a sectional view as taken along lines 27C-27C of FIG. 27D schematically representing a cuff electrode to encircle and engage at least one nerve.
FIG. 27D is a side view of an example cuff electrode.
FIG. 27E is a sectional view similar to the view of FIG. 27C and schematically representing two cuff electrodes, with each respective cuff electrode encircling and engaging a nerve.
Figures 27F, 27G, 27H:
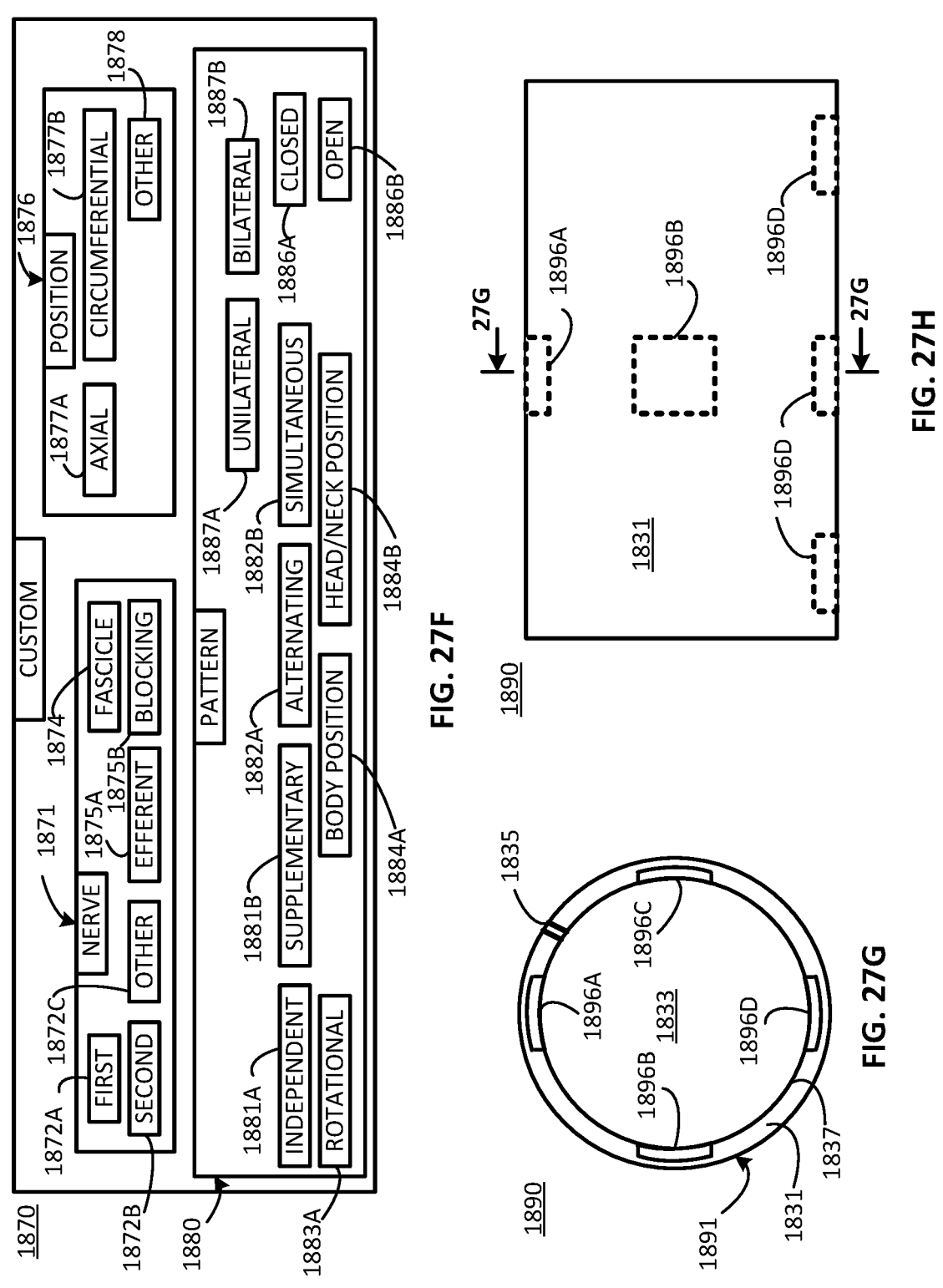
FIG. 27F is a block diagram schematically representing an example custom stimulation programming engine.
FIG. 27G is a sectional view as taken along lines 27G-27G of FIG. 27H schematically representing a cuff electrode.
FIG. 27H is a side view of an example cuff electrode.
Figure 28A:
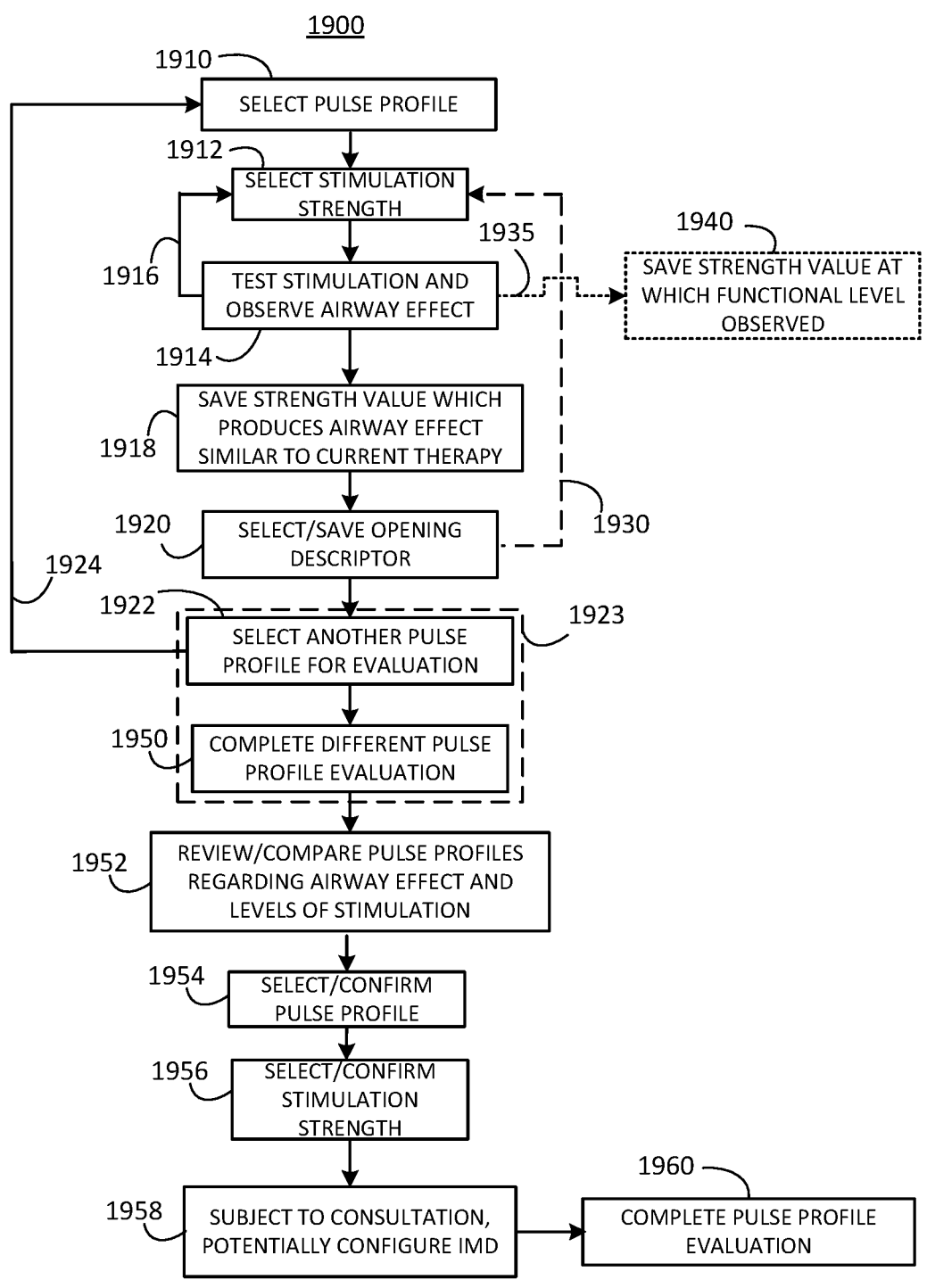
FIG. 28A is a flow diagram schematically representing an example method for stimulation programming for a pulse profile.
Figure 28B:
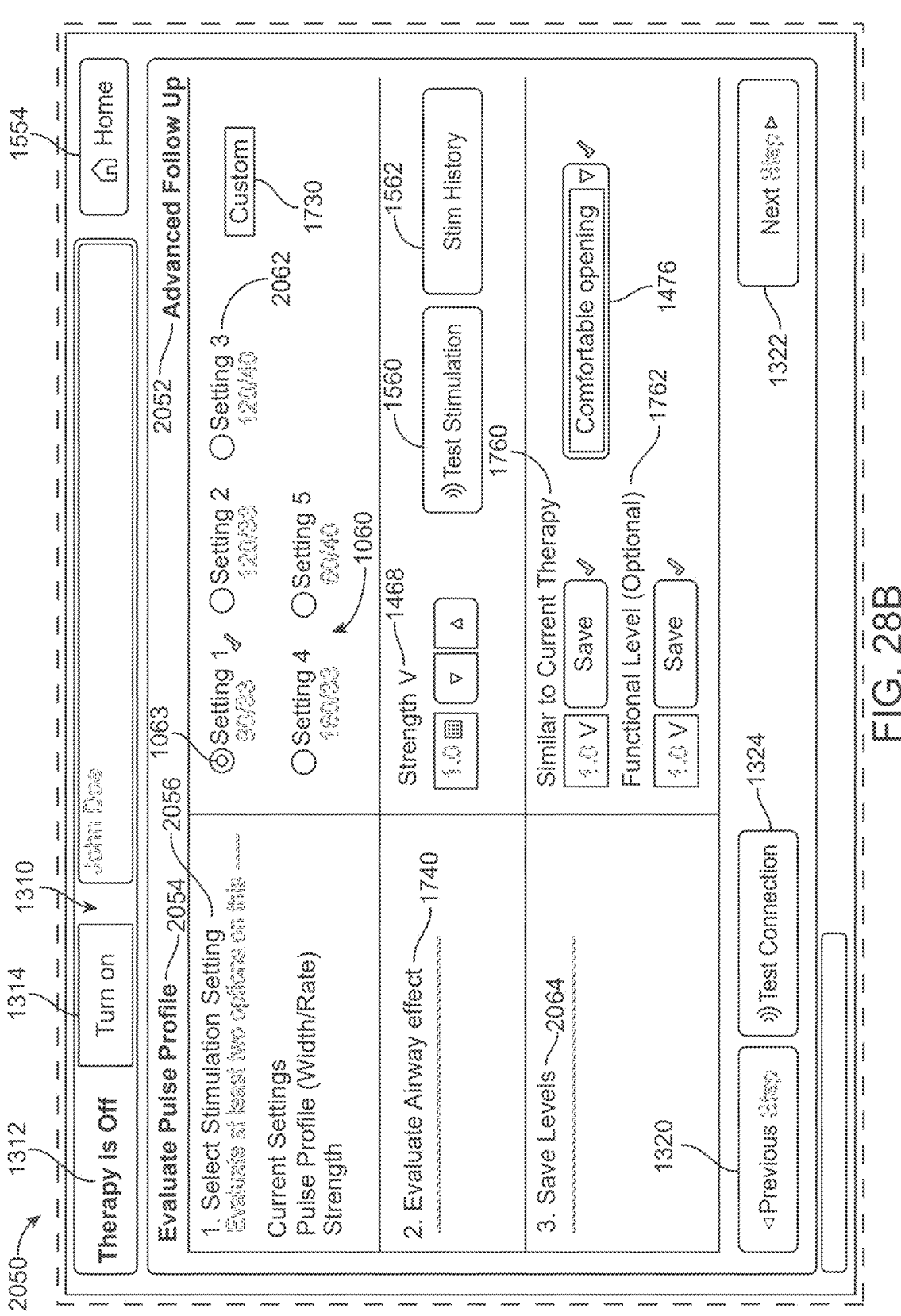
FIG. 28B is a diagram schematically representing an example advanced follow-up user interface for pulse profile.
Figure 28C:
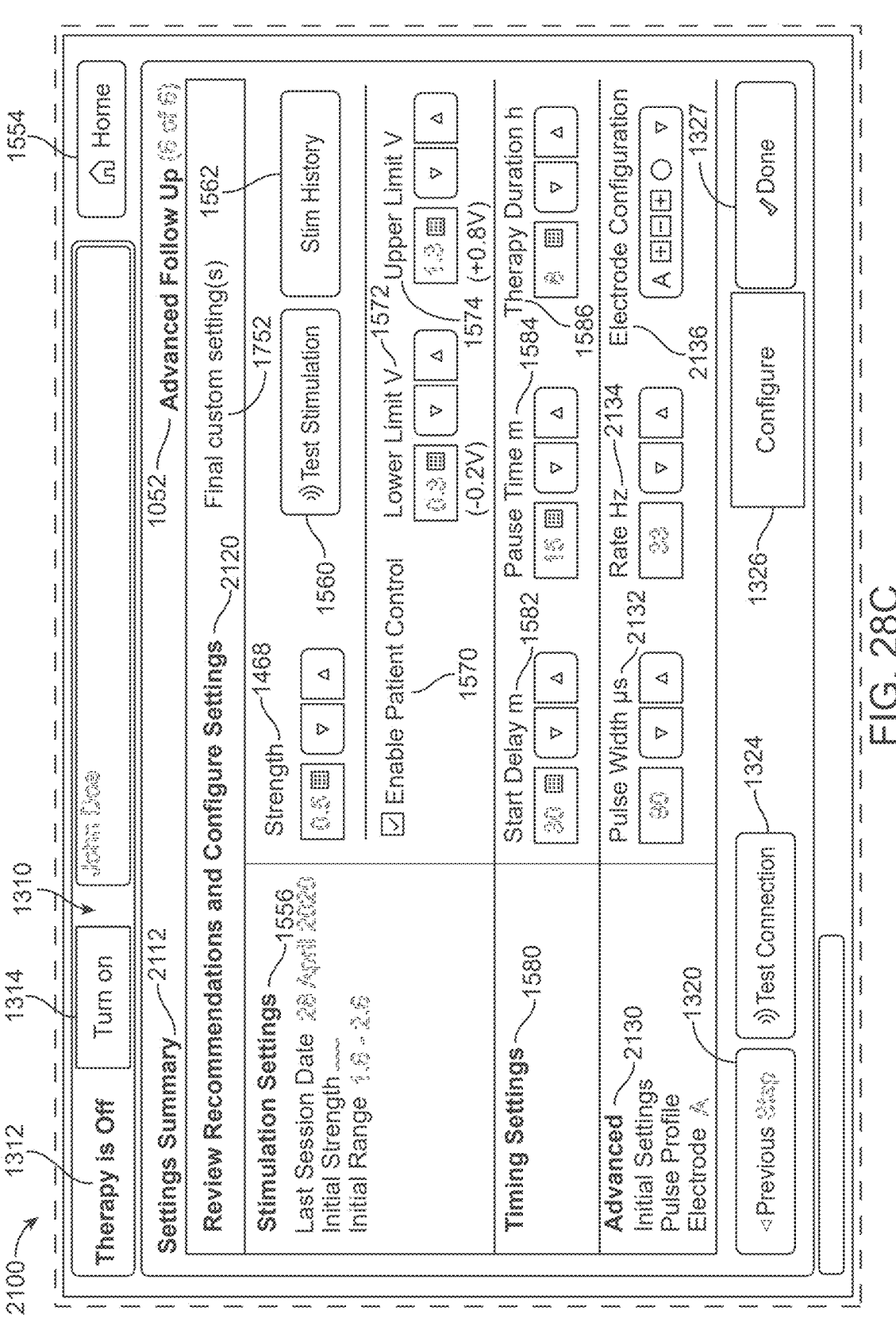
FIG. 28C is a diagram schematically representing an example advanced follow-up user interface providing a summary of stimulation programming settings.

In some examples, upon clinician selection of an advanced follow-up such as via a more general method (e.g. via user interface 1103 in FIG. 18 and/or user interface 1300 in FIG. 21), the method may comprise guiding the clinician through the example methods 1530 (FIG. 26), 1600 (FIGS. 27A-27G) and 1900 (FIGS. 28A-28C).

Figure 26:
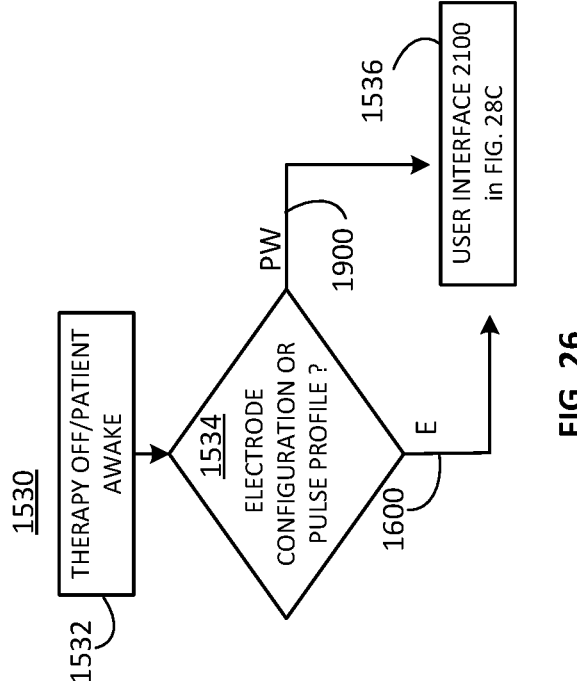
FIGS. 25A and 26 are each a flow diagram schematically representing an example method of stimulation programming, including performing a basic follow-up.

As in method 1500, at 1532 in FIG. 26 the advanced follow-up method 1530 begins with the therapy off and the patient awake. As further shown at 1534 in FIG. 26, in some examples the method 1530 guides the clinician to choose either an electrode configuration (E) evaluation method 1600/or a pulse profile (PW) evaluation method 1900. It will be understood that upon the clinician selecting one of these methods (e.g. electrode configuration evaluation method 1600 or pulse profile adjustment method 1900), the method 1530 in FIG. 26 permits the non-selected respective method to be performed after completion of the initially selected method (e.g. electrode configuration or pulse profile). Stated differently, a clinician may perform both of the stimulation programming methods 1600 (FIG. 27A) and 1900 (FIG. 28A) if desired and can select the order in which those methods 1600, 1900 are performed. Selection of the electrode configuration evaluation method is represented via directional arrow 1600 in FIG. 26 and further illustrated and described in association with at least FIGS. 27A-27G, while selection of the pulse profile adjustment method is represented via directional arrow 1900 and further illustrated and described in association with at least FIGS. 18A-18C.

As represented at 1536, in some examples completion of the pathways in FIG. 26 of the method 1600 (FIG. 27A) and/or method 1900 (FIG. 28A) will result in the clinician arriving at the later-described user interface 2100 in FIG. 28C, which provides a Settings Summary 2112, which may enable reviewing current settings of an IMD 1104, 1134, may provide recommendations, and may provide the ability for a clinician to potentially cause configuration of any new settings into the IMD 1104, 1134.

In some examples, the respective example methods 1530 (FIG. 26), 1600 (FIGS. 27A-27G), and 1900 (FIGS. 28A-28C) may be implemented, at least in part, via the electrode configuration function 1272 and pulse profile function 1274 in the advanced follow-up engine 1270 of stimulation programming engine 1200 in FIG. 20.

With this in mind, FIG. 27A is a flow diagram schematically representing an example electrode configuration evaluation method 1600. In general terms, the electrode configuration evaluation method 1600 enables the clinician to evaluate the stimulation settings on an electrode configuration-by-electrode configuration basis, which provides an evaluation of the general effectiveness of each electrode configuration (or groups of electrode configurations) in delivering stimulation and/or an evaluation (and potential adjustment) of the particular stimulation settings for that particular electrode configuration.

Figure 32B:
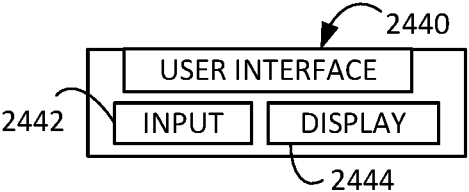
FIG. 32B is a block diagram of an example user interface.

In some examples, the example method 1600 may be implemented via at least some of substantially the same features and attributes as previously described in association with at least FIGS. 18-26 and the control portion 2400 (FIG. 32A), and user interface 1103 (FIG. 18), 2440 (FIG. 32B).

In some examples, the user interface 1700 in FIG. 27B comprises a more specific example implementation of user interface 1103 (FIG. 18), which may embody at least some aspects of, and/or facilitate, method 1600. As shown in FIG. 27B, user interface 1700 may comprise a banner 1310 with features (e.g. 1312, 1314) similar to that shown in FIGS. 21, 23, etc. In addition, the user interface 1700 may comprise an evaluate electrode configuration portion 1712 and advanced follow-up indicator 1710. The evaluate electrode configuration portion 1712 may comprise a select electrode configuration portion 1720, an evaluate airway effect portion 1740, and/or a save levels portion 1750. Further details regarding each of these respective portions 1720, 1740, 1750 will be described below in the context of method 1600.

Accordingly, as shown at 1610 in FIG. 27A and via select electrode configuration portion 1720 in user interface 1700 of FIG. 27B, the example electrode configuration evaluation method 1600 comprises selecting for evaluation at least one electrode configuration of multiple electrode configurations of a stimulation element (e.g. 1140 in FIG. 19) associated with the IMD 1104, 1134 (FIGS. 18-19).

As further shown in FIG. 27B, in some examples the select electrode configuration portion 1720 may provide a listing of current electrode configuration settings, such as which electrode configuration is selected (e.g. A, B, etc.) and a stimulation strength setting. In addition, the select electrode configurations portion 1720 may comprise, for evaluation, standard options portion 1722 and advanced options portion 1726.

In some examples, the standard options portion 1722 may comprise a plurality of selectable electrode configurations 1723A, 1723B, 1723C, along with a selection indicator 1725 for each electrode configuration 1723A, 1723B, 1723C. It will be understood that each electrode configuration 1723A, 1723B, 1723C may comprise an arrangement 1721 of multiple electrode contacts, including anode and cathode elements (e.g. +, –) with the electrode contacts being present on a stimulation element and/or other location (e.g. case of the IMD 1104, 1134). As shown in FIG. 27B, each electrode configuration 1723A, 1723B, 1723C may comprise a different anode/cathode arrangement. In some examples, each electrode configuration 1723A, 1723B, 1723C may comprise an IMD case indicator 1724 (e.g. circle) which may further identify the use of a case of the IMD as an anode or cathode via symbols (e.g. +, –).

In some examples, the select electrode configuration portion 1720 also may comprise an additional options portion 1726, which comprises one or several selectable electrode configurations 1727A, 1727B, etc. which may comprise at least some of the above-described features of the selectable electrode configurations 1723A, 1723B, 1723C. These selectable electrode configurations 1727A, 1727B, etc. may correspond to electrode configurations which may be available on some stimulation elements (e.g. 1140 in FIG. 19), but not available on other stimulation elements. At least some features and attributes associated with the use of these additional selectable electrode configurations 1727A, 1727B are further described in association with at least FIGS. 27C-27H.

As shown in FIG. 27B, in some examples the select electrode configurations portion 1720 also may comprise a custom function 1730, which is further described later in association with at least custom engine 1870 in association with at least FIG. 27F (see also FIG. 20). In general terms, the custom function 1730 comprises a mechanism by which many selectable stimulation-related parameters, in addition to stimulation strength (and/or pulse profile), may be evaluated as part of selecting, evaluating, and employing the different electrode configurations 1723A, 1723B, 1723C, 1727A, 1727B, etc. in a method of stimulation programming, a method of delivering stimulation therapy to a patient, etc. It will be further understood that any one of, a combination of, or all of the various engines, parameters, functions, etc. described in association with the custom stimulation parameters engine 1870 of FIG. 27F may be displayed as part of at least the example user interfaces 1700 FIG. 27B, 2050 FIG. 28B, and may be employed in stimulation programming of an IMD 1104, 1134 (according to the methods described throughout the present disclosure), and may be employed as at least part of a configured setting of an IMD 1104, 1134 to deliver stimulation therapy to a patient.

With further reference to FIG. 27A, via a user interface (e.g. 1103 in FIG. 18) at 1612 the method 1600 comprises guiding a clinician to select a value of the stimulation strength and then applying a test stimulation while observing an airway effect (e.g. upper airway opening) of the patient, as shown at 1614 in FIG. 27A. In some examples, the airway effect may comprise a tongue motion (e.g. protrusion, other), among other effects relating to opening the upper airway. In some examples, this aspect of the method 1600 may be implemented via an evaluate airway effect portion 1740 of user interface 1700 in FIG. 27B, which comprises an stimulation strength test function 1468, test stimulation function 1560, and/or stimulation history function 1562 like that shown and previously described in association with FIG. 25B.

As indicated via directional arrow 1616 in FIG. 27A, the method 1600 may comprise guiding the clinician to repeat performing the actions at 1612 and 1614 until a value of the stimulation strength is reached which produces an airway effect similar to the airway effect caused by the current therapy settings (i.e. stimulation settings already programmed into the IPG 1134). At 1618 in FIG. 27A, and via a user interface 1103 (FIG. 18), the clinician may save this determined stimulation strength value, which is then displayed. In some examples, this aspect of method 1600 may be implemented via the save levels portion 1750 of user interface 1700 (FIG. 27B), which includes a "similar to current therapy" function 1760, at which the determined stimulation strength may be saved (via SAVE button) and displayed in an associated window, as shown in FIG. 27B.

As further shown at 1620 in FIG. 27A, the method 1600 comprises guiding the clinician to select and save, via function 1476 in the user interface 1700 of FIG. 27B, an opening descriptor (e.g. airway effect descriptor) corresponding the type and/or degree of upper airway opening observed by the clinician when applying a test stimulation to the patient at the selected/saved stimulation strength at 1618. In some examples, the airway opening may be at least caused by or correspond to a tongue motion (e.g. protrusion, comfortable protrusion, uncomfortable protrusion, and the like).

As further represented by the dashed directional arrow 1630 in FIG. 27A, the method 1600 also may comprise providing the clinician with the option to further evaluate and document the initially selected electrode configuration by further performing the actions at 1612 and 1614 in method 1600 to determine an stimulation strength value at which a functional level of stimulation is observed, as shown via pathway 1635 and at 1640 in FIG. 27A. Again, these aspects (at 1630, 1612, 1614) of the method 1600 may be implemented via the previously-described evaluate airway effect portion 1740 of the user interface 1700 (FIG. 27B). In some such examples, the pathway 1630 may be employed by the clinician when it is believed that the saved stimulation strength and airway effect identified at 1618 and 1620 may be less than a functional level of stimulation and/or when the current therapy settings (e.g. those saved in the IMD 1104, 1134 for nightly therapy) appear to produce therapy which may exhibit less efficacy than desired.

Upon such determination of a functional level, the functional level function 1762 in the save levels portion 1750 of user interface 1700 in FIG. 27B may be used (in a manner similar to function 1760) to save the stimulation strength value at which a functional level was identified.

As shown at 1622 in FIG. 27A, once the evaluation of the first selected electrode configuration has been evaluated as described above, the method 1600 may further comprise providing the clinician with the ability to select another electrode configuration for evaluation as represented via the directional path 1624. However, it will be understood that while the method 1600 offers guidance to potentially evaluate at least second electrode configuration, the clinician may choose to not evaluate additional electrode configurations and may proceed to 1650 in method 1600 in FIG. 27A, which represents the completion of an electrode configuration-by-electrode configuration evaluation of more than one electrode configuration. The dashed box 1651 schematically represents that the evaluation of more than one electrode configuration is optional.

Assuming that the clinician does select another electrode configuration for evaluation at 1622, via path 1624 the method may comprise returning to 1610 at which the second electrode configuration may be selected by the clinician via the user interface 1103 (FIG. 18). Once selected, the method 1600 guides the clinician through the various actions (e.g. 1612, 1614, 1616, 1618, 1620, 1622, and 1630/1640 if desired) for evaluating that particular electrode configuration. Of course, in some example implementations of method 1600, the user interface 1700 in FIG. 27B may be employed to perform these aspects of the method 1600 as described above with respect to both FIGS. 27A and 27B.

In some examples, this portion of the method 1600 (e.g. 1610, 1612, 1614, 1616, 1618, 1620, 1622, 1630/640) is performed for as many electrode configurations that the clinician desires to perform. It will be understood that the various electrode configurations (e.g. 1723A, 1723B, 1723C, 1727A, 1727B represented in FIG. 27B), and as implanted within the patient, may have different positions along a length of the nerve and/or have different positions about a circumference of the nerve (e.g. where the electrode contacts are circumferentially arranged about an outer surface of a nerve when viewed in cross-section). Further details regarding such example arrangement will be later described below in association with at least FIGS. 27C-27H.

Upon completion of the optional electrode configuration-by-electrode configuration evaluation (1650), at 1652 of FIG. 27A the method 1600 comprises guiding the clinician, via the user interface (e.g. 1103 in FIG. 18, 1700 in FIG. 27B), to review and compare, for each evaluated electrode configuration, the airway effect and stimulation strength to determine which electrode configuration(s) and stimulation level may be best suited to provide efficacious therapy for the patient on a nightly basis.

Upon such review and comparison at 1652, via the user interface the method 1600 guides the clinician to select the electrode configuration (at 1654 in FIG. 27A) and the stimulation strength (at 1656 in FIG. 27A) by which the therapy will be applied to the patient with the method further enabling the clinician to potentially cause configuration of the IMD 1104, 1134 (FIGS. 18-19) with the selected electrode configuration and stimulation strength settings, as shown at 1658 in FIG. 27A. As previously noted elsewhere, such potential changes to stimulation settings of an IMD may be subject to consultation with a physician (or other caregiver) prior to implementing a changed settings configuration in the IMD. As shown at 1660, via the user interface the method 1600 displays an indication of completion of the electrode configuration portion 1600 of the advanced follow-up method.

It will be understood that in some examples the method 1600 in FIG. 27A may be implemented without the example method 1530 (FIG. 26) and/or without the example method 900 in FIG. 8A. Conversely, in some examples, the method 1900 in FIG. 28A may be implemented without the example method 1530 and/or without the example method 1600 in FIG. 27A.

FIGS. 27C-27H are diagrams which illustrate at least some example electrode configuration arrangements, nerve arrangements, and/or related parameters for which stimulation programming methods (e.g. 1600 in FIG. 27A; 1900 in FIG. 28A) may be performed, such as but not limited to, in association with user interfaces 1700 in FIG. 27B, and/or 2050, 2100 in FIGS. 28B, 28C.

FIG. 27C is a diagram including a sectional view schematically representing an example arrangement 1800 including an example device and/or example method of providing stimulation to two different types of nerves for increasing and/or maintaining upper airway patency. In some examples, the example arrangement 1800 comprises one example implementation by which stimulation may be delivered to one of, or both, the hypoglossal nerve 1805 and the ansa cervicalis-related nerve 1816. Of course, it will be understood that another airway patency-related nerve (e.g. upper airway patency-related nerve) may take the place of one or both of the hypoglossal nerve 1805 and ansa cervicalis-related nerve 1816 in the example arrangement shown in FIGS. 27C, 27D, 27E.

It will be further understood that the example arrangements in FIGS. 27C-27H are not strictly limited to arrangements including two different types of nerves, but that at least some of the example arrangements relating to FIGS. 27C-27H may be deployed for a single airway patency-related nerve, in some examples.

As shown in FIG. 27C, in some examples the example arrangement 1800 may comprise cuff electrode 1830, which comprises a cylindrically shaped body 1831 defining a lumen 1833 to at least partially enclose or encircle the respective nerves 1805, 1816. As shown in FIG. 27C, in some examples the body 1831 may comprise a slit or re-closable opening 1835 to permit placing the cuff electrode 1830 about the nerve(s) 1805, 1816 and permit re-closure of the wall of the body 1831 about the nerves. While not shown for illustrative simplicity, in some examples the cuff electrode 1830 may comprise overlapping flange members to enhance releasably securing the cuff electrode about the nerves 1805, 1816. Moreover, in some examples, the cuff electrode 1830 comprises an array of circumferentially spaced apart electrodes 1836 exposed on an interior surface 1837 to be in stimulating relation to the respective nerves 1805, 1816. Via various combinations of the electrodes 1836 and selectable parameters (e.g. stimulation strength, pulse profile, current, frequency, duty cycle, sequence of activation, etc.) of a stimulation signal, various fascicles 1809 within the hypoglossal nerve 1805 and/or various fascicles 1813 within the ansa cervicalis-related nerve 1816 may be targeted to effect desired stimulation of at least motor fibers to increase and/or maintain upper airway patency. In some such examples, the various nerves 1805, 1816 (and their various fascicles) may be stimulated according to at least some of the additional stimulation parameters further described below in association with at least FIG. 27F.

FIG. 27D is a diagram 1840 including a side view schematically representing the cuff electrode 1830 in FIG. 27C, and which further illustrates various features and attributes of the cuff electrode 1830. For instance, FIG. 27D illustrates one example configuration of the electrodes 1836 when arranged in an array in which the electrodes 1836 extend in a spaced apart manner axially along a length of the body 1831 of cuff electrode 1830 and extend in a spaced apart manner circumferentially about the interior surface 1837 (FIG. 27C) of the body 1831 of cuff electrode 1830. It will be further understood that FIG. 27D is merely an example, and that it is contemplated that the various electrodes 1836 may be staggered relative to each other in various circumferential positions such that the electrodes 1836 need not be in axial alignment with each other along a longitudinal axis and/or need not be in alignment with each other along a cross-sectional plane extending transverse to a longitudinal axis of the cuff electrode 1830.

FIG. 27E is a sectional view schematically representing an example arrangement 1851 comprising a first cuff electrode 1861 and a second cuff electrode 1862. As shown in FIG. 7E, each cuff electrode 1851, 1861 comprises at least some of substantially the same features and attributes as the cuff electrode 1830 in FIG. 27C-27D, except being sized to at least partially encircle and enclose just one nerve, such as nerves 1805, 1816 respectively instead of two nerves as in FIG. 27C. Accordingly, the features of cuff electrodes 1861, 1862 are identified via similar reference elements as in FIG. 27C-27D.

Via this example arrangement 1851, stimulation of each nerve 1805, 1816 is applied via separate cuff electrodes 1851, 1861 in a side-by-side arrangement, which may simplify at least some aspects of selectively stimulating certain fascicles within each respective nerve 1805, 1816 relating to maintaining and/or increasing airway patency (e.g. upper airway patency) and related physiologic functions.

However, in some examples, the respective nerves 1805 and 1816 may be spaced apart from each other (i.e. not side-by-side), and therefore the respective cuff electrodes 1861, 1862 also would be spaced apart from each other (i.e. not side-by-side).

In some example implementations, the cuff electrodes 1830, 1861, and/or 1862 may comprise at least some of substantially the same features and attributes as described in Bonde et al, SELF EXPANDING ELECTRODE CUFF, issued as U.S. Pat. No. 9,227,053 on Jan. 5, 2016, in Bonde et al, SELF EXPANDING ELECTRODE CUFF, issued as U.S. Pat. No. 8,340,785 on Dec. 25, 2012, in Johnson et al, NERVE CUFF, issued as U.S. Pat. No. 8,934,992 on Jan. 13, 2015, and in Rondoni et al, CUFF ELECTRODE, published as US 2020-0230412 on Jul. 23, 2020, and which are all hereby incorporated by reference.

FIG. 27F is a block diagram schematically representing an example custom stimulation parameter engine 1870. As previously mentioned, the example custom stimulation parameter engine 1870 may comprise one example implementation of the custom function 1730 in FIGS. 27A and 28B, which may in turn drive, support, etc. at least part of a method of stimulation programming (which may include evaluating stimulation programming), a method of delivering stimulation therapy to a patient, etc.

As shown in FIG. 27F, in some examples the custom stimulation programming engine 1730 may comprise a nerve engine 1871, a position engine 1876, and a pattern engine 1880.

As shown in FIG. 27F, in some examples the nerve engine 1871 may comprise a first nerve parameter 1872A, a second nerve parameter 1872B, and other nerve parameter 1872C. In some examples, the respective first, second, and other nerve parameters 1872A, 1872B, 1872C may enable control, tracking, and/or managing application of stimulation to a first nerve, a second nerve, and/or other nerve(s).

Accordingly, when performing a stimulation programming method (e.g. 1600 in FIG. 27A) in association with a user interface (e.g. 1700 in FIG. 27B), a clinician can select which nerve(s) are to be stimulated as part of evaluating one or more selectable electrode configurations, such as via portions 1720, 1722, 1726 of user interface 2700 in FIG. 27B. For instance, via first nerve parameter 1872A, the clinician may select one airway patency-related nerve (e.g. on a first side of the body) for evaluation with any electrode configurations implanted relative to the particular nerve. In a simple example, this nerve may comprise an upper airway patency-related nerve, such as a hypoglossal nerve, an ansa cervicalis-related nerve, and the like. In situations in which the various electrode configurations may be in stimulating relation to more than one nerve, deploying the first nerve parameter 1872A may comprise selecting which nerve is to be evaluated as part of evaluating stimulation programming for the electrode configurations selected for evaluation per user interface 1700 of FIG. 27B.

In some examples, via a second nerve parameter 1872B, a second airway patency-related nerve may be selected for evaluation with any electrode configurations implanted in stimulating relation relative to the particular second nerve.

In some examples, the first and second nerves may be on the same side of the body, and hence, the first and second nerves typically may comprise different types of nerves. For instance, the first nerve may comprise a hypoglossal nerve while the second nerve may comprise an ansa cervicalis-related nerve. Of course, airway patency-related nerves other than the hypoglossal nerve and ansa cervicalis-related nerve may comprise the first nerve or the second nerve selected via parameter 1872A and/or 1872B.

In some examples, the first and second nerves may comprise two different types of airway patency-related nerves and the other parameter 1872C may be used to select a third nerve, which may comprise a third airway patency-related nerve on the same side of the body as the first and second nerves (per parameters 1872A, 1872B). For instance, among other potential nerves, the phrenic nerve may comprise one example of an other nerve.

In some examples, the respective first and second nerves (selected via parameters 1872A, 1872B) may be located on different (i.e. opposite) sides of body. In some examples, the first and second nerves may comprise the same type of nerve related to airway patency, such as both first and second nerves comprising an upper airway patency-related nerve (e.g. hypoglossal nerve or ansa cervicalis-related nerve, and the like) on a first side of the body and a second of the same type of upper airway patency-related nerve (e.g. hypoglossal nerve, ansa cervicalis-related nerve, and the like) on a second side of the body. In some such examples, the two nerves of the same type on different sides of the body may be stimulated according to different patterns, such as at least some of the different stimulation patterns described further in association with pattern engine 1880. In one such example, just one of the respective nerves (of the same nerve type on different sides of the body) may be applied per unilateral parameter 1887A while in some examples, both of the respective nerves (of the same nerve type on different sides of the body) may be evaluated via bilateral parameter 1887B in which both nerves are stimulated. Of course, other parameters such as the simultaneous parameter 1882B, alternating parameter 1882A, etc. also may be applied as well, as further described below, where the nerves on opposite sides of the body may be stimulated simultaneously or alternately, etc.

In some examples, per at least first and second parameters 1872A, 1872B, the two different nerves may comprise two different types of nerves, such as a hypoglossal nerve and an ansa cervicalis-related nerve or any other combination of airway patency-related nerves, including nerves such as a phrenic nerve, etc. In some such examples, the two different types of nerves may be located on the same side of the body (as described above) or may be located on different sides of the body (as described above).

In some examples, during evaluation and adjustment of stimulation programming for electrode configurations (e.g. per method 1600 in FIG. 27A, user interface 1700 in FIG. 27B) relative to a first nerve and a second nerve, via other parameter 1872C a third nerve also can be stimulated as part of the electrode configuration evaluation/adjustment. The third nerve may comprise a third type of nerve (e.g. of a different type than the first and/or second nerves) or may comprise the same nerve type as the first nerve and/or the second nerve.

As further shown in FIG. 27F, in some examples the nerve engine 1871 may comprise a fascicle parameter 1874, an efferent parameter 1875A, and/or a blocking parameter 1875B. Via the fascicle parameter 1874, stimulation programming for a selected electrode configuration(s) (e.g. via method 1600 in FIG. 27A or user interface 1700 in FIG. 27B) may be evaluated according to different fascicles of a nerve or different fascicles of multiple nerves.

In some examples, multiple parameters of engine 1870 may be employed together, such as evaluating electrode configurations in association with different types of nerves on different sides of the body while also evaluating the various electrode configurations relative to different fascicles of a nerve among the different types of nerves being evaluated.

In some examples, per parameter 1875A, the nerve engine 1871 may facilitate evaluating stimulation programming of selected electrode configurations relative to efferent fibers of a nerve which may have both efferent fibers and afferent fibers of a nerve, such as the glossopharyngeal nerve. In some examples, some examples, per parameter 1875B, the nerve engine 1871 may facilitate evaluating stimulation programming of selected electrode configurations relative to certain fibers of a nerve, where there may be an interest in blocking nerve conduction as it relates to enhancing stimulation therapy.

As further shown in FIG. 27F, in some examples the custom stimulation programming engine 1870 may comprise an electrode configuration position engine 1876 by which stimulation programming may be evaluated for selectable electrode configurations (per method 1600 in FIG. 27A, user interface 1700 in FIG. 27B) according a position(s) of the respective electrodes on a carrier body (e.g. cuff body, paddle, etc.) and/or a position relative to a nerve to which the electrode is in stimulating relation. For example, the position engine 1876 may comprise an axial parameter 1877A and a circumferential parameter 877B by which electrodes may be evaluated according the various positions of electrode contacts such as their axial position (e.g. along a carrier body or along the length of a nerve) and/or their circumferential position (e.g. about the circumference of an inner, engaging surface of a carrier body or about the circumference of the nerve being engaged). The cuff electrodes 1830, 1861, 1862 in FIGS. 27C-27E provide just one example of electrodes which may be evaluated in association with at least the axial parameter 1877A and/or circumferential parameter 1877B (of position engine 1876 of custom stimulation programming engine 1870) via the example stimulation programming methods throughout the present disclosure) per selectable electrodes having different axial and/or circumferential positions. In some examples, the position engine 1876 comprises an other parameter 1878 by which stimulation programming may be evaluated for selectable electrode(s) according to other positions depending on the type of nerve, its location in the body, and/or the particular size and/or shape of a carrier body carrying the selectable electrodes for which stimulation programming is being evaluated.

As further shown in FIG. 27F, the custom stimulation programming engine 1870 may comprise a pattern engine 1880 to facilitate evaluating stimulation programming for selectable electrode configurations according to various selectable patterns of stimulation. For instance, in some examples the pattern engine 1880 may comprise an independent parameter 1881A, a supplementary parameter 1881B, an alternating parameter 1882A, a simultaneous parameter 1882B, a body position parameter 1884A, a head/neck position 1884B, an other parameter 1885, a closed loop parameter 1886A, and an open loop parameter 1886B.

In some examples, the independent parameter 1881A may be used in some examples to evaluate the effect (e.g. airway effect, comfort, other) of stimulating two (or more) different nerves independently from each other, regardless of whether such independent stimulation is simultaneous, alternating, other and/or regardless of whether stimulation of just one of such nerves would be adequate alone to restore or maintain a desired airway effect (e.g. patency, tongue protrusion, etc.). The two (or more) different nerves may comprise the same type (e.g. hypoglossal nerve) or different types of nerves (e.g. hypoglossal and ansa-cervicalis-related).

Such independent stimulation stands in contrast to stimulation performed via a supplementary parameter 1881B, for which stimulation programming may be evaluated herein, when the stimulation of a second nerve (e.g. ansa-cervicalis, other) is delivered solely (at least in some instances) in a manner which is supplementary to delivery of stimulation to a first nerve (e.g. hypoglossal nerve), or vice versa. In some examples, the second nerve is stimulated based on an efficacy, duration, etc. of stimulation of the first nerve, or vice versa.

In some examples, stimulating a second nerve in a supplementary manner relative to stimulation of a first nerve also may be based on other factors such as: (1) a body position (parameter 884A); (2) a head-and-neck position (parameter 1884B); (3) whether open loop stimulation (parameter 886B) or closed loop stimulation (parameter 1886A); and/or (4) whether unilateral (1887A) or bilateral (1887B) stimulation; and the like. Accordingly, in some such examples, stimulation of a second nerve, which is supplementary to stimulation of a first nerve, may be initiated, maintained, paused, or terminated based on some, all, or none of the above-identified factors in order to evaluate electrode configuration (e.g. FIGS. 27A-27H), pulse profile (e.g. FIGS. 28A-28C), and/or other aspects (e.g. stimulation strength, etc.) of stimulation therapy via the examples of the present disclosure.

However, it will be understood that, in some examples, at least some of the above-identified factors (e.g. 1884A, 1884B, 1886A, 1886B, etc. in FIG. 27F) may be used without regard to the supplementary parameter 1881B in performing methods of evaluating stimulation programming according to at least some of the examples of the present disclosure described in association with at least FIGS. 18-31.

In some examples, upon its use as part of the at least some examples of the present disclosure, the closed loop parameter 1884A enables evaluating stimulation programming relative to the stimulation being triggered, synchronized, etc.

relative to some aspect of a sensed respiratory waveform or other breathing-related signal.

In some examples, upon its use as part of the at least some examples of the present disclosure, the open loop parameter 1884B enables evaluating stimulation programming relative to the stimulation being delivered to a nerve independent of (i.e. without regard to) a sensed respiratory waveform or other breathing-related signal. In some such examples, use of the open loop parameter 1884B may correspond to there being no respiratory sensing at all. However, in some examples, respiratory sensing may occur but such sensing is not used to trigger, synchronize, etc. the therapy stimulation signal, with such sensed respiratory information being used to determine disease burden information (e.g. AHI), in some examples.

In some examples, use of at least one of the body position parameter 1884A, head-and-neck position parameter 1884B, closed loop parameter 1886A, open loop parameter 1886B (or other factors in FIG. 7F or other Figures herein) in evaluating stimulation programming according to various examples of the present disclosure may be supported via an accelerometer(s) implanted within the patient. The accelerometer(s) may be implanted in a body region, head-and-neck region of the patient, or other location. In some examples, such accelerometer(s) may comprise an example implementation of the sensing component 1142 (FIG. 19) and, in some examples, may be on-board the IMD 1104, 1134 or be physically separate from, but at least in electrical communication with, the IMD 1104, 1134 whether the communication (e.g. connection) is wired or wireless.

In some examples, upon its use as part of the at least some examples of the present disclosure, the unilateral parameter 1887A enables evaluating stimulation programming relative to the stimulation being delivered to just one side (e.g. left side or right side) of the patient's body, whether the stimulation includes stimulation of just one nerve or multiple nerves.

Conversely, in some examples, upon its use as part of the at least some examples of the present disclosure, the bilateral parameter 1887B enables evaluating stimulation programming relative to the stimulation being delivered to both sides of the body (e.g. left and right sides), whether the stimulation includes stimulation of just one nerve or multiple nerves on each side of the patient's body. Moreover, in some examples, when just one nerve is stimulated on a left side of the body and just one nerve is stimulated on a right side of the body, the two respective nerves may be of the same type (e.g. both hypoglossal nerve) or of different types (e.g. one being a hypoglossal nerve, another being ansa-cervicalis nerve or other).

It will be further understood that the various parameters of one engine (e.g. 1871, 1876, 1880 in FIG. 27F) may be employed in conjunction with the various parameters of one of the other respective engines (e.g. 1871, 1876, 1880 in FIG. 27F). For instance, in one non-limiting example, the various parameters of pattern engine 1880 may be employed in conjunction with performing stimulation programming (including evaluating such programming) according to the axial, circumferential, and other parameters 1877A, 1877B, 1878 of position engine 1876 and/or according to the parameters 1872A-1875B of the nerve engine 1871, or vice versa.

With regard to the various parameters of the nerve engine 1871, position engine 1876, and pattern engine 1880 of custom engine 1870, it will be understood that in order to enable activation/use of such parameters and/or to view results of use of such parameters (as part of performing/use of at least some of examples of the present disclosure), in some examples indicators corresponding to each of the respective parameters of the respective engines 1871, 1876, and 1880 may be displayed on one or more of the various user interfaces described and illustrated in association with at least FIGS. 18-31, including at least FIGS. 27B, 28B as previously noted.

It will be understood that in some examples the various parameters, functions, etc. of engine 1870 may be grouped, applied, etc. differently than shown in FIG. 27F, and that various example implementations of engine 1870 may omit some of the parameters, functions, etc. shown in FIG. 27F and/or include parameters, functions, etc. in addition to those shown in FIG. 27F.

FIG. 27G is a sectional view, and FIG. 27H is a side view, schematically representing an example arrangement including a cuff electrode 1890. Cuff electrode 1890 provides another example by which at least the axial parameter 1877A and/or circumferential parameter 1877B (of position engine 1876) of custom stimulation programming engine 1870 may be employed to evaluate stimulation (via the example stimulation programming methods throughout the present disclosure) per selectable electrodes having different axial and/or circumferential positions.

In some examples, the cuff electrode 1890 in FIGS. 27G-27H may comprise at least some of substantially the same features and attributes as the cuff electrodes 1830, 1861, 1862 in FIG. 27C-27D or 27E, except with the cuff electrode 1890 in FIGS. 27G-27H comprising fewer electrodes than the respective cuff electrodes 1830, 1861, 1862 shown in FIGS. 27C-27E. In particular, cuff electrode 1890 comprises a bottom row of axially spaced apart electrodes 1896D and a middle row of circumferentially spaced apart electrodes 1896A, 1896B, 1896D, 1896C. By employing various combinations of the respective electrodes 1896A, 1896B, 1896C, 1896D, as well as variations in the stimulation signal as previously described, this electrode configuration may be used to provide selective stimulation and/or stimulation steering of a stimulation signal relative to different fascicles, nerve fibers, etc. within a nerve about which the cuff electrode 1890 is secured.

It will be understood that application of custom engine 1870 and/or the methods in association with FIGS. 18-30 are not limited to cuff-type carriers for electrode configurations, but may be deployed with respect to paddle-type carriers, axial-type carriers, etc.

FIG. 28A is a flow diagram schematically representing the pulse profile evaluation method 1900. In general terms, via the pulse profile method 1900, the clinician may evaluate the stimulation settings on a pulse profile basis, which provides an evaluation of the general effectiveness of each selectable pulse profile in delivering stimulation (e.g. generally or for a particular electrode configuration(s)) and/or an evaluation (and adjustment) of the particular stimulation settings (and electrode configuration(s) for that particular pulse profile setting.

In some examples, the example method 1900 may be implemented via at least some of substantially the same features and attributes as previously described in association with at least FIGS. 18-27H and the control portion 2400 (FIG. 32A), and a user interface (e.g. 1103 in FIG. 18); 2440 in FIG. 32B).

In some examples, the user interfaces 2050 in FIG. 2B and 2100 in FIG. 28C may comprise a more specific example implementation of user interface 1103 (FIG. 18), which may embody at least some aspects of, and/or facilitate, method 1900 (FIG. 28A). As shown in FIG. 28B, user interface 2050 may comprise a banner 1310 with features (e.g. 1312, 1314) similar to that shown in FIGS. 21, 23, etc. In addition, the user interface 2050 may comprise an evaluate pulse profile portion 2054 and advanced follow-up indicator 2052. The evaluate pulse profile portion 2054 may comprise a select stimulation setting portion 1056, an evaluate airway effect portion 1740, and/or a save levels portion 2064. Further details regarding each of these respective portions 2056, 1740, 2064 will be described below in the context of method 1900 (FIG. 18A).

Accordingly, as shown at 1910 in FIG. 28A and via select stimulation settings portion 2056 of user interface 2050 (FIG. 28B), the example method 1900 comprises selecting for evaluation at least one pulse profile among multiple potential different pulse profiles by which a stimulation signal which may be delivered via a stimulation element (e.g. 1140 in FIG. 19) associated with the IMD 1104, 1134 (FIGS. 18-19). It will be understood that in at least some examples, the method 1600 (FIG. 27A) and method 1900 (FIG. 28A) cooperate so that evaluation (and potential adjustment) of the pulse profile settings via method 1900 (FIG. 28A) are performed with selected electrode configuration(s) (e.g. 1723A-1723C, 1727A-1727B) from user interface 1700 (FIG. 27B).

As further shown in FIG. 28B, in some examples the select stimulation settings portion 2056 may display current stimulation settings, such as which pulse profile (e.g. pulse width/rate such as 90/33) and which stimulation strength setting (e.g. amplitude 0.5 V) are currently configured in the IMD 1104, 1134. In examples in which the pulse profile is expressed via pulse width/rate parameter, the pulse width/rate refers to the pulse width (e.g. 90, such as duration in microseconds of a group of pulses), and refers to the rate (e.g. 33 Hz, such as the number of pulses delivered per second) at which the stimulation signal is delivered to the patient via the selected electrode configurations.

As further shown in FIG. 28B, in some examples the select stimulation settings 2056 may further comprise a plurality 2060 (e.g. array) of selectable pulse profile settings 2062 along with a selection indicator 2063 for each different setting. Each different setting 2062 (e.g. 1, 2, 3, 4, 5) corresponds to a different pulse profile setting such as (but not limited to) pulse width/rate settings of 90/33, 120/33, 120/40, 150/33, and 60/40.

As shown in FIG. 28B, in a manner similar to the user interface 1700 in FIG. 27B, in some examples the select stimulation settings portion 2056 also may comprise a custom function 1730 by which the different pulse profile settings (in association with a selected electrode configuration) may be further evaluated.

At 1912 in FIG. 28A, the method 1900 comprises guiding the clinician to select a value of the stimulation strength and then applying a test stimulation while observing an airway effect (e.g. degree and/or type of airway opening) of the patient, as shown at 1914 in FIG. 28A. In some examples, this aspect of the method 1900 may be implemented via an evaluate airway effect portion 1740 of user interface 2050 in FIG. 28B, which comprises an stimulation strength test function 1468, test stimulation function 1560, and/or stimulation history function 1562 like that shown and previously described in association with FIGS. 25B, 27B.

As indicated via directional arrow 1916, the method 1900 may comprise guiding the clinician (e.g. via the user interface 1103 (FIG. 18) to repeat performing the actions at 1912 and 1914 until a value of the stimulation strength is reached which produces an airway effect similar to an airway effect caused by the current therapy settings (i.e. stimulation settings already programmed into the IMD 1104, 1134). At 1918 in FIG. 28A, and via the user interface (e.g. 1103 in FIG. 18), the method 1900 guides the clinician to save the stimulation strength value, which may be displayed. In some examples, this aspect of method 1900 may be implemented via the save levels portion 2064 of user interface 2050 in FIG. 28B, which includes a "similar to current therapy" function 1760, at which the determined stimulation strength may be saved (via SAVE button) and displayed in an associated window, as shown in FIG. 28B.

As further shown at 1920, the method 1900 comprises guiding the clinician to select and save, via function 1476 in the user interface 2050 of FIG. 28B, an opening descriptor corresponding the type and/or degree of airway effect (e.g. airway opening) observed by a clinician when applying a test stimulation signal to the patient at the stimulation strength (and for a selected pulse profile) selected/saved at 1918 in FIG. 28A. In some examples, the airway effect descriptors may include, but are not limited to, descriptors relating to tongue motion (e.g. protrusion, comfortable protrusion, uncomfortable protrusion, and the like) observed by the clinician when applying a test stimulation at the selected/saved stimulation strength for a given pulse profile.

As further represented by the dashed directional arrow 1930 in FIG. 28A, in some examples the method 1900 also may comprise providing the clinician with the option to further evaluate and document the initially selected pulse profile by further performing the actions at 1912 and 1914 in method 1900 to determine an stimulation strength value at which a functional level of stimulation is observed, as further schematically represented via arrow 1935 and dashed box 1940 in FIG. 28A. Again, these aspects (at 1930, 1912, 1914) of the method 1900 may be implemented via the previously-described evaluate airway effect portion 1740 of the user interface 2050 in FIG. 28B. In some such examples, the pathway 1930 may be employed by the clinician when it is believed that the saved stimulation strength and airway effect identified at 1918 and 1920 may be less than a functional level of stimulation and/or when the current therapy settings (e.g. those saved in the IMD 1104, 1134 for nightly therapy) appear to produce therapy which may exhibit less efficacy than desired.

Upon such determination of a functional level, the functional level function 1762 in the save levels portion 2064 of user interface 2050 in FIG. 28B may be used (in a manner similar to function 760 to save the stimulation strength value at which a functional level was identified.

As shown at 1922 in FIG. 28A, once the evaluation of the first selected pulse profile has been evaluated as described above, the method 1900 may further comprise guiding the clinician in selecting another pulse profile for evaluation as represented via the directional path 1924. However, it will be understood that while method 1900 offers guidance to evaluate at least a second pulse profile, the clinician may choose to not evaluate additional pulse profile settings and may proceed to action 1950 in method 1900 in FIG. 28A. Stated differently, evaluating a second or third or more pulse profile is wholly optional and need not be performed, as schematically represented via dashed box 1923.

Assuming that the clinician selects another pulse profile for evaluation at 1922, via path 1924 the method comprises returning to 1910 at which the second pulse profile may be selected via the user interface 2050 in FIG. 28B (or 1103 in FIG. 18). Once selected, the method 1900 guides the clinician through the various actions (e.g. 1912, 1914, 1916, 1918, 1920, 1922, 1930/1940 if desired) for evaluating that particular pulse profile.

Via the user interface 2050 in FIG. 28B, this portion of the method 1900 (e.g. 1910, 1912, 1914, 1916, 1918, 1920, 1922, 1930/1940) is performed for as many different pulse profile settings 2062 (e.g. at select stimulation settings portion 2056 of user interface 2050) that the clinician desires to perform.

Upon completion of the evaluation of at least some of the various selectable pulse profiles (at 1950 in FIG. 28A), at 1952 the method 1900 comprises guiding the clinician (via a user interface 2050 in FIG. 28B, 2100 in FIG. 28C) to review and compare, for each evaluated pulse profile, the airway effect and stimulation level to determine which pulse profile and stimulation level may be best suited to provide efficacious therapy for the patient on a nightly basis. In some examples, at least some aspects of this review and comparison may be performed via user interface 2050 (FIG. 28B) and/or via user interface 2100 in FIG. 28C.

In some examples, the user interface 2100 in FIG. 28C may comprise at least some of substantially the same features and attributes as interface 1550 of FIG. 25B, except further comprising an advanced settings portion 2130. As shown in FIG. 28C, the advanced settings portion 2130 may comprise a pulse profile function (e.g. a pulse width function 2132, a rate function 2134), and an electrode configuration function 2136. Each of the respective functions 2132, 2134 include buttons for increasing (up arrow) and for decreasing (down arrow) the selectable value of the pulse width, which is displayed in a nearby window. Meanwhile the electrode configuration function 2136 includes a displayed electrode configuration, such as the selected anode/cathode configuration, etc.

Accordingly, via the user interface 2100 in FIG. 28C, the clinician may review the stimulation settings 1556, timing settings 1580, and/or advanced settings 2130. As part of method 1900, recommended stimulation settings for stimulation strength may be displayed in the window at 1468, along with the lower and upper stimulation strength limits displayed in the associated window at 1572, 1574. In addition, recommended timing settings may be displayed for a start delay in the window at 1582, for pause time in the window at 1584, and/or therapy duration in the window at 1586. Finally, recommended advanced stimulation settings may be displayed for a pulse width in the window at 2132, for a stimulation rate in the window at 2134, and/or for a therapy duration in the window at 2136.

Upon completion of the review and comparison at 1952 in FIG. 28A (via user interfaces 2050, 2100 in FIGS. 28B, 28C), the method 1900 guides the clinician to select the pulse profile (at 1954) and the stimulation level (e.g. stimulation strength) at 1956 by which the therapy will be applied to the patient.

Via the user interface 2100 in FIG. 28C, at 1958 in FIG. 28A the method 1900 guides the clinician with the option to potentially authorize the programmer 1102 to configure the IMD 1104, 1134 via CONFIGURE function (e.g. 1326 in FIG. 28C) according to the final stimulation strength and timing settings. As previously noted, the potential configuration of changed settings may be subject to consultation with a physician or other caregiver. As indicated at 1960 in FIG. 28A, this action completes the method 1900 to evaluate and adjust a pulse profile of a stimulation therapy signal.

In some examples, the method 1900 may return the clinician to a home screen (e.g. 1300 in FIG. 21), via selecting HOME SCREEN button 1554 in user interface 2100 in FIG. 28C, where the clinician may choose another programming method (e.g. 1346) or may complete their evaluation/programming session for the particular patient by EXIT function 1313 (FIG. 21).

Figures 29, 30A:
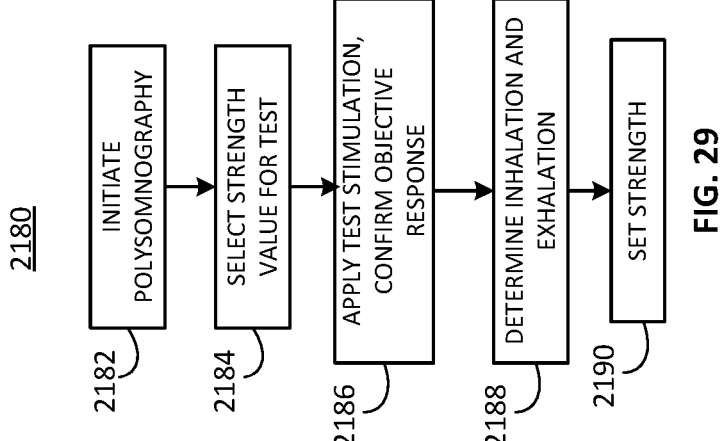
FIG. 29 is a flow diagram schematically representing an example method of stimulation programming, including sleep study preparation.
FIG. 30A is a flow diagram schematically representing an example method of stimulation programming, including evaluating therapy efficacy during a sleep study.

FIGS. 29 and 30A are flow diagrams schematically representing at least some aspects of example sleep study programming methods 2180, 2200. In general terms, these methods 2180, 2200 facilitate a clinician to use a sleep study as a vehicle to evaluate efficacy of patient therapy for particular settings (e.g. stimulation strength, other) of the therapy.

Prior to evaluating the stimulation programming via a sleep study method, a more general method may comprising guiding or suggesting the clinician to review the stimulation and timing settings, while considering feedback from the patient as well as any tracking information from the IMD 1134 regarding performance of the IMD 1134, effectiveness of the therapy, and the like. As previously noted, in some examples this may be implemented via a home screen (via engine 1211) displayed via the user interface 1103 (FIG. 18). Of course, in some examples, the clinician also may take such actions without guidance from an example method.

Among other information, a home screen displayed on the user interface 1103 (FIG. 18) may display any stimulation strength changes that the patient has selected (within a permitted range such as lower limit 1240 and upper limit 1242 in FIG. 20) during the ordinary course of employing the therapy on a nightly basis, usage hours, and the like. In some examples, such patient changes, certain usage data, etc. since the patient's last visit may be highlighted in the user interface 1103 via flags or other indicators to catch the clinician's attention in reviewing the stimulation and timing settings. In some examples, the home screen user interface 1300 in FIG. 21 provides one example implementation which comprises at least some of the above-described features and attributes.

Moreover, in some examples, prior to performing the sleep study method 2200 in FIG. 30A, at least some example implementations comprise performing a preparatory method, such as represented via FIG. 29.

Accordingly, as shown at 2182 in FIG. 29, an example preparatory method 2180 may comprise initiating polysomnography (PSG) and then the clinician selecting a stimulation strength value for a test stimulation burst, as shown at 2184 in FIG. 29. At 2186, the method 2180 may comprise the clinician applying a test stimulation burst and observing objective signs of a response, such as visible contraction visible at the chin or submental EMG signal.

In some examples, at 2188 the preparatory method 2180 comprises determining an inhalation and exhalation on the polysomnography, such as via a nasal pressure cannula or nasal/oral thermistor.

As further shown at 2190 in FIG. 29, the example preparatory method 2180 may further comprise guiding the clinician to set the stimulation strength (of the stimulation to be delivered during the sleep study) according to the selected stimulation strength value. It will be understood that the "set" stimulation strength generally may not correspond the value of the stimulation strength at which the IPG 1134 was configured for on-going therapy, and that the "set" stimulation strength (2190) is for purposes of the sleep study method 2200 (FIG. 30A). In some examples, once the sleep study method has ended, the IMD 1104, 1134 would be operated according to its previous stimulation strength settings unless the clinician took affirmative action via the programmer 1102 to configure the IMD 1104, 1134 with different settings.

With this in mind, FIG. 30A schematically represents one example sleep study method 2200 which may follow the preparatory method 2180 in FIG. 29. However, in some examples, the method 2200 may be performed after different preparatory steps.

In some examples, a clinician may start the sleep study method 2200 of FIG. 30A via the START button 1344 associated with the sleep study function 1346 in the programming portion 1340 of the home screen user interface 1300 in FIG. 21.

In some examples the method 2200 in FIG. 30A may be considered as comprising two portions 2210, 2240 as represented by the respective left and right dashed boxes in FIG. 30A. As shown at 2202 in FIG. 30A, the first portion 2210 of the example method 2200 comprises the clinician to begin the sleep study method by turning therapy on after the patient has fallen asleep. It will be understood that the polysomnography is still on-going after having been initiated in the preparatory method 2180 in FIG. 29.

With further reference to 2204 in FIG. 30A, in some examples the first portion 2210 of method 2200 may comprise the clinician reviewing the patient's sleep history including identifying which sleep positions and/or sleep stages appear to correspond to the highest incidence of obstructive events (e.g. highest apnea-hypopnea index (AHI)). With this information, the clinician may target evaluation of efficacy of the stimulation therapy (during the sleep study) relative to the identified sleep positions and/or sleep stages.

Because the stimulation strength was set (1190) in the preparatory method 2180 (FIG. 29), the patient is asleep, and the therapy is on, then an initial pass in method 2200 in FIG. 30A may skip the actions at 2212, 2214 to proceed to 2220 in FIG. 30A at which the method may comprise the clinician observing the behavior (e.g. breathing, sleep, etc.) of the patient during the sleep study.

In observing the patient's behavior, at 2225 of the method 2200 (via path 2222, 2224) includes the clinician observing whether the patient experiences persistent obstructive (sleep apnea) events while stimulation therapy is ON during the sleep study. If an acceptable number or frequency of obstructive events is observed, the path 2230 in FIG. 30A is followed by which the clinician (at 2220) continues observing the patient's sleep behavior according to the sleep study in progress.

However, if at 2220 of the portion 2210 of method 2200, the clinician observes persistent obstructive (sleep apnea) events occurring (at 2225), then the method comprises following path 2232 which guides the clinician, via the user interface 1103, to select an increased stimulation strength value (at 2212) and then at 2214, to set the selected stimulation strength to be delivered via the IMD 1104, 1134 (FIGS. 18-19). Again, at 2220 the clinician observes the patient's behavior (e.g. airflow response, sleep, and the like) for a period of time (e.g. at least ten minutes) and re-evaluates the effectiveness of the increased stimulation strength value such as whether persistent obstructive events are observed (at 2225).

If the persistence of obstructive events has dissipated, then the method comprises following path 2230 whereupon, at 2220, the clinician continues observing the patient's sleep behavior without immediately making an adjustment to the stimulation strength value. This pattern (i.e. following path 2230 in FIG. 30A) may be maintained repeatedly, so long as persistent obstructive events are not observed again.

On the other hand, if persistent obstructive events are still being observed (at 2225) despite the recent increase in the stimulation strength value of stimulation, then via path 2232, the method 2200 comprises returning to block 2212 at which the clinician is to again select, via the user interface 1103 (FIG. 18), an increased value of the stimulation strength and set the stimulation strength (2214) for the therapy. Via the method, at 2220 the clinician again observes the patient's breathing behavior during sleep after waiting a period of time (e.g. 10 minutes) for the stimulation therapy to be applied at the revised stimulation strength setting and then re-evaluates the effectiveness of the therapy.

In some examples, based on the clinician's observations and adjustments to the stimulation strength, the clinician determines whether a change in the configured setting of stimulation strength for the IMD 1134 should be implemented, as will further described later.

Figure 30B:
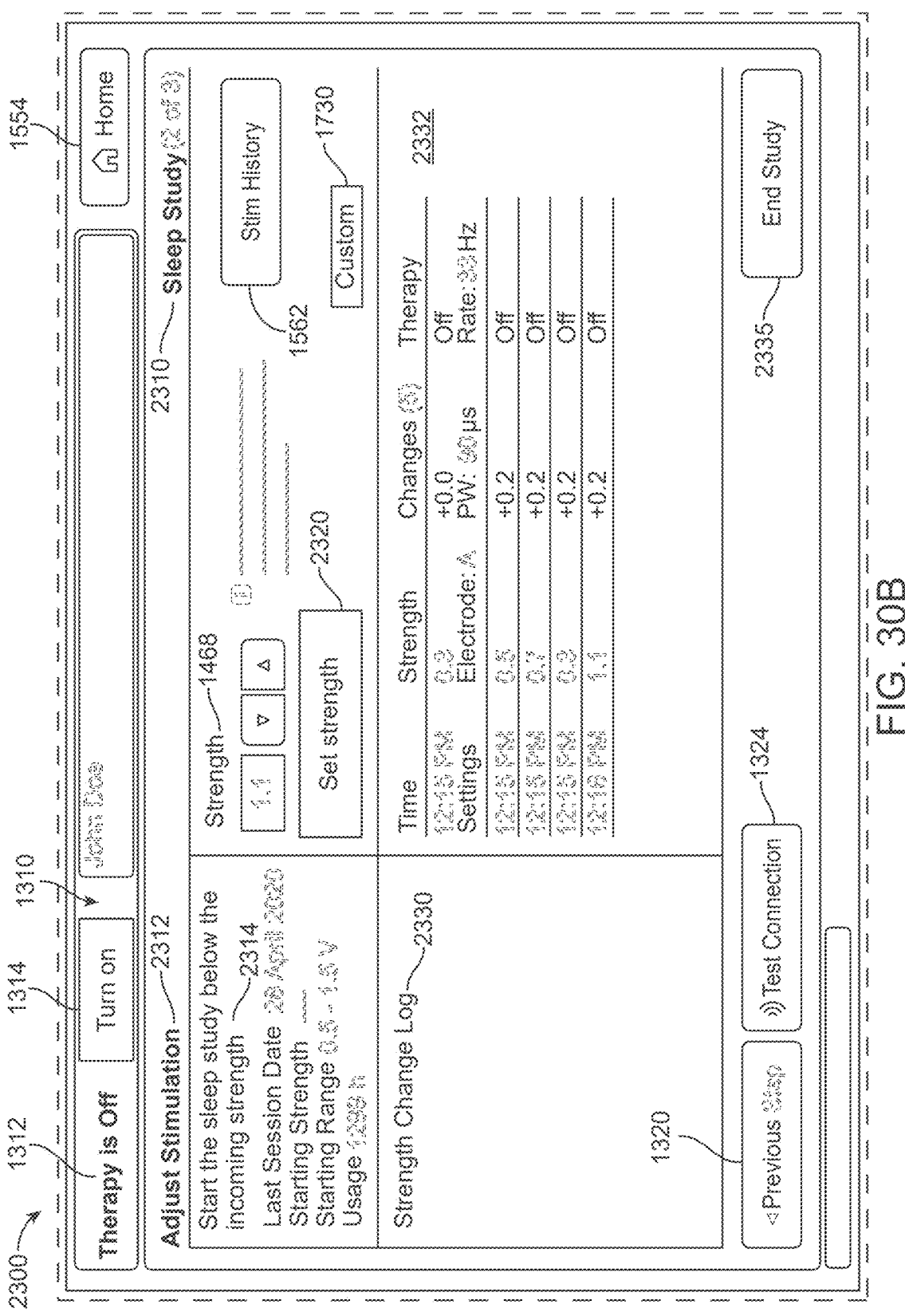
FIG. 30B is a diagram schematically representing an example user interface for stimulation programming with respect to a sleep study.

As shown in FIG. 30B, a sleep study user interface 2300 provides one example implementation of user interface 1103 (FIG. 18) which may embody at least some aspects of, and/or facilitate performance of, the sleep study method 2200 in FIG. 30A. In one aspect, user interface 2300 comprises a banner 1310 as in prior described user interfaces, and additionally including an adjust stimulation indicator 2312 and a sleep study method indicator 2310. In some examples, the user interface 2300 comprises a stimulation strength evaluation portion 2314 and a stimulation strength change log portion 2330. As shown in FIG. 30B, in some examples the stimulation strength evaluation portion 2314 may display a last session date, starting stimulation strength, starting stimulation strength range, and usage indicator (e.g. average number of hours of stimulation therapy per night). The stimulation strength evaluation portion 2314 may further comprise a stimulation strength function 1468 similar to other example user interfaces, along with a set stimulation strength function 2320. Via stimulation history function 1562, a clinician may review a history of stimulation settings, etc. In a manner similar to the previously described example methods (e.g. in FIGS. 27A, 28A, etc.), the stimulation strength evaluation portion 2314 may be used to adjust a value of the stimulation strength and set/apply the adjusted stimulation strength during stimulation therapy as part of the sleep study method 2200 (FIG. 30A).

As further shown in FIG. 30B, the stimulation strength change log portion 2330 of user interface 2300 may comprise a listing 2332 of stimulation strength changes, their magnitude, time stamp, therapy (e.g. on/off), as well as any associated changes in a pulse profile setting for particular electrode configurations, and the magnitude in change of the pulse profile setting. Among other aspects, this information may facilitate a clinician in performing the method 2200 regarding evaluating various stimulation settings relative to observing stimulation therapy, airway effects, etc. during the sleep study.

Figure 30C:
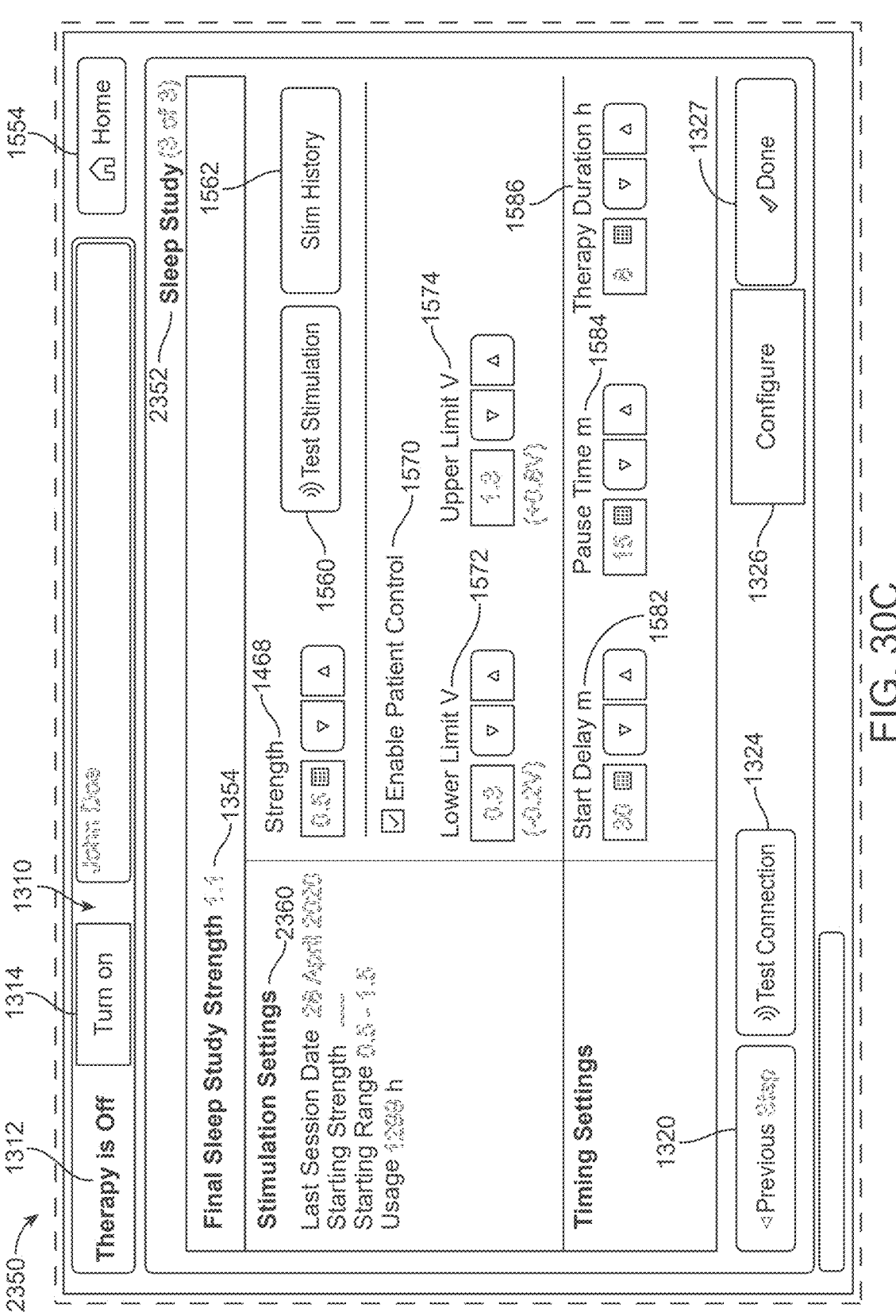
FIG. 30C is a diagram schematically representing an example user interface providing a summary of stimulation and timing settings regarding a sleep study.

FIG. 30C provides another example user interface 2350 related to the sleep study method 2200 (FIG. 30A), which may comprise at least some of substantially the same features and attributes as example user interfaces 1495 in FIGS. 24, 1550 in FIG. 25B, etc., except being related more directly to displaying actions and results relating to the sleep study method 2200 (FIG. 30A), while also enabling configuration of the IMD 1104, 1134 (via CONFIGURE function 1326 in FIG. 30C) according to any final stimulation settings and timing settings determined from the sleep study method 2200 in FIG. 30A.

As shown in FIG. 30A, in some examples the sleep study method 2200 also may comprise a second portion 2240 which addresses situations in which the patient may awaken (e.g. sleep disturbance, neurological arousal, and the like) during the sleep study potentially in response to changes in the stimulation strength values. For instance, assuming therapy is being applied (e.g. ON) at a particular stimulation strength setting and while the clinician is observing the patient's breathing behavior during sleep (at 2220) in portion 2210 of method 2200, as represented by arrow 2243 the patient may experience interrupted sleep (e.g. awake) at 2244 possibly because of the stimulation strength, then as part of portion 2240, method 2200 may comprise proceeding on path 2248 by which the clinician is to turn the therapy OFF (at 2250).

However, in some examples, at 2250 instead of turning the therapy completely OFF, the clinician may reduce the stimulation strength and continue delivering stimulation therapy, and then proceed with method 2200 at 2252 (as part of second portion 2240) as further described below. In some such examples, the reduction in stimulation strength may be sufficient to at least reduce or eliminate the sleep disturbances.

At 2252, the method 2200 may comprise guiding the clinician to select a decreased stimulation strength value and set the stimulation strength at the new, decreased value at 2254. At 2256, the clinician waits for the patient to fall asleep again. Once the patient has resumed sleep, per the portion 2240 of method 2200, the clinician is to re-start therapy (e.g. ON) at 2258, and observe the patient's breathing behavior (at 2220). If the patient no longer awakens (e.g. neurological arousal) (at 2244) with the decreased stimulation strength value, then portion 2240 of method 2200 may comprise following path 2246 by which the clinician continues observing the patient's breathing behavior (at 2220) for the particular stimulation strength setting.

On the other hand, if the patient still experiences interrupted sleep (at 2244), then portion 2240 of method 2200 may comprise following path 2248 for the clinician to again decrease the stimulation strength value of the stimulation (via 2250, 2252, 2254, 2256, 2258) and re-observing the patient's behavior.

Regarding portion 2240 of method 2200, it will be further understood that the observation of the patient's behavior at 2220 also may lead to an observation of the persistence of obstructive events (at 2225), in which case, performing method 2200 may comprise performing the actions along path 2232, etc. as previously described above.

With this method 2200 (FIG. 30A) in mind, it will be understood that the evaluation of the stimulation strength value (relative to therapy efficacy) may occur without the clinician having to adjust the stimulation strength value, such as might be the case if interrupted sleep (e.g. sleep disturbances, awakenings, etc.) had occurred. Accordingly, in such examples, an upper limit of stimulation may be confirmed or re-set without the patient having experienced an awakening, such that an identified upper limit (of stimulation strength values) may not correspond to a stimulation strength value which causes sleep disturbances.

It will be understood that the clinician may also adjust other parameters of stimulation therapy during the sleep study, such as which electrode configurations are being activated, which pulse profile is being applied, etc., with such changes being made at the same time as an adjustment in the stimulation strength is being made or at a time different than adjustments in the stimulation strength are being made.

At the completion of the portion 2210 and/or portion 2240 of method 2200, the entire method 2200 in FIG. 30A may conclude with a user interface 2350 in FIG. 30C displaying the final settings (e.g. stimulation strength value, etc.) and may also display a recommendation for changing the lower limit and upper limit 1572, 1574 of stimulation strength.

Using this information, the method 2200 may conclude with the clinician implementing a CONFIGURE function (e.g. 1326 in FIG. 30C) to cause the new settings for a lower limit and/or upper limit to be configured in the IMD 1104, 1134 (FIGS. 18-19) for use in therapy. However, in some examples, if any change in the stimulation strength setting (e.g. regarding lower and upper limits) is recommended or desired to be implemented, the method may comprise directing the clinician to consult a managing physician and/or other caretaker prior to a changed stimulation strength setting (e.g. regarding the lower and upper limits) being configured in the IMD 1104, 1134 for future therapy.

It will be understood that in some examples the recommendations provided via user interface 11350 may comprise a recommendation to change a stimulation strength setting, which then may be configured in the IMD 1104, 1134. However, in some such examples, no change in the configuration will be implemented without consultation with a managing physician.

Finally, the method 2200 may terminate upon the clinician selecting, via the user interface 2350 in FIG. 30C, a DONE function 1327 or END function, upon which the clinician is returned to home screen user interface 1300 (FIG. 21). The home screen user interface 1300 may indicate that the sleep study method 2200 has been completed or is done. In some examples, the home screen user interface 1300 (FIG. 21) and/or the sleep study user interface 2350 (FIG. 30C) also may indicate a date on which the sleep study was completed for future reference in case future sleep study evaluations (regarding therapy effectiveness) are performed on the patient.

Figure 31:
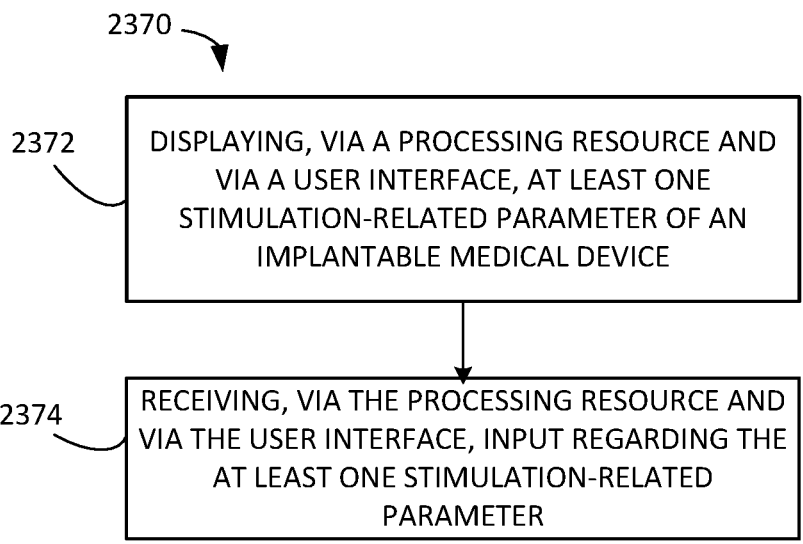
FIG. 31 is a flow diagram of an example method.

FIG. 31 is a flow diagram schematically representing an example method 2370. In some examples, method 2370 may be implemented via at least some the example arrangements, devices, methods, engines, parameters, functions, user interfaces, control portions, etc., as described in association with at least FIGS. 18-30C. In some examples, method 2370 may be implemented via at least some arrangements, devices, methods, engines, parameters, functions, user interfaces, control portions, etc. other than those described in association with at least FIGS. 18-30C.

As shown at 2372 in FIG. 31, in some examples method 2370 comprises displaying, via a processing resource and on a user interface, at least one stimulation-related parameter of an implantable medical device. As shown at 2374 in FIG. 31, in some examples method 3370 comprises receiving, via the processing resource and the user interface, input regarding the at least one stimulation-related parameter. In some examples, the method may comprise further display of the at least one stimulation-related parameter based on the input. In some examples, the input may comprise modifying the at least one stimulation-related parameter to change a configuration of the stimulation settings of the implantable medical device. In some examples, the method 2370 may comprise treating a patient according to the at least one stimulation-related parameter, with the treatment including delivering stimulation therapy via the implantable medical device, in some examples.

FIG. 32A is a block diagram schematically representing an example control portion 2400. In some examples, control portion 2400 provides one example implementation of a control portion forming a part of, implementing, and/or generally managing the example arrangements, the implantable medical devices (IMDs) (e.g. IPG), stimulation elements, sensing elements, programmers, user interfaces, control portion, instructions, engines, functions, parameters, and/or methods, as described throughout examples of the present disclosure in association with FIGS. 18-31. In some examples, control portion 2400 includes a controller 2402 and a memory 2410. In general terms, controller 2402 of control portion 2400 comprises at least one processor 2404 and associated memories. The controller 2402 is electrically couplable to, and in communication with, memory 2410 to generate control signals to direct operation of at least some of the example arrangements, IMDs, stimulation elements, sensing elements, programmers, user interfaces, control portion, instructions, engines, functions, parameters, and/or methods, as described throughout examples of the present disclosure. In some examples, these generated control signals include, but are not limited to, employing instructions 2411 and/or information 2412 stored in memory 2410 to at least direct and manage sleep disordered breathing (SDB) care (e.g. sensing, stimulation, etc.) in the manner described in at least some examples of the present disclosure, such as but not limited to methods for programming an IMD. In some such examples, the methods may comprise guiding a clinician via user interfaces to perform the stimulation programming, evaluate stimulation programming, and the like. In some instances, the controller 2402 or control portion 2400 may sometimes be referred to as being programmed to perform the above-identified actions, functions, etc.

In response to or based upon commands received via a user interface (e.g. user interface 2440 in FIG. 32B or 1103 in FIG. 18) and/or via machine readable instructions, controller 2402 generates control signals as described above in accordance with at least some of the examples of the present disclosure. In some examples, controller 2402 is embodied in a general purpose computing device while in some examples, controller 2402 is incorporated into or associated with at least some of the example arrangements, IMDs, stimulation elements, sensing elements, programmers, user interface, control portion, instructions, engines, functions, parameters, and/or methods, etc. as described throughout examples of the present disclosure.

For purposes of this application, in reference to the controller 2402, the term "processor" shall mean a presently developed or future developed processor (or processing resources) that executes machine readable instructions contained in a memory or that includes circuitry to perform computations. In some examples, execution of the machine readable instructions, such as those provided via memory 2410 of control portion 2400 cause the processor to perform the above-identified actions, such as operating controller 2402 to implement sleep disordered breathing (SDB) care (including stimulation programming for an IMD) via the various example implementations as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by memory 2410. The machine readable instructions may include a sequence of instructions, a processor-executable machine learning model, or the like. In some examples, memory 2410 comprises a computer readable tangible medium providing non-volatile storage of the machine readable instructions executable by a process of controller 2402. In some examples, the computer readable tangible medium may sometimes be referred to as, and/or comprise at least a portion of, a computer program product. In other examples, hard wired circuitry may be used in place of or in combination with machine readable instructions to implement the functions described. For example, controller 2402 may be embodied as part of at least one application-specific integrated circuit (ASIC), at least one field-programmable gate array (FPGA), and/or the like. In at least some examples, the controller 2402 is not limited to any specific combination of hardware circuitry and machine readable instructions, nor limited to any particular source for the machine readable instructions executed by the controller 2402.

In some examples, control portion 2400 may be entirely implemented within or by a stand-alone device.

In some examples, the control portion 2400 may be partially implemented in one of the example arrangements, IMDs, stimulation elements, sensing elements, programmers, etc. and partially implemented in a computing resource separate from, and independent of, the example arrangements, IMDs, stimulation elements, sensing elements, programmers, etc. but in communication with such example arrangements, etc. For instance, in some examples control portion 2400 may be implemented via a server accessible via the cloud and/or other network pathways. In some examples, the control portion 2400 may be distributed or apportioned among multiple devices or resources such as among a server, an example arrangement, and/or a user interface.

In some examples, control portion 2400 includes, and/or is in communication with, a user interface 2440 as shown in FIG. 32B. In some examples, user interface 2440 comprises a user interface or other display that provides for the simultaneous display, activation, and/or operation of at least some of the example arrangements, IMDs, stimulation elements, sensing elements, programmers, user interface, control portion, instructions, engines, functions, parameters, and/or methods, etc., as described in association with FIGS. 18-31. For instance, user interface 2440 may comprise one example implementation of user interface 1103 in FIG. 18. In some examples, at least some portions or aspects of the user interface 2440 are provided via a graphical user interface (GUI), and may comprise a display 2442 and input 2444.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. A wireless communications assembly for providing a communications link between a programmer and an implantable medical device, the wireless communications assembly comprising:

a programmer head configured to establish wireless communications with an implantable medical device, wherein the programmer head includes a housing maintaining an antenna and is characterized by the absence of a wireless communications-related electrical component apart from the antenna;

a controller configured to establish wireless communications with a programmer; and a cable extending between electrically connecting the programmer head and the controller;

wherein the wireless communications assembly is configured to facilitate communications between the programmer and the implantable medical device.

2. The wireless communications assembly of claim 1, wherein the controller includes a processor programmed to receive and act upon a signal from the antenna as part of a telemetry communications operation.

3. The wireless communications assembly of claim 1, wherein the housing defines a placement region containing the antenna and adapted for placement on a patient.

4. The wireless communications assembly of claim 1, wherein the programmer head includes a telemetry strength display indicative of a strength of telemetry connection between the antenna and an IMD.

5. The wireless communications assembly of claim 4, wherein the telemetry strength display is configured to generate a display indicating one of a strong telemetry connection, a moderate strength telemetry connection, and a low strength telemetry connection.

6. The wireless communications assembly of claim 1, wherein the programmer head includes an EMI display indicative of electrical noise interfering with a possible telemetry connection between the antenna and an IMD.

7. The wireless communications assembly of claim 6, wherein the EMI display includes an illuminated icon.

8. The wireless communications assembly of claim 1, wherein the controller includes a case maintaining a communication test button.

9. The wireless communications assembly of claim 8, wherein the controller further includes a sensor associated with the communication test button and a processor programmed to perform a telemetry test operation in response to activation of the sensor by the communication test button.

10. The wireless communications assembly of claim 9, wherein the telemetry test operation includes prompting the antenna of the programmer head to attempt to wirelessly communicate with an implantable medical device.

11. A wireless communications assembly for providing a communications link between a programmer and an implantable medical device, the wireless communications assembly comprising:

a programmer head configured to establish wireless communications with an implantable medical device, wherein the programmer head includes a housing maintaining an antenna;

a controller configured to establish wireless communications with a programmer, wherein the programmer head includes a telemetry strength display indicative of a strength of telemetry connection between the antenna and an IMD; and a cable extending between electrically connecting the programmer head and the controller;

wherein the wireless communications assembly is configured to facilitate communications between the programmer and the implantable medical device.

12. The wireless communications assembly of claim 11, wherein the telemetry strength display is configured to generate a display indicating one of a strong telemetry connection, a moderate strength telemetry connection, and a low strength telemetry connection.

13. The wireless communications assembly of claim 12, wherein the telemetry strength display includes a first, second and third bar icons.

14. The wireless communications assembly of claim 11, wherein the programmer head includes a first light emitting device arranged to illuminate the first bar icon, a second light emitting device arranged to illuminate the second bar icon, and a third light emitting device arranged to illuminate the third bar icon.

15. The wireless communications assembly of claim 12, wherein the telemetry strength display is further configured to generate a display indicating no telemetry connection.

16. A wireless communications assembly for providing a communications link between a programmer and an implantable medical device, the wireless communications assembly comprising:

a programmer head configured to establish wireless communications with an implantable medical device, wherein the programmer head includes a housing maintaining an antenna, and further wherein the programmer head includes an EMI display indicative of electrical noise interfering with a possible telemetry connection between the antenna and an IMD;

a controller configured to establish wireless communications with a programmer; and a cable extending between electrically connecting the programmer head and the controller;

wherein the wireless communications assembly is configured to facilitate communications between the programmer and the implantable medical device.

17. The wireless communications assembly of claim 16, wherein the EMI display includes an illuminated icon.

18. The wireless communications assembly of claim 16, wherein the programmer head further includes a telemetry strength display indicative of a strength of telemetry connection between the antenna and an IMD.

19. The wireless communications assembly of claim 18, wherein telemetry strength display is configured to generate a display indicating one of a strong telemetry connection, a moderate strength telemetry connection, and a low strength telemetry connection.

20. A wireless communications assembly for providing a communications link between a programmer and an implantable medical device, the wireless communications assembly comprising:

a programmer head configured to establish wireless communications with an implantable medical device;

a controller configured to establish wireless communications with a programmer, wherein the controller includes a case maintaining a communication test button; and a cable extending between electrically connecting the programmer head and the controller;

wherein the wireless communications assembly is configured to facilitate communications between the programmer and the implantable medical device.

21. The wireless communications assembly of claim 20, wherein the controller further includes a sensor associated with the communication test button and a processor programmed to perform a telemetry test operation in response to activation of the sensor by the communication test button.

22. The wireless communications assembly of claim 21, wherein the telemetry test operation includes prompting an antenna of the programmer head to attempt to wirelessly communicate with an implantable medical device.

23. The wireless communications assembly of claim 22, wherein the telemetry test operation further includes reviewing a signal strength at the antenna.

24. The wireless communications assembly of claim 23, wherein the telemetry test operation further includes at least one of:

prompting a display of the programmer head to indicate the reviewed signal strength;

continuously reviewing a signal strength at the antenna and prompting a corresponding display at the programmer head for a predetermined length of time.

25. The wireless communications assembly of claim 24, wherein the controller includes at least one indicator configured to convey a status or state of the wireless communications assembly relative to one or both of the IMD and the programmer.

26. The wireless communications assembly of claim 25, wherein the at least one indicator includes a first light emitting device.

27. The wireless communications assembly of claim 26, wherein the first light emitting device is formatted to emit visible light, the at least one indicator further including a second light emitting device formatted to emit light at a wavelength not visible to a human eye.

28. The wireless communications assembly of claim 27, wherein the first light emitting device is formatted to emit a first color of light indicative of a normal operational mode, the at least one indicator further including a second light emitting device formatted to emit light a second color of light indicative of an error operational mode.

29. The wireless communications assembly of claim 26, wherein the controller further includes a case defining a top, a bottom, a front, a back and first and second opposing sides, and further wherein the at least one indicator includes a first indicator extending along the first side.

30. The wireless communications assembly of claim 26, wherein the controller include a case maintaining a button, and further wherein the at least one indicator includes an icon formed by the button, the icon being illuminated by the first light emitting device.

* * * * *